(12) United States Patent
Yorino et al.

(10) Patent No.: US 11,535,689 B2
(45) Date of Patent: Dec. 27, 2022

(54) POLY (METH) ACRYLIC ACID (SALT)-BASED PARTICULATE WATER-ABSORBING AGENT AND PRODUCTION METHOD THEREFOR

(71) Applicant: NIPPON SHOKUBAI CO., LTD., Himeji (JP)

(72) Inventors: Tsuyoshi Yorino, Himeji (JP); Daisuke Takeda, Himeji (JP); Yoshitaka Ikeuchi, Himeji (JP); Shigeru Sakamoto, Himeji (JP); Yoshihiro Shobo, Himeji (JP); Yoshifumi Adachi, Himeji (JP); Ryota Wakabayashi, Himeji (JP); Daisuke Takagi, Himeji (JP); Sachie Kitabata, Himeji (JP)

(73) Assignee: NIPPON SHOKUBAI CO., LTD., Himeji (JP)

(*) Notice: Subject to any disclaimer, the term of this patent is extended or adjusted under 35 U.S.C. 154(b) by 1211 days.

(21) Appl. No.: 15/737,884

(22) PCT Filed: Jun. 20, 2016

(86) PCT No.: PCT/JP2016/068311
§ 371 (c)(1),
(2) Date: Dec. 19, 2017

(87) PCT Pub. No.: WO2016/204302
PCT Pub. Date: Dec. 22, 2016

(65) Prior Publication Data
US 2018/0298132 A1 Oct. 18, 2018

(30) Foreign Application Priority Data
Jun. 19, 2015 (JP) .............................. JP2015-123529

(51) Int. Cl.
| | |
|---|---|
| C08F 220/06 | (2006.01) |
| C08J 3/12 | (2006.01) |
| C08J 3/24 | (2006.01) |
| C08K 5/06 | (2006.01) |
| C08K 5/19 | (2006.01) |
| C08K 5/42 | (2006.01) |
| C08K 5/32 | (2006.01) |
| C08K 5/17 | (2006.01) |
| C08K 5/1535 | (2006.01) |
| A61L 15/24 | (2006.01) |
| A61L 15/60 | (2006.01) |
| C08F 220/00 | (2006.01) |
| C08F 6/00 | (2006.01) |
| A61L 15/00 | (2006.01) |

(52) U.S. Cl.
CPC ............ *C08F 220/06* (2013.01); *A61L 15/00* (2013.01); *A61L 15/24* (2013.01); *A61L 15/60* (2013.01); *C08F 6/00* (2013.01); *C08F 220/00* (2013.01); *C08J 3/12* (2013.01); *C08J 3/24* (2013.01); *C08K 5/06* (2013.01); *C08K 5/1535* (2013.01); *C08K 5/17* (2013.01); *C08K 5/175* (2013.01); *C08K 5/19* (2013.01); *C08K 5/32* (2013.01); *C08K 5/42* (2013.01); *C08J 2333/00* (2013.01); *C08J 2333/02* (2013.01)

(58) Field of Classification Search
CPC ...... C08F 220/06; C08F 220/00; A61L 15/00; A61L 15/24; A61L 15/60; C08J 3/12; C08J 3/24; C08K 5/19; C08K 5/17; C08K 5/42; C08K 5/175; C08K 5/1535; C08K 5/32
See application file for complete search history.

(56) References Cited

U.S. PATENT DOCUMENTS

| | | | |
|---|---|---|---|
| 4,286,082 A | 8/1981 | Tsubakimoto et al. |
| 5,180,798 A | 1/1993 | Nakamura et al. |
| 5,275,773 A | 1/1994 | Irie et al. |
| 5,601,542 A | 2/1997 | Melius et al. |
| 5,760,080 A | 6/1998 | Wada et al. |
| 5,797,893 A | 8/1998 | Wada et al. |

(Continued)

FOREIGN PATENT DOCUMENTS

| | | |
|---|---|---|
| CN | 103619919 A | 3/2014 |
| CN | 106029220 A | 10/2016 |

(Continued)

OTHER PUBLICATIONS

Chinese Office Action dated Feb. 3, 2020, which issued in the corresponding Chinese Patent Application No. 2001680036057.4, including English translation.

(Continued)

*Primary Examiner* — Yong L Chu
(74) *Attorney, Agent, or Firm* — Dickinson Wright PLLC

(57) ABSTRACT

To provide a disposable diaper enabling reduction in re-wet amount and having an excellent speed of incorporating liquid regardless of concentration and configuration of a water-absorbing agent in an absorbent material.

A water-absorbing agent having excellent Gel Capillary Absorption (GCA) and Free Gel Bed Permeability (FGBP) is obtained by crushing a crosslinked hydrogel polymer obtained in a polymerization step to have a specific weight average particle diameter while fluid retention capacity and a surface tension of a water-absorbing agent are adjusted in a specific range, drying the crushed crosslinked hydrogel polymer, and then adding a liquid permeability enhancer thereto during surface crosslinking or after surface crosslinking.

12 Claims, 4 Drawing Sheets

(56) References Cited

U.S. PATENT DOCUMENTS

| | | |
|---|---|---|
| 5,837,789 A | 11/1998 | Stockhausen et al. |
| 6,100,305 A | 8/2000 | Miyake et al. |
| 6,297,335 B1 | 10/2001 | Funk et al. |
| 7,108,916 B2 | 9/2006 | Ehrnsperger et al. |
| 7,473,739 B2 | 1/2009 | Dairoku et al. |
| 8,822,582 B2 | 9/2014 | Smith et al. |
| 2006/0204755 A1† | 9/2006 | Torii |
| 2008/0234420 A1 | 9/2008 | Smith et al. |
| 2010/0009846 A1 | 1/2010 | Ikeuchi et al. |
| 2010/0240823 A1 | 9/2010 | Sakamoto et al. |
| 2011/0078298 A1 | 3/2011 | Sakai et al. |
| 2011/0126079 A1 | 5/2011 | Wu et al. |
| 2011/0301560 A1 | 12/2011 | Fujimura et al. |
| 2011/0313113 A1 | 12/2011 | Sakamoto et al. |
| 2012/0184670 A1 | 7/2012 | Kobayashi et al. |
| 2012/0258851 A1* | 10/2012 | Nakatsuru ............... A61L 15/48 502/7 |
| 2012/0277096 A1 | 11/2012 | Smith et al. |
| 2013/0026412 A1† | 1/2013 | Machida |
| 2013/0101851 A1 | 4/2013 | Takaai et al. |
| 2013/0130017 A1 | 5/2013 | Takatori et al. |
| 2014/0193641 A1* | 7/2014 | Torii ..................... C08F 220/06 428/402 |
| 2014/0296465 A1 | 10/2014 | Sakamoto et al. |
| 2015/0225514 A1† | 8/2015 | Kimura |
| 2015/0259494 A1 | 9/2015 | Takaai et al. |
| 2015/0273433 A1† | 10/2015 | Nakatsuru |
| 2015/0376318 A1 | 12/2015 | Haag et al. |
| 2016/0199529 A1 | 7/2016 | Torii et al. |
| 2016/0207226 A1 | 7/2016 | Torii et al. |
| 2017/0014801 A1 | 1/2017 | Ikeuchi et al. |

FOREIGN PATENT DOCUMENTS

| | | |
|---|---|---|
| EP | 0574248 A2 | 12/1993 |
| EP | 2 727 953 A1 | 5/2014 |
| EP | 3 112 022 A1 | 1/2017 |
| EP | 3 202 823 A1 | 8/2017 |
| EP | 3202823 A1 | 8/2017 |
| JP | 55133413 A | 10/1980 |
| JP | 10119042 A | 5/1998 |
| JP | 2000-63527 | 2/2000 |
| JP | 4341143 B2 | 7/2009 |
| JP | 201498172 A | 5/2014 |
| JP | 2014198853 A | 10/2014 |
| WO | 9719116 A1 | 5/1997 |
| WO | 2004096304 A1 | 11/2004 |
| WO | 2008096713 A1 | 8/2008 |
| WO | 2009075204 A1 | 6/2009 |
| WO | 2010073658 A1 | 7/2010 |
| WO | 2011040472 A1 | 4/2011 |
| WO | 2011040530 A1 | 4/2011 |
| WO | 2011078298 A1 † | 6/2011 |
| WO | 2011126079 A1 † | 10/2011 |
| WO | 2013002387 A1 | 1/2013 |
| WO | 2014/054731 A1 | 4/2014 |
| WO | 2014118024 A1 | 8/2014 |
| WO | 2015030129 A1 | 3/2015 |
| WO | 2015030130 A1 | 3/2015 |
| WO | 2015129917 A1 | 9/2015 |
| WO | 2015/030130 A1 | 7/2016 |

OTHER PUBLICATIONS

Modern Superabsorbent Polymer Technology, Buchholz, F. and Graham, A. (ed), Wiley-VCH, ISBN 0-471-19411-5, pp. 69-117.

Extended European Search Report dated May 25, 2018, which issued in the corresponding Patent Application No. 16811776.0.

Indonesian Office Action dated Jan. 27, 2020, which issued in the Indonesian counterpart Patent Application No. P00201800357, including English translation.

Indonesian Office Action dated Apr. 30, 2020, which issued in the corresponding Indonesian Patent Application No. P00201800357, including English translation.

Chinese Office Action dated Jan. 6, 2021, which issued in the corresponding Chinese Patent Application No. 201680036057.4, including English translation.

Chinese Examiner's Decision of Refusal dated May 7, 2021, which issued in the corresponding Chinese Patent Application No. 201680036057.4.

European Communication Pursuant to Article 94(3) EPC dated Aug. 5, 2021, which issued in the corresponding European Patent Application No. 16 811 776.0.

\* cited by examiner
† cited by third party

POLY (METH) ACRYLIC ACID (SALT)-BASED PARTICULATE WATER-ABSORBING AGENT AND PRODUCTION METHOD THEREFOR

TECHNICAL FIELD

The present invention relates to a particulate water-absorbing agent containing poly(meth)acrylic acid (salt)-based water-absorbing resin particles as a main component. More specifically, the present invention relates to a particulate water-absorbing agent capable of improving the performance of an absorbent article such as a disposable diaper.

BACKGROUND ART

A water-absorbing resin (SAP/Super Absorbent Polymer) is a polymer gelling agent having water swellable property and water insoluble property and exhibits an excellent characteristic for absorbing body-fluids. For this reason, a water-absorbing agent containing a water-absorbing resin as a main component is often used for absorbent articles such as disposable diapers and sanitary napkins, agriculture/horticulture water retention agents, industrial waterproofing materials, and the like. Many kinds of monomers and hydrophilic polymers have been proposed as a raw material of such a water-absorbing resin that constitutes the water-absorbing agent. However, a poly(meth)acrylic acid (salt)-based water-absorbing resin using (meth)acrylic acid and/or a salt thereof as a main component is most often used in industry from the viewpoint of price and performance. Such a water-absorbing resin is produced through a polymerization step, a drying step, an optional step for removing a non-dried product, a pulverizing step, a classification step, a surface crosslinking step, and the like (Non-Patent Literature 1).

To give a disposable diaper, which is a primary application for a water-absorbing resin (water-absorbing agent), as an example, remedies for urine leakage and skin rash are in need. As a method for evaluating these problems, a method for measuring a re-wet amount from a disposable diaper under pressure and a method for measuring liquid absorption time of a disposable diaper under pressure have been proposed. It is estimated that, in a case where urine is hardly incorporated into a disposable diaper while the body weight of a wearer of a disposable diaper is applied, or in a case where a water-absorbing agent absorbs urine slowly even if urine is incorporated into the disposable diaper, urine leakage or skin rash occurs. Then, it is considered that improvement in absorbability of a water-absorbing agent under pressure and improvement in water absorption speed of the water-absorbing agent lead to reduction in the re-wet amount of a disposable diaper and the liquid absorption time, and further lead to reduction in urine leakage and skin rash.

In recent years, disposable diapers have been widespread and widely used all over the world. In a disposable diaper, a water-absorbing agent is used in the form of being mixed with pulp. Depending on regions, an absorbent material having a larger weight of pulp than a weight of a water-absorbing agent, that is, a so-called low-water-absorbing-agent-concentration absorbent material (water-absorbing resin concentration: less than 50 wt %) is preferably used. However, in other regions, an absorbent material having a larger weight of a water-absorbing agent than a weight of pulp, that is, a so-called high-water-absorbing-agent-concentration absorbent material (water-absorbing resin concentration: 50 wt % or more) is preferably used, and an absorbent material containing only a water-absorbing resin without use of pulp is also preferably used.

Conventionally, in order to reduce the re-wet amount of these disposable diapers and to reduce the liquid absorption time of these disposable diapers, many techniques for improving absorption characteristics under pressure have been proposed.

Specific examples of the proposition include a technique for using a water-absorbing agent having a large sum of fluid retention capacities under four different of pressures (PAI) for a disposable diaper (Patent Literature 1), a technique for improving diffusivity of liquid not only in a vertical direction but also in a horizontal direction in an SAP layer under pressure (Patent Literatures 2 and 3), a technique for improving fluid retention capacity under pressure while the SAP amount per unit area is large (Patent Literatures 4 and 5), and a technique for improving fluid retention capacity under pressure measured while there is a difference in height between a glass filter in contact with a water-absorbing agent and a liquid surface of a liquid supply side (Patent Literatures 6 and 7). Particularly, in Patent Literature 7, it is proposed that a new parameter for evaluating liquid suction capability in a short time that is called Gel Capillary Absorption (GCA) is introduced and the re-wet amount can be reduced as the value of GCA is increased.

Indeed, in the case of using a water-absorbing agent having improved GCA, in the absorbent material, which has been hitherto mainly used, containing a water-absorbing agent in a small amount, the effect of reducing the re-wet amount is exerted; on the other hand, a problem arises in that in a high-concentration absorbent material or an absorbent material without use of pulp, the expected effect is not always able to be recognized in view of the speed of incorporating liquid and the re-wet amount.

Further, as a method for producing a water-absorbing agent having improved GCA in Patent Literature 7, a technique of introducing foaming, a technique of mixing a fine particulate dried product of a water-absorbing resin with water or hot water at a high speed so as to be granulated, and the like have been used.

Further, as a technique for crushing a polymerization gel, there have been proposed a technique for crushing a polymerization gel with a specific energy to form gel particles (Patent Literatures 8 to 10) and a technique for crushing a polymerization gel with a gel-crusher having a specific shape (a meat chopper) (Patent Literatures 11 to 14).

In a foaming technique described in the above-described Patent Literature 7 and the like, dispersion stabilization of bubbles in a monomer solution is difficult to achieve, and stable production is difficult. Further, in a case where bubbles are stabilized by a large amount of a surfactant, a problem such as a decrease in surface tension may occur.

As for the technique of introducing foaming described in the above-described Patent Literature 7 and the like, there are problems in that the amount of fine powder, which does not become a product, produced is increased during crushing so that production efficiency is largely decreased, and in that physical properties such as fluid retention capacity under pressure are largely degraded since a dried product of the water-absorbing resin becomes brittle so as to be easily damaged in a transporting step. Further, as for a granulating technique described in the above-described Patent Literature 7 and the like, there is a room for improvement in production efficiency since water or hot water is added to the fine particulate dried product of the water-absorbing resin and then the mixture is granulated and dried, and there is a problem in performance degradation due to deterioration of the water-absorbing resin caused by performing a drying process multiple times. Furthermore, in techniques relating to a gel-crusher and crushing conditions (Patent Literatures 8 to 14) and techniques of adding an additive such as polyethylene glycol or a hydrophobic substance during polymerization of a polymerization gel or during crushing of a polymerization gel (Patent Literatures 15 to 12), there are problems in that the crushing conditions are not sufficient for improving GCA and in that a surface tension is largely decreased. Techniques of producing granulated particles by a reverse phase suspension polymerization method (Patent Literatures 21 and 22) have also been proposed. However, there are problems in that processes are cumbersome and in that troubles due to remaining of an organic solvent occur. Moreover, the effect of improving the performance of a disposable diaper is not sufficient, for example, the re-wet amount is increased by a decrease in surface tension.

CITATION LIST

Patent Literatures

Patent Literature 1: U.S. Pat. No. 5,601,542
Patent Literature 2: U.S. Pat. No. 5,760,000
Patent Literature 3: U.S. Pat. No. 5,797,893
Patent Literature 4: U.S. Pat. No. 6,297,335
Patent Literature 5: WO 2011/040472 A
Patent Literature 6: U.S. Pat. No. 7,108,916
Patent Literature 7: WO 2015/129917 A
Patent Literature 8: WO 2011/126079 A
Patent Literature 9: WO 2013/002387 A
Patent Literature 10: WO 2014/118024 A
Patent Literature 11: WO 2015/D34129 A
Patent Literature 12: WO 2015/030130 A
Patent Literature 13: EP 0574248 A
Patent Literature 14: U.S. Pat. No. 5,275,773
Patent Literature 15: WO 2008/096713 A
Patent Literature 16: WO 2009/075264 A
Patent Literature 17: JP 4341143 B1
Patent Literature 18: WO 2010/073658 A
Patent Literature 19: WO 97/19116 A
Patent Literature 20: WO 2004/096304 A
Patent Literature 21: U.S. Pat. No. 5,180,798
Patent Literature 22: US 2013/0,130,017 A Non-Patent Literature Non-Patent Literature 1: Modern Superabsorbent Polymer Technology (1998)

SUMMARY OF INVENTION

Technical Problem

An object of the present invention is to solve at least one of problems described below.

An object of the present invention is to provide a poly (meth)acrylic acid (salt)-based particulate water-absorbing agent enabling reduction in re-wet amount and having an excellent speed of incorporating liquid.

Further, another object of the present invention is to provide a method for producing a poly(meth)acrylic acid (salt)-based particulate water-absorbing agent enabling reduction in re-wet amount and having an excellent speed of incorporating liquid.

Still another object of the present invention is to provide a hygienic material (for example, a disposable diaper) enabling reduction in re-wet amount in a high concentration of an absorbing agent and having an excellent speed of incorporating liquid.

Solution to Problem

Hereinbefore, many water-absorbing resins whose parameters are controlled have been proposed, and the present inventors have filed the patent application shown in Patent Literature 7, which is focused on Gel Capillary Absorption (GCA) that is a new parameter with respect to the related arts such as Patent Literatures 1 to 6. However, insufficient points have still been found.

In this regard, in order to solve the above problem, the present inventors have conducted intensive studies. As a result, liquid permeability has still been insufficient in Patent Literature 7 which is focused on Gel Capillary Absorption (GCA) that is a new parameter. The present inventors have found that the above-described problem can be solved when Free Gel Bed Permeability (FGBP) that is a new index of liquid permeability is high in addition to GCA.

That is, the present invention provides a method for producing a poly(meth)acrylic acid (salt)-based particulate water-absorbing agent containing poly(meth)acrylic acid (salt)-based water-absorbing resin particles as a main component, the method including: (i) a step for preparing a (meth)acrylic acid (salt)-based aqueous monomer solution; (ii) a step for polymerizing the (meth)acrylic acid (salt)-based aqueous monomer solution; (iii) a step for gel-crushing a crosslinked hydrogel polymer during polymerization or after polymerization to obtain hydrogel particles;

(iv) a step for drying the hydrogel particles to obtain a dried product; (v) a step for pulverizing and/or classifying the dried product to obtain water-absorbing resin powder; (vi) a step for surface crosslinking the water-absorbing resin powder to obtain water-absorbing resin particles; and (vii) a step for adding a liquid permeability enhancer to the water-absorbing resin powder or the water-absorbing resin particles, wherein the method further includes adding an adhesion controlling agent, which controls adhesion of the crosslinked hydrogel polymer and/or the hydrogel particles, in the step (iii) or before the step (iii), a solids content of the hydrogel particles is adjusted to 10 wt % to 80 wt % and a weight average particle diameter of the hydrogel particles converted to the dried product is adjusted to 50 μm to 650 μm, and a surface tension of the poly(meth)acrylic acid (salt)-based particulate water-absorbing agent is adjusted to 60 mN/m or more, and a fluid retention capacity without pressure (CRC) is adjusted to 28 g/g or more.

Further, according to the present invention, there is provided a polyacrylic acid (salt)-based particulate water-absorbing agent including polyacrylic acid (salt)-based water-absorbing resin particles as a main component, the polyacrylic acid (salt)-based particulate water-absorbing agent satisfying the following (1) to (5): (1) a fluid retention capacity without pressure (CRC) is 28 g/g or more; (2) GCA is 28.0 g/g or more; (3) a relation between FGBP and GCA satisfies, in a case where GCA is in a range of 28.0 g/g or more and less than 36.0 g/g, FGBP $\geq -10 \times 10^{-9} \times GCA + 380 \times 10^{-9}$ cm$^2$, and in a case where GCA is 36.0 g/g or more, FGBP $\geq 30 \times 10^{-9}$ cm$^2$; (4) a weight average particle diameter (D50) of the particulate water-absorbing agent is 300 μm to 500 μm; and (5) a surface tension is 60 mN/m or more.

Effect of the Invention

According to the present invention, at least one of the following effects is achieved.

It is possible to provide a poly(meth)acrylic acid (salt)-based particulate water-absorbing agent enabling reduction in re-wet amount and having an excellent speed of incorporating liquid.

Further, it is possible to provide a method for producing a poly(meth)acrylic acid (salt)-based particulate water-absorbing agent enabling reduction in re-wet amount and having an excellent speed of incorporating liquid.

It is possible to provide a hygienic material (for example, a disposable diaper) enabling reduction in re-wet amount in a high concentration of an absorbing agent and having an excellent speed of incorporating liquid.

DESCRIPTION OF EMBODIMENTS

Figure 1:
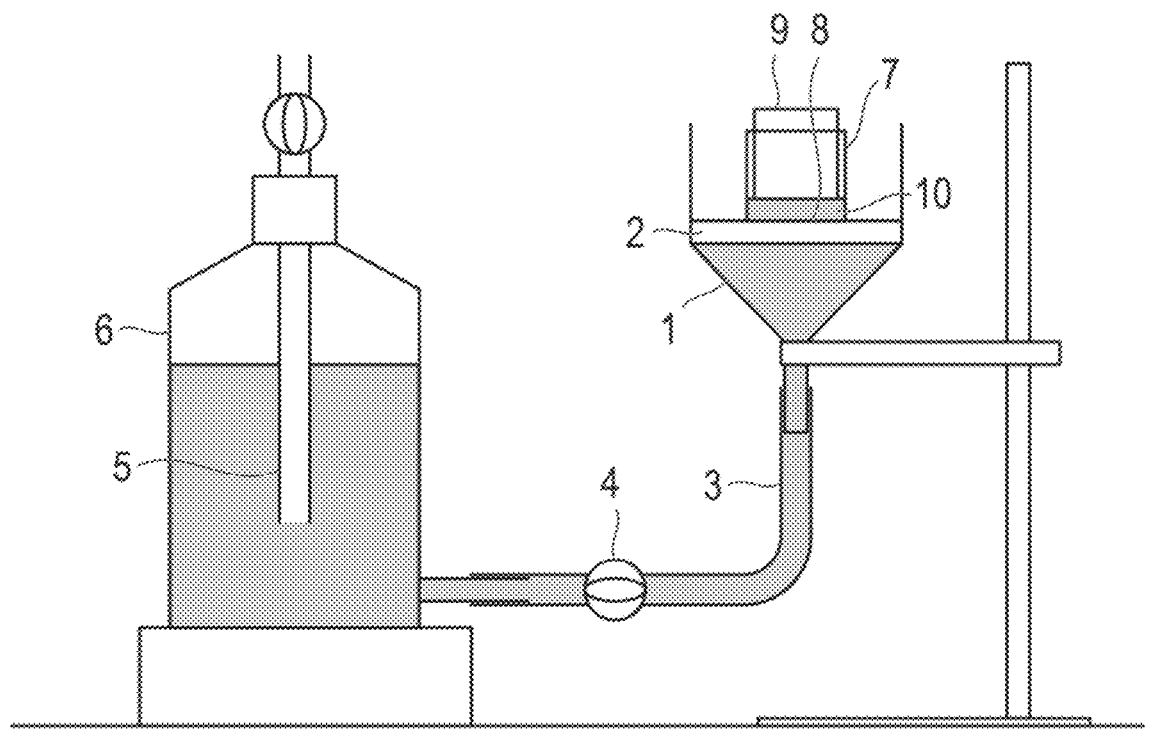
FIG. 1 is a schematic diagram of an apparatus used for GCA measurement of the present invention.

Hereinafter, a particulate water-absorbing agent according to the present invention and a production method therefor is described in detail. However, the scope of the present invention is not limited thereto but can be appropriately embodied with modifications other than the following exemplary embodiments but not departing from the gist of the present invention. Specifically, the present invention is not limited to the following embodiments, but can be modified variously in the range indicated by claims. Embodiments obtained by appropriately combining technical means disclosed in different embodiments are also included in the technical scope of the present invention.

[1] Definition of Terms (1-1) "Particulate Water-Absorbing Agent"

In the present invention, the term "particulate water-absorbing agent" is a gelling agent of water-based liquid containing water-absorbing resin particles as a main component (preferably 60 wt % or more, more preferably 80 wt % or more, and moat preferably 90 wt % or more). As another optional component, the particulate water-absorbing agent may contain water, inorganic fine particles, a moisture absorption blocking inhibitor, a cationic polymer compound, a water-soluble polyvalent metal cation-containing compound, a surfactant, a dust inhibitor, a coloring preventing agent, a urine resistance improver, a deodorant, a perfume, an antimicrobial agent, a foaming agent, a pigment, a dye, a fertilizer, an oxidizing agent, a reducing agent, and the like in an amount of 0 wt % to 10 wt %, preferably 0.1 wt % to 1 wt % for each. Incidentally, the "particulate water-absorbing agent" is simply referred to as the "water-absorbing agent" in some cases.

(1-2) "Water-Absorbing Resin"

In the present invention, a "water-absorbing resin" means a polymer gelling agent having water swellable property and water insoluble property. Incidentally, "water swellable" indicates that CRC (fluid retention capacity without pressure) as defined in ERT441.2-02 is 5 g/g or more, and "water insoluble" indicates that Ext (soluble component) as defined in ERT470.2-02 is 0 wt % to 50 wt %.

Further, the whole amount (100 wt %) of the water-absorbing resin is not necessarily consisting of a polymer. The water-absorbing resin may contain an additive or the like in a range maintaining the above-mentioned properties. In the present invention, a water-absorbing resin composition containing a small amount of an additive is also collectively referred to as a water-absorbing resin. Incidentally, the water-absorbing resin preferably has a powdery shape, and particularly preferably has a powdery shape having a particle size described below. Incidentally, in the present invention, the "water-absorbing resin" is also referred to as "water-absorbing resin powder" or "water-absorbing resin particles" in some cases.

(1-3) "Poly(Meth)Acrylic Acid (Salt)-Based Water-Absorbing Resin"

The term "poly(meth)acrylic acid (salt)-based water-absorbing resin" in the present invention means a polymer optionally containing a graft component and mainly containing a (meth)acrylic acid and/or a salt thereof (hereinafter, referred to as a (meth)acrylic acid (salt)) as a repeating unit.

Specifically, the poly(meth)acrylic acid (salt)-based water-absorbing resin means a polymer containing a (meth)acrylic acid (salt) in an amount of 50 mol % to 100 mol %, and a water-absorbing resin containing a (meth)acrylic acid (salt) in an amount of preferably 70 mol % to 100 mol %, more preferably 90 mol % to 100 mol %, and particularly preferably substantially 100 mol % per the total monomers used in polymerization (excluding a crosslinking agent). Further, in the present invention, a polymer having a poly(meth)acrylic acid salt type (neutralized) is also collectively referred to as a poly(meth)acrylic acid (salt)-based water-absorbing resin.

(1-4) "EDANA" and "ERT"

"EDANA" is an abbreviation for European Disposables and Nonwovens Associations. "ERT" is an abbreviation of methods for measuring a water-absorbing resin (EDANA Recommended Test Methods), which is an European standard (essentially the world standard). In the meantime, in the present invention, unless otherwise specified, physical properties of a water-absorbing resin are measured in conformity with the original document of ERT (publicly-known document: revised in 2002).

(1-4-1) "CRC" (ERT441.2-02)

"CRC" is an abbreviation for Centrifuge Retention Capacity, and means fluid retention capacity without pressure (also referred to as "fluid retention capacity" in some cases) of a water-absorbing resin. Specifically, "CRC" means fluid retention capacity (unit; g/g) obtained after 0.2 g of a water-absorbing resin is input in a bag made of nonwoven fabric, is then freely swollen in 0.9 wt % of aqueous sodium chloride solution in a largely excessive amount for 30 minutes and then is further drained by a centrifuge (250 G).

(1-4-2) "AAP" (ERT442.2-02)

"AAP" is an abbreviation of Absorption Against Pressure and means fluid retention capacity under pressure of a water-absorbing resin. Specifically, "AAP" means fluid retention capacity (unit; g/g) obtained after 0.9 g of a water-absorbing resin is swollen in 0.9 wt % of aqueous sodium chloride solution in a largely excessive amount under a load of 2.06 kPa (21 g/cm$^2$, 0.3 psi) for 1 hour. Further, Absorption Against Pressure is expressed as Absorption Under Pressure in ERT442.2-02, but these are substantially the same.

(1-4-3) "PSD" (ERT420.2-02)

"PSD" is an abbreviation of Particle Size Distribution and means a particle size distribution of a water-absorbing resin measured by sieve classification. Incidentally, the weight average particle diameter (D50) and the logarithmic standard deviation (ac) in particle size distribution are measured by the same method as "(3) Mass-Average Particle Diameter (D50) and Logarithmic Standard Deviation (ac) of Particle Diameter Distribution" described in U.S. Pat. No. 7,638,570.

(1-4-4) "Ext" (ERT470.2-02)

"Ext" is an abbreviation of Extractables and means a water soluble component (amount of water-soluble component) of a water-absorbing resin. Specifically, "Ext" is the amount of dissolved polymer (unit; wt %) after 1.0 g of a water-absorbing resin is added to 200 ml of 0.9 wt % of aqueous sodium chloride solution and the resulting mixture is stirred for 16 hours at 500 rpm. The amount of dissolved polymer is measured by pH titration.

(1-5) GCA (Refer to Patent Literature 7)

"GCA" is a new parameter (Gel Capillary Absorption) firstly focused and described in Patent Literature 7 and evaluates liquid absorption ability under a load of 0.05 psi for 10 minutes with a difference in height of 10 cm between the upper surface of a glass filter and the meniscus at the lower portion of a Mariotte tube.

(1-6) FGBP (Free Gel Bed Permeability)

FGBP measures liquid permeability of a gel layer under load after 0.9 g of a water-absorbing agent is freely swollen in a cell without any changes by a physiological saline solution. While GBP known as the related prior art that is described as "GBP" in the patent literature WO 2004/096304 A or the like is measurement for a specific particles size (only particles having a particle size of 300 μm to 600 μm are sieved) in the whole particles, FGBP is measurement for a particle size without any changes and without sieving (that is, whole absorbing agent particles). The original liquid permeability of the water-absorbing agent can be evaluated with use of FGBP.

(1-7) Others

In the present specification, "X to Y" indicating a range means "equal to or more than X and equal to or less than Y." Further, "t (ton)" as a unit of weight means "etricton." Moreover, unless otherwise specified, "ppm" means "ppm by weight." Furthermore, "weight" and "mass," "wt %" and "mass %," and "parts by weight" and "parts by mass" are assumed to be synonymous, respectively. In addition, " . . . acid (salt)" means " . . . acid and/or a salt thereof" and "(meth)acrylic" means "acrylic and/or methacrylic." Furthermore, unless otherwise specified, physical properties and the like are measured at room temperature (20° C. to 25° C.) at a relative humidity of 40% RH to 50% RH.

[2] Method for Producing Particulate Water-Absorbing Agent

As described above, a method for producing a particulate water-absorbing agent according to the present invention is a method for producing a poly(meth)acrylic acid (salt)-based particulate water-absorbing agent containing poly(meth) acrylic acid (salt)-based water-absorbing resin particles as a main component, the method including: (i) a step for preparing a (meth)acrylic acid (salt)-based aqueous monomer solution; (ii) a step for polymerizing the (meth)acrylic acid (salt)-based aqueous monomer solution; (iii) a step for gel-crushing a crosslinked hydrogel polymer during polymerization or after polymerization to obtain hydrogel particles; (iv) a step for drying the hydrogel particles to obtain a dried product; (v) a step for pulverizing and/or classifying the dried product to obtain water-absorbing resin powder; (vi) a step for surface crosslinking the water-absorbing resin powder to obtain water-absorbing resin particles, and (vii) a step for adding a liquid permeability enhancer to the water-absorbing resin powder or the water-absorbing resin particles, in which the method further includes adding an adhesion controlling agent, which controls adhesion of the crosslinked hydrogel polymer and/or the hydrogel particles, in the step (iii) or before the step (iii), a solids content of the hydrogel particles is adjusted to 10 wt % to 80 wt % and a weight average particle diameter of the hydrogel particles converted to the dried product is adjusted to 50 μm to 650 μm, a surface tension of the poly(meth)acrylic acid (salt)-based particulate water-absorbing agent is adjusted to 60 mN/m or more, and a fluid retention capacity without pressure (CRC) is adjusted to 28 g/g or more.

As described above, by crushing the crosslinked hydrogel polymer obtained in a polymerization step to have a specific weight average particle diameter (a weight average particle diameter of the hydrogel particles converted to the dried product of 50 μm to 650 μm) and drying the crushed crosslinked hydrogel polymer, and then adding a liquid permeability enhancer thereto during surface crosslinking or after surface crosslinking, it is possible to obtain a water-absorbing agent having excellent Gel Capillary Absorption (GCA) and Free Gel Bed Permeability (FGBP) and to achieve the desired object of the present invention.

Further, according to the present invention, there is also provided a method for producing a poly(meth)acrylic acid (salt)-based particulate water-absorbing agent containing poly(meth)acrylic acid (salt)-based water-absorbing resin particles as a main component, the method including: (i) a step for preparing a (meth)acrylic acid (salt)-based aqueous monomer solution; (ii) a step for polymerizing the (meth) acrylic acid (salt)-based aqueous monomer solution; (iii) a step for gel-crushing a crosslinked hydrogel polymer during polymerization or after polymerization to obtain hydrogel particles; (iv) a step for drying the hydrogel particles to obtain a dried product; (v) a step for pulverizing and/or classifying the dried product to obtain water-absorbing resin powder; (vi) a step for surface crosslinking the water-absorbing resin powder to obtain water-absorbing resin particles; and (vii) a step for adding a liquid permeability enhancer to the water-absorbing resin powder or the water-absorbing resin particles, in which the method further includes adding an adhesion controlling agent, which controls adhesion of the crosslinked hydrogel polymer and/or the hydrogel particles, in the step (iii) or before the step (iii), a solids content of the hydrogel particles is adjusted to 10 wt % to 80 wt % and a weight average particle diameter of the hydrogel particles is adjusted to 100 μm to 900 μm, a surface tension of the poly(meth)acrylic acid (salt)-based particulate water-absorbing agent is adjusted to 60 mN/m or more, and a fluid retention capacity without pressure (CRC) is adjusted to 28 g/g or more.

As described above, by crushing the crosslinked hydrogel polymer obtained in a polymerization step to have a specific weight average particle diameter (a weight average particle diameter of the hydrogel particles of 100 μm to 900 μm) and drying the crushed crosslinked hydrogel polymer, and then adding a liquid permeability enhancer thereto during surface crosslinking or after surface crosslinking, it is possible to obtain a water-absorbing agent having excellent Gel capillary Absorption (GCA) and Free Gel Bed Permeability (FGBP) and to achieve the desired object of the present invention.

In the present specification, at least one of a case where "the weight average particle diameter of the hydrogel particles converted to the dried product is 50 μm to 650 μm" and a case where "the weight average particle diameter of the hydrogel particles is 100 μm to 900 μm" is simply referred to as a case where "the particle diameter after gel-crushing is significantly small" in some cases.

Incidentally, in the above-described production method, it is preferable to "sequentially" perform the step (i) to step (vii) in this order, but each step may be simultaneously performed with the prior step or the post step.

The period of time between the above steps including transportation time or storage time is appropriately determined, and is preferably 0 seconds or longer and 2 hours or shorter, and more preferably 1 second or longer and 1 hour or shorter.

Hereinafter, the method for producing a particulate water-absorbing agent according to the present invention is described mainly in a temporal order. However, each of the production methods is only required to include the above-mentioned essential steps, and may further include another step within a range not departing from the gist of each of the production methods.

(2-1) Step for Preparing (Meth)Acrylic Acid (Salt)-Based Aqueous Monomer Solution (Step (i))

In the present specification, "(meth)acrylic acid (salt)-based aqueous monomer solution" is an aqueous monomer solution containing a (meth)acrylic acid (malt) as a main component, and optionally containing a crosslinking agent, a graft component, or a minor component (chelating agent, surfactant, dispersant, or the like) and prepared containing these components constituting a water-absorbing resin. In other words, "(meth)acrylic acid (salt)-based aqueous monomer solution" means a solution subjected to polymerization as it is after being added with a polymerization initiator.

The above-mentioned (meth)acrylic acid (salt) may be unneutralized or a salt type (fully neutralized or partially neutralized). Further, the aqueous monomer solution may have a concentration larger than a saturation concentration. Even a supersaturated aqueous solution of a (meth)acrylic acid (salt) or a slurry aqueous solution thereof (aqueous dispersion) is assumed to be the (meth)acrylic acid (salt)-based aqueous monomer solution of the present invention. Incidentally, from the viewpoint of physical properties of the resulting water-absorbing resin, it is preferable to use a (meth)acrylic acid (salt)-based aqueous monomer solution having a concentration equal to or lower than the saturation concentration.

Further, as a solvent for dissolving a monomer, water is preferable. A (meth)acrylic acid (salt)-based monomer is handled as an aqueous solution. Here, "aqueous solution" is not limited to a case where 100 wt % of the solvent is water. A water-soluble organic solvent (for example, alcohol or the like) may be used together with water in an amount of 0 wt % to 30 wt %, preferably 6 wt % to 5 wt % per 100 wt % of the total amount of the solvent. In the present invention, these solutions are assumed to be aqueous solutions.

In the present specification, "(meth)acrylic acid (salt)-based aqueous monomer solution during preparation" described below means an aqueous solution of the above-mentioned (meth)acrylic acid (salt) before all the components are mixed with the aqueous monomer solution containing the (meth)acrylic acid (salt) as a main component. Specifically, an aqueous (meth)acrylic acid solution or a fully neutralized or partially neutralized aqueous (meth)acrylic acid (salt) solution corresponds thereto.

By further neutralizing the (meth)acrylic acid (salt)-based aqueous monomer solution during preparation or mixing water as a solvent or the above minor component or the like to the (meth)acrylic acid (salt)-based aqueous monomer solution, a final (meth)acrylic acid (salt)-based aqueous monomer solution is obtained. Incidentally, this final (meth)acrylic acid (salt)-based aqueous monomer solution before being put into a polymerization apparatus or before starting to polymerize after being put into the polymerization apparatus is referred to as "(meth)acrylic acid (salt)-based aqueous monomer solution after preparation before a polymerization step."

(2-1-1) Monomer

For the water-absorbing resin of the present invention, a monomer containing a (meth)acrylic acid (salt) as a main component is used. The "main component" means that a (meth)acrylic acid (salt) is contained in an amount of usually 50 mol % or more, preferably 70 mol % or more, more preferably 80 mol % or more, still more preferably 90 mol % or more, and particularly preferably 95 mol % or more (the upper limit is 100 mol %) per the total amount of monomers (excluding an internal crosslinking agent).

Incidentally, in the present invention, the poly(meth) acrylic acid (salt) is not limited to an unneutralized poly (meth)acrylic acid (salt) (the rate of neutralization is 0 mol %), but encompasses a partially neutralized or fully neutralized (the rate of neutralization is 100 mol %) poly(meth) acrylic acid (salt).

As long as a (meth)acrylic acid (salt) is contained as a main component, a monomer to become a water-absorbing resin by polymerization may be contained in addition thereto. Examples thereof include an anionic unsaturated monomer (salt) such as (anhydrous) maleic acid, itaconic acid, cinnamic acid, vinyl sulfonic acid, allyl toluene sulfonic acid, vinyl toluene sulfonic acid, styrene sulfonic acid, 2-(meth)acrylamide-2-methyl propanesulfonic acid, 2-(meth)acryloyl ethanesulfonic acid, 2-(meth)acryloyl propane sulfonic acid, or 2-hydroxyethyl (meth)acryloyl phosphate and the like; a mercapto group-containing unsaturated monomer; a phenolic hydroxy group-containing unsaturated monomer; an amide group-containing unsaturated monomer such as (meth)acrylamide, N-ethyl (meth)acrylamide, or N,N-dimethyl (meth)acrylamide and the like; and an amino group-containing unsaturated monomer such as N,N-dimethyl aminoethyl (meth)acrylate, N,N-dimethyl aminopropyl (meth)acrylate, or N,N-dimethyl aminopropyl (meth) acrylamide and the like. Further, the water-absorbing resin may contain the above-mentioned other monomers as a copolymer component.

In the present invention, the rate of neutralization of a (meth)acrylic acid (salt)-based monomer or a crosslinked hydrogel polymer after polymerization is not particularly limited, but is preferably 40 mol % to 90 mol %, more preferably 50 mol % to 85 mol %, and still more preferably 65 mol % to 80 mol % from the viewpoint of physical properties of the resulting water-absorbing resin or a reactivity of a surface crosslinking agent. In this regard, according to the preferred embodiment of the present invention, the rate of neutralization of the acrylic acid (salt)-based aqueous monomer solution in the step (i) is 40 mol % to 90 mol %.

However when the rate of neutralization is low, the water absorption speed tends to be lowered (for example, the water absorption time by vortex method is increased). On the contrary, when the rate of neutralization is high, the reactivity between the poly(meth)acrylic acid (salt)-based water-absorbing resin and the surface crosslinking agent (particularly, a dehydration-reactive surface crosslinking agent described below) tends to be lowered, the productivity tends to be reduced, or the fluid retention capacity under pressure (for example, AAP) tends to be reduced. Therefore, the rate of neutralization is preferably in the above-mentioned range.

The neutralization may be conducted to a hydrogel (crosslinked hydrogel polymer) after polymerization, as well as to the monomer and/or the aqueous monomer solution before polymerization, and both of these may be adopted together. When neutralization is performed multiple times, it is preferable that, by taking the addition amounts of all the basic compounds in consideration, the rate of neutralization is adjusted in the above-mentioned range.

In particular, when unneutralized polymerization in which the rate of neutralization is 0 mol % is conducted and neutralization is conducted in the subsequent step, the neutralization does not become uniform, and ununiform extent of surface treatment for each of the water-absorbing resin particles occurs in the surface treatment step. Thus, there is a concern that the fluid retention capacity under pressure is largely reduced. In this regard, it is preferable to perform neutralization polymerization.

Further, from the viewpoint of the fluid retention capacity without pressure (CRC) or the water absorption speed of the resulting water-absorbing resin particles (particulate water-absorbing agent), a part or the whole of the (meth)acrylic acid (salt)-based monomer or the crosslinked hydrogel polymer may be a salt type. One or more kinds of monovalent salt such as a sodium salt, a lithium salt, a potassium salt, an ammonium salt, or an amine are preferable. Among these, one or more kinds of alkali metal salt are more preferable, and a sodium salt and/or a potassium salt are still more preferable. A sodium salt is particularly preferable from the viewpoint of cost and physical properties.

(2-1-2) Internal Crosslinking Agent

In the present invention, in the above-mentioned polymerization, an internal crosslinking agent is used, as required. As the internal crosslinking agent, a known internal crosslinking agent can be used. Examples thereof include N,N'-methylene bis(meth) acrylamide, (poly)ethylene glycol di(meth)acrylate, (poly)propylene glycol di(meth)acrylate, trimethylolpropane tri(meth)acrylate, glycerin tri(meth)acrylate, glycerin acrylate methacrylate, ethylene oxide modified trimethylolpropane tri(meth)acrylate, pentaerythritol hexa(meth)acrylate, triallyl cyanurate, triallyl isocyanurate, triallyl phosphate, triallylamine, poly(meth)allyloxy alkane, (poly)ethylene glycol diglycidyl ether, glycerol diglycidyl ether, ethylene glycol, polyethylene glycol, propylene glycol, glycerin, 1,4-butanediol, pentaerythritol, ethylenediamine, ethylene carbonate, propylene carbonate, polyethylene imine, and glycidyl (meth)acrylate and the like. One or two or more kinds of these compounds can be used in consideration of the reactivity. Among these, it is preferable to use a compound having two or more polymerizable unsaturated groups.

The amount of the internal crosslinking agent used can be determined appropriately depending on the desired physical properties of the water-absorbing resin, but is appropriately adjusted such that CRC of the water-absorbing agent of the present invention is 28 g/g or more.

Specifically, the amount of the internal crosslinking agent used is preferably 0.001 mol % to 1 mol %, more preferably 0.005 mol % to 0.5 mol %, still more preferably 0.01 mol % to 0.3 mol %, and particularly preferably 0.01 mol % to 0.1 mol % with respect to 100 mol % of the (meth)acrylic acid (salt)-based monomer.

When the amount to use thereof is less than 0.001 mol %, a soluble content of the resulting water-absorbing resin becomes large, the water absorption amount under pressure cannot be sufficiently secured, and values of GCA and FGBP also not an appropriate value, which is not preferable. On the other hand, when the amount to use thereof is more than 1 mol %, the crosslink density of the resulting water-absorbing resin becomes too high and the water absorption amount cannot be sufficiently secured, and as a result, the value of GCA becomes low, which is not preferable.

In order to introduce a crosslinking structure into a polymer using the internal crosslinking agent, the internal crosslinking agent is only required to be added to a reaction system before, during, or after polymerization, or after neutralization of the monomer. Incidentally, the internal crosslinking agent may be added to a reaction system at once or in a divided manner.

(Adhesion Controlling Agent)

In order to sophisticatedly solve the problem of the present invention, an adhesion controlling agent (can also be called a fusion controlling agent) specifically described in (2-3-2) may be added during or after the step for preparing the (meth)acrylic acid (salt)-based aqueous monomer solution, and specifically, specifically, is added in the step (iii) or before the step (iii).

(2-2) Polymerization Step (Step (ii))

Examples of a polymerization method for obtaining the water-absorbing resin particles (crosslinked hydrogel polymer) of the present invention may include spray polymerization, droplet polymerization, bulk polymerization, precipitation polymerization, aqueous solution polymerization, and reverse phase suspension polymerization. In order to solve the problem of the present invention, the aqueous solution polymerization or the reverse phase suspension polymerization, which uses an aqueous solution of a monomer, is preferable.

Incidentally, in the aqueous solution polymerization, an aqueous monomer solution is polymerized without using a dispersion solvent, and the method is disclosed, for example, in U.S. Pat. Nos. 4,625,001, 4,873,299, 4,286,082, 4,973,632, 4,985,518, U.S. Pat. Nos. 5,124,416, 5,250,640, 5,264,495, 5,145,906, 5,380,808, EP 0811636 B, EP 0955086 B, EP 0922717 B, and the like.

Further, in the reverse phase suspension polymerization, an aqueous monomer solution is polymerized by being suspended in a hydrophobic organic solvent, and the method is disclosed, for example, in U.S. Pat. Nos. 4,093,776, 4,367,323, 4,446,261, 4,683,274, 5,244,735, and the like. A monomer, a polymerization initiator, and the like disclosed in these Patent Literatures can be also applied to the present invention. The concentration of an aqueous monomer solution during polymerization is not particularly limited, but is preferably 20 wt % to the saturation concentration or less, more preferably 25 wt % to 80 wt %, and still more preferably 30 Wt % to 70 wt %. When the concentration is 20 wt % or more, high productivity can be achieved, which is preferable. In the meantime, in polymerization of a monomer in the state of a slurry (aqueous dispersion of (meth)acrylate), physical properties are lowered, and therefore polymerization is preferably performed with a concentration equal to or lower than the saturation concentration (refer to JP 1-318021 A).

The polymerization step in the present invention can be performed at a normal pressure, a reduced pressure, or an increased pressure, but is preferably performed at a normal pressure (or in the vicinity thereof, usually ±10 mmHg). Further, in order to improve the physical properties by accelerating polymerization, during polymerization, a step for degassing dissolved oxygen (for example, a step for replacement with an inert gas) may be provided, as required. Further, the temperature at the time of initiating polymerization depends on the kind of a polymerization initiator used, and is preferably 15° C. to 130° C. and more preferably 20° C. to 120° C.

(Polymerization Initiator)

The polymerization initiator used in the present invention is determined appropriately depending on a polymerization form, and is not particularly limited. Examples thereof include a photodecomposition type polymerization initiator, a thermal decomposition type polymerization initiator, and a redox type polymerization initiator. These polymerization initiators initiate polymerization of the present invention.

Examples of the photodecomposition type polymerization initiator include a benzoin derivative, a benzyl derivative, an acetophenone derivative, a benzophenone derivative, and an azo compound.

Further, examples of the thermal decomposition type polymerization initiator include a persulfate such as sodium persulfate, potassium persulfate, or ammonium persulfate; a peroxide such as hydrogen peroxide, t-butyl peroxide, or methyl ethyl ketone peroxide; and an azo compound such as 2,2'-azobis(2-amidinopropane) dihydrochloride, or 2,2'-azobis[2-(2-imidazolin-2-yl)propane]dihydrochloride.

Furthermore, examples of the redox type polymerization initiator include a system using a reducing compound such as L-ascorbic acid or sodium bisulfite together with the above persulfate or peroxide. It is also preferable to use the above photodecomposition type polymerization initiator and thermal decomposition type polymerization initiator together. Among these polymerization initiators, an azo polymerization initiator to generate $N_2$ by pyrolysis may be used to accelerate foaming. Further, an active energy ray such as an ultraviolet ray, an electron ray, or a γ ray may be used singly or in combination with the above polymerization initiator.

The amount of the polymerization initiator used is preferably 0.0001 mol % to 1 mol % and more preferably 0.0005 mol % to 0.5 mol % with respect to 100 mol % of the monomer. When the amount to use thereof is 1 mol % or less, deterioration of color tone of the water-absorbing resin is suppressed, which is preferable. When the amount to use thereof is 0.5 mol % or less, deterioration of color tone is further suppressed, which is more preferable. Further, when the amount to use thereof is 0.0001 mol % or more, an increase of a residual monomer is suppressed, which is preferable. When the amount to use thereof is 0.0005 mol % or more, an increase of a residual monomer is further suppressed, which is more preferable.

(Adhesion Controlling Agent)

In order to sophisticatedly solve the problem of the present invention, an adhesion controlling agent specifically described in (2-3-2) is added. The adhesion controlling agent may be added before, during, or after the polymerization step, and specifically, is added in the step (iii) or before the step (iii)

(More Preferable Polymerization Method)

In the present invention, as a method for polymerizing a (meth)acrylic acid (salt)-based aqueous monomer solution, from the viewpoint of the physical properties of the water-absorbing resin (for example, water absorption speed or liquid permeability), easiness of controlling polymerization or the like, aqueous solution polymerization is employed. In particular, kneader polymerization or belt polymerization is preferably employed, and continuous aqueous solution polymerization is more preferably employed.

Preferable examples of the aqueous solution polymerization include continuous belt polymerization (disclosed in U.S. Pat. Nos. 4,893,999, 6,241,928, US 2005/215734 A, and the like), continuous kneader polymerization and batch kneader polymerization (disclosed in U.S. Pat. No. 6,987, 151-, U.S. Pat. No. 6,710,141, and the like). Among these aqueous solution polymerizations, in the method described in JP 2002-212204 A, the time for the polymerization step can be shortened by setting the polymerization initiation temperature to a high temperature of 50° C. or higher. Furthermore, the maximum reaching temperature can be suppressed by utilizing evaporative latent heat of water, and as a result, it is possible to obtain a water-absorbing resin in which the main chain molecular weight is high and the molecular weight distribution is narrow, which is particularly preferable.

As an example of the preferred embodiment of the aqueous solution polymerization, the concentration of a monomer in the (meth)acrylic acid (salt)-based aqueous monomer solution is preferably 10 wt % to 80 wt %, more preferably 20 wt % to 60 wt %, and still more preferably 30 wt % to 50 wt %. Incidentally, in Examples of the present application, the monomer concentration was 38 wt % and 39 wt %.

When the monomer concentration is in the above ranges, a load of the machine at the next gel-crushing step does not become excessively high, and the weight average particle diameter of the particulate hydrogel can be efficiently controlled in a desired range.

Furthermore, in order to control GCA and FGBP in a desired range, it is preferable to control the maximum reaching temperature during polymerization. Specifically, the maximum reaching temperature during polymerization is preferably 70° C. to 130° C., more preferably 80° C. to 120° C., and still more preferably 85° C. to 110° C.

Further, in the polymerization, if necessary, a chain transfer agent such as hypophosphorous acid (salt), for example, a chelating agent such as trisodium diethylenetriamine pentaacetate or pentasodium diethylenetriamine pentaacetate, or the like may be further added to a reaction system before or during polymerization in an amount of preferably 0 wt % to 3 wt % and more preferably 0.001 wt % to 1 wt % with respect to 100 wt % of the monomer.

(2-3) Gel-Crushing Step (Step (iii))

This is a step for crushing the crosslinked hydrogel polymer (hereinafter, referred to as "hydrogel" in some cases) obtained through the polymerization step and the like to obtain hydrogel in the state of a particulate (hereinafter, referred to as "hydrogel particles" or "particulate hydrogel" in some cases). By grain refining of the particulate hydrogel by gel-crushing of the hydrogel, particularly by gel-Crushing using kneading up to a specific particle diameter range, GCA and vortex are improved.

Here, from the viewpoint of easiness of gel-crushing and drying of the particulate hydrogel after gel-crushing, solids content of the crosslinked hydrogel polymer is preferably 10 wt % to 80 wt %, more preferably 20 wt % to 70 wt %, still more preferably 20 wt % to 60 wt %, still more preferably 30 wt % to 50 wt %, and particularly preferably 35 wt % to 48 wt %.

When the solids content is less than 10 wt %, the moisture content of the particulate hydrogel after crushing becomes high, and thus energy necessary for drying and drying time are increased too. Therefore, there is a concern in a cost increase and a decrease in production efficiency. In the meantime, when the solids content is more than 80 wt %, the gel is hardened so that a load to the pulverization apparatus is increased. So, there is a concern that the pulverization apparatus may be broken.

Incidentally, a method for adjusting the solids content of the crosslinked hydrogel polymer to 10 wt % to 80 wt % is not particularly limited, but for example, it may be performed by controlling the total amount of monomers during polymerization.

The "weight average particle diameter of the particulate hydrogel (hydrogel particles)" after this gel-crushing step is 100 μm to 900 μm, preferably 120 m to 870 μm, more preferably 130 μm to 860 μm, and still more preferably 140 μm to 850 μm, and may be 150 μm to 800 μm, 160 μm to 700 μm, 170 μm to 600 μm, or 100 μm to 350 μm.

The "weight average particle diameter of the hydrogel particles converted to the dried product" after this gel-crushing step is 50 μm to 650 μm, preferably 80 μm to 640 μm, more preferably 100 μm to 630 μm, still more preferably 110 μm to 600 μm, still more preferably 120 μm to 500 μm, and particularly preferably 130 μm to 460 μm, and may be 140 μm to 400 μm.

Herein, the "weight average particle diameter (RB) of the hydrogel particles converted to the dried product (solids content: 100 wt %)" can be derived by the formula: "the weight average particle diameter (RA) of the hydrogel particles"×"(the solids content of the hydrogel particles)$^{1/3}$."

It is described how to derive such a formula. The volume of the hydrogel particles changes as a similar 16 figure depending on the water absorption amount (fluid retention capacity) thereof and the particle diameter also changes as a similar figure in accordance with the volume change. Herein, the description will be given assuming the hydrogel particles and dried products thereof are spherical.

A volume V of the sphere can be expressed as $(\pi \times R^3)/6$ when the diameter of the sphere is designated as R. Similarly, a volume VA can be expressed as $\{\pi \times (RA)^3\}/6$ when the hydrogel particles are assumed as a sphere. Meanwhile, a volume VB of the dried product can be expressed as $\{\pi \times (RB)^3\}/6$ when the solids content is regarded as 100 wt %. Therefore, the ratio VA:VB can be established as $\{\pi \times (RA)^3\}/6$: $\{\pi \times (RB)^3\}/6$, and $RB = RA \times (VB/VA)^{1/3}$ can be established.

Herein, the volumes VA and VB of the hydrogel particles are proportional to the reciprocal of the solids content. For example, when the solids content of the hydrogel particles is 40 wt %, assuming the solids content of the dried product as 100 wt %, the volume of the hydrogel particles is 2.5 times (=100/40).

When the solids content of the hydrogel particles is designated as SA and the solids content of the dried product (of the hydrogel particles) is designated as SB, the ratio VA:VB can be expressed as (1/SA): (1/SB). Therefore, when each of 1/SA and 1/SB is used for calculation instead of VA and VB in the aforementioned $RB = RA \times (VB/VA)^{1/3}$, the following equation can be established: $RB = RA \times (SA/SB)^{1/3}$. Herein, when SB is 100, the following equation can be derived: $RB = RA \times (SA/100)^{1/3}$.

For example, specifically, when 40 wt % (solids content) of the gel is crushed, 100 μm to 900 μm of the particulate hydrogel is calculated as 74 μm to 663 μm converted to the dried product.

(Gel-Crusher)

In the present invention, it is important that the weight average particle diameter of the particulate hydrogel (hydrogel particles) is controlled to the above-mentioned range, and a means for achieving them is not particularly limited. Examples thereof include a batch type or continuous type double-arm kneader, a gel-crusher provided with a plurality of rotary stirring blades, a uniaxial extruder, a biaxial extruder, a meat chopper or the like. In particular, a screw extruder (for example, a meat chopper) having a porous plate at an end thereof is preferable, which includes a screw extruder disclosed in JP 2000-063527 A, for example.

In particular, the gel-crusher used in this step is more preferably a screw extruder, and still more preferably a screw extruder (for example, a meat chopper) having a porous plate at one end of a casing. For example, screw extruders disclosed in JP 2000-63527 A, WO 2015/030129 A, and WO 2015/030130 A are exemplified. Hereinafter, an example of a screw extruder used in this step is described. The same apparatus is also used in these Examples, A screw extruder for use in the present step is constituted by, for example, a casing, a table, a screw, a feed orifice, a hopper, a discharge orifice, a porous plate, a rotary blade, a ring, a backflow preventer, a motor, a ridge, and/or the like. The casing is in the form of a cylinder and has the screw therein. The casing has the discharge orifice at one end thereof, through which the crosslinked hydrogel polymer is extruded and subjected to gel-crushing, and has the porous plate placed short of the discharge orifice. The casing has, at the other end, the motor and a drive system and the like for rotation of the screw. There is the table under the casing and thereby the screw extruder can sit stably. The casing has, on the other hand, the feed orifice at the top thereof, through which the crosslinked hydrogel polymer is fed. The feed orifice is provided with the hopper for easy feeding of the crosslinked hydrogel polymer. The shape and size of the casing are not particularly limited, provided that the casing has an inner surface in the form of a cylinder that corresponds to the shape of the screw. The speed of the screw varies depending on the shape of the screw extruder and is not particularly limited, but is preferably adjustable as is described later. Furthermore, for example, the screw extruder may include the backflow preventer near the discharge orifice and may have the ridge on the screw. The arrangements of these components, materials for these components, sizes of these components, materials for the backflow preventer and the rotary blades attached to the screw, and all other arrangements related to the screw extruder may be determined in accordance with the method disclosed in the above-mentioned Japanese Patent Application Publication, Tokukai, No. 2000-63527, WO 2015/030129 A, and WO 2015/030130.

For example, the backflow preventer is not limited to a particular kind, provided that the backflow of the crosslinked hydrogel polymer at or near the discharge orifice is prevented by the structure of the backflow preventer. The backflow preventer is, for example, a ridge in the form of a spiral or ridges in the form of concentric circles on the inner wall of the casing, a linear, particulate, spherical, or angular projection parallel to the screw, or the like. When the pressure at or near the discharge orifice increases as the gel-crushing proceeds, the crosslinked hydrogel polymer tries to flow back toward the feed orifice. Providing the backflow preventer makes it possible to prevent the backflow of the crosslinked hydrogel polymer while performing gel-crushing of the crosslinked hydrogel polymer.

In the present invention, the particle diameter after gel-crushing is significantly small. A method for adjusting the particle diameter in this way is not particularly limited, but in the case of using a screw extruder in which a porous plate is provided at one edge of the casing, it is necessary to change the size of the device according to the amount of the crosslinked hydrogel polymer to be subjected to gel-crushing treatment. At this time, it is possible to adjust the size of the device by appropriately adjusting a thickness of the porous plate, a pore diameter of the porous plate, an open area of the porous plate, the rotation speed of a screw axis, a feed rate of the crosslinked hydrogel polymer, and the like in accordance with an apparatus to be used.

In regard to the porous plate at the exit of the casing of the gel-crusher, the thickness, pore diameter, and the open area of the porous plate may be selected as appropriate depending on the volume per unit time of the crosslinked hydrogel polymer crushed by the gel-crusher, the properties of the crosslinked hydrogel polymer, and the like and are not particularly limited. The thickness of the porous plate is preferably in a range of 3.5 mm to 100 mm and more preferably in a range of 6 mm to 80 mm. The diameter is preferably 30 mm to 1,500 mm and more preferably 40 mm to 1,000 mm.

Further, the pore diameter of the porous plate is preferably in a range of 1.0 mm to 50 mm and more preferably in a range of 2.0 mm to 30 mm.

Furthermore, the open area of the porous plate is preferably in a range of 10% to 80%, more preferably in a range of 20% to 60%, and still more preferably in a range of 25% to 55%.

Further, the number of pores is preferably 10 to 2,000 and more preferably 20 to 1,000.

It is noted that, in a case where a plurality of porous plates having different pore diameters (mm) are used, the simple average of the pore diameters of the porous plates is used as the pore diameter of the porous plates of the gel-crusher. The shape of the pore is preferably a, circle. In a case where the shape of the pore is a shape other than a circle, such as a square, an oval, a slit, or the like, the area of the pore is converted into the area of a circle and this diameter of the circle is used as a pore diameter (mm).

Further, the outer diameter of the screw axis is preferably 10 mm to 2,000 mm and more preferably 20 mm to 1,000 mm.

Further, the feed rate of the crosslinked hydrogel polymer is preferably 0.10 kg/min to 550 kg/min and more preferably 0.12 kg/min to 500 kg/min.

If the thickness of the porous plate is less than 3.5 mm, the pore diameter of the porous plate is more than 50 mm, and/or the open area of the porous plate is more than 80%, there is a case where the crosslinked hydrogel polymer cannot be gel-crushed to particulate hydrogel having a desired particle diameter. On the contrary, if the thickness of the porous plate is more than 100 mm, the pore diameter of the porous plate is less than 1.0 mm, and/or the open area of the porous plate is less than 10%, such a porous plate may apply excessive shearing and compressive forces to the crosslinked hydrogel polymer, resulting in a reduction in physical properties of the crosslinked hydrogel polymer.

When the feed rate of the crosslinked hydrogel polymer is 0.10 kg/min or less, excessive shearing stress and compressive force are applied to the crosslinked hydrogel polymer so that physical properties may be deteriorated. On the other hand, when the feed rate of the crosslinked hydrogel polymer is more than 550 kg, there is a case where the crosslinked hydrogel polymer cannot be gel-crushed to particulate hydrogel having a desired particle diameter.

Further, as described above, according to the present invention, the particle diameter after gel-crushing is significantly small. A method for adjusting the particle diameter in this way is not particularly limited, but the method may be performed by setting gel grinding energy to an appropriate value.

The gel grinding energy (GGE (1)) is preferably 10 J/g to 500 J/g, more preferably 15 J/g to 400 J/g, still more preferably 20 J/g to 300 J/g, still more preferably 45 J/g to 250 J/g, and particularly preferably 25 J/g to 200 J/g.

In a case where the gel grinding energy (GGE (1)) is less than 10 J/g, there is a case where the crosslinked hydrogel polymer cannot be gel-crushed to particulate hydrogel having a desired particle diameter. On the other hand, in a case where the gel grinding energy (GGE (1)) is more than 500 J/g, a load to a pulverization apparatus becomes large so that there is a concern that the pulverization apparatus may be broken in a continuous operation. Moreover, excessive shearing stress and compressive force are applied to the crosslinked hydrogel polymer so that the amount of the water soluble component produced may be increased or deterioration of physical properties such as a decrease in CRC and AAP may occur.

The gel grinding energy (GGE (2)) is preferably 5 J/g to 300 J/g, more preferably 6 J/g to 280 J/g, still more preferably 8 J/g to 260 J/g, still more preferably 9 J/g to 250 J/g, and still more preferably 10 J/g to 240 J/g.

In a case where the gel grinding energy (GGE (2)) is less than 5 J/g, there is a case where the crosslinked hydrogel polymer cannot be gel-crushed to particulate hydrogel having a desired particle diameter. On the other hand, in a case where the gel grinding energy (GGE (2)) is more than 300 J/g, excessive shearing stress and compressive force are applied to the crosslinked hydrogel polymer so that the amount of the water soluble component produced may be increased or deterioration of physical properties such as a decrease in CRC and AAP may occur.

Incidentally, in a case where pulverization is performed multiple times, GGE is obtained by adding the gel grinding energy at the time of each pulverization.

GGE Calculation Method

"Gel Grinding Energy" (GGE (1), GGE (2))

In an embodiment of the present invention, the term "gel grinding energy" denotes mechanical energy per unit weight (unit weight of a crosslinked hydrogel polymer) required for a gel-crusher to crush the crosslinked hydrogel polymer. It is noted that the "gel grinding energy" does not include energy to heat or cool a jacket or energy of introduced water or steam. It is noted that the "gel grinding energy" is referred to as "GGE(1)" for short. The GGE is calculated using the following Equation (1) in a case where a gel-crusher is driven by three-phase electric power.

[Mathematical Formula 1]

$$\text{GGE (1)}[J/g] = \{\sqrt{3} \times \text{voltage} \times \text{current value during gel-crushing} \times \text{power factor} \times \text{motor efficiency}\} / \{\text{weight of crosslinked hydrogel polymer fed into gel-crusher per second}\} \quad \text{(Equation 1)}$$

In the equation, the "power factor" and the "motor efficiency" are values inherent to the gel-crusher and vary depending on operation conditions and the like of the gel-crusher, and may have a value of 0 to 1. It is possible to know the characteristic values by inquiring them from a manufacturer of the device or the like. In a case where the gel-crusher is driven by single-phase electric power, the GGE can be calculated using a modified equation where "$\sqrt{3}$" in the above equation is changed to "1". In the equation, the unit of voltage is [V], the unit of current is [A], and the unit of weight of the crosslinked hydrogel polymer is [g/s].

The mechanical energy applied to a crosslinked hydrogel polymer is important in an embodiment of the present invention. Therefore, it is preferable that the gel grinding energy be calculated excluding the value of current flowing while the gel-crusher is in the idle state. Especially in a case where a plurality of gel-crushers are used to crush gel, the total value of current during the idle state is large and thus a calculation excluding the values of current during the idle state is preferred. The gel grinding energy in this case is calculated using the following Equation (2). It is noted that, for distinction from the above-described GGE(1), the gel grinding energy calculated using the following Equation (2) is represented as GGE (2).

[Mathematical Formula 2]

GGE (2)[J/g]={($\sqrt{3}$×voltage×(current value during gel-crushing−current value during idle state)× power factor×motor efficiency}/{weight of crosslinked hydrogel polymer fed into gel-crusher per second} (Equation 2)

According to the preferred embodiment of the present invention, the crosslinked hydrogel polymer is gel-crushed to obtain hydrogel particles, the hydrogel particles are dried to obtain a dried product, and then the dried product is "pulverized." In this way, since "pulverization" is performed at the subsequent step, it is considered that it is not necessary to take the trouble to pulverize the "crosslinked hydrogel polymer," which is difficult to pulverize, multiple times or to decrease the particle diameter after gel-crushing to be significantly small by setting the gel grinding energy to more than a predetermined degree.

In this regard, the present invention can provide a poly(meth)acrylic acid (salt)-based particulate water-absorbing agent enabling reduction in re-wet amount and having an excellent speed of incorporating liquid and a production method therefor by employing a unique configuration in which the particle diameter after gel-crushing is adjusted to be significantly small and an adhesion controlling agent is used.

(Gel-Cutting or Gel-Grinding Before Gel Crushing)

In a case where the polymerization step is performed by belt polymerization, a crosslinked hydrogel polymer may be chopped or broken during or after polymerization, preferably after polymerization, to a size of about several tens of centimeters prior to the gel-crushing. Herein, gel-cutting or gel-grinding is a primary treatment performing cutting or grinding in such a size that the cut or ground product can be continuously supplied to a crusher (for example, a primary treatment of 1,000 cm$^3$ or less or 1,000 cm$^2$ or less in plane). On the other hand, gel-crushing is different from gel-cutting or gel-grinding in that fine granulating is performed (particularly, fine granulating to have a weight average particle diameter of 50 micron to 650 micron converted to the dried product).

This operation makes it easily to feed the crosslinked hydrogel polymer into the gel-crusher and thus possible to more smoothly perform the gel-crushing step. It is noted that the chopping or breaking is preferably performed by a method that enables chopping or breaking of the crosslinked hydrogel polymer without kneading the crosslinked hydrogel polymer, and is, for example, chopping or breaking or the like using a guillotine cutter. The size and shape of the chopped or broken crosslinked hydrogel polymer are not particularly limited, provided that the crosslinked hydrogel polymer can be fed into the gel-crusher, but as for the shape, a block shape is preferable.

(Polymerization Rate of Crosslinked Hydrogel Polymer Before Gel-Crushing)

The gel-crushing in the present invention is performed during polymerization and/or after polymerization and is preferably performed on the crosslinked hydrogel polymer after polymerization. Incidentally, as polymerization in which gel-crushing is performed during polymerization, kneader polymerization is exemplified, but gel-crushing may be performed further after polymerization. Further, as polymerization in which gel-crushing is performed after polymerization, belt polymerization or stand-still aqueous solution polymerization (aqueous solution polymerization under substantially no stirring) in a tank is preferably exemplified, but polymerization is not particularly limited to these polymerization examples.

The polymerization rate of the crosslinked hydrogel polymer to be subjected to gel-crushing is preferably 90 mol % or more, more preferably 93 mol % or more, even more preferably 95 mol % or more, particularly preferably 97 mol % or more. The upper limit is preferably 99.5 mol %. The crosslinked hydrogel polymer to be subjected to gel-crushing having a polymerization rate of 90 mol % or more is preferred, because residual monomers contained in the resulting water-absorbing resin become small in number. Incidentally, also in a case where gel-crushing is performed during polymerization, it is only necessary to continue polymerization as described below until the above-described polymerization rate is attained. As used herein, the polymerization rate, which is also referred to as conversion rate, means a value calculated from polymer content of the crosslinked hydrogel polymer and unreacted monomer content.

The polymerization rate of the crosslinked hydrogel polymer to be subjected to gel-crushing preferably falls within the above range. However, in a case where gel-crushing is performed during polymerization, such as performing kneader polymerization, it is assumed that the gel-crushing step starts when the aqueous monomer solution has turned into a "sufficiently gelled state".

For example, in a case where the kneader polymerization is employed, the aqueous monomer solution changes into a crosslinked hydrogel polymer as polymerization progresses. Specifically, an aqueous monomer solution is stirred at the initiation of polymerization, a crosslinked hydrogel polymer having a certain viscosity and a low degree of polymerization is stirred during polymerization, gel-crushing of part of the crosslinked hydrogel polymer starts as the polymerization progresses, and gel-crushing is performed in the last half or in the final stage of the polymerization, sequentially in a single region. Therefore, for clear distinction between "stirring of an aqueous monomer solution" at the initiation of the polymerization and "gel-crushing" in the final stage of the polymerization, it is judged that a transition to the gel-crushing step has occurred when the "sufficiently gelled state" is reached.

The term "sufficiently gelled state" denotes a state in which the crosslinked hydrogel polymer can be grain-refined by applying shearing force and which occurs when or after the maximum polymerization temperature (polymerization peak temperature) is reached. The term "sufficiently gelled state" also denotes a state in which the crosslinked hydrogel polymer can be grain-refined by applying shearing force and which occurs when or after the polymerization rate of monomers in the aqueous monomer solution reaches preferably 90 mol % or more, more preferably 93, mol % or more, even more preferably 95 mol % or more, particularly preferably 97 mol % or more. That is, in the gel-crushing step of an embodiment of the present invention, a crosslinked hydrogel polymer having a monomer polymerization rate falling within the above range is preferably subjected to the gel-crushing. It is noted that, in a case of a polymerization reaction that shows no polymerization peak temperature (for example, in a case where entire polymerization proceeds at constant temperature, a case where the polymerization temperature continues to rise, or the like), "sufficiently gelled state" is determined on the basis of the fact that the polymerization rate of the monomers becomes preferably 90 mol % or more, more preferably 93 mol % or more, still more preferably 95 mol % or more, and particularly preferably 97 mol % or more.

(Operating Conditions of Gel-Crusher)

In a case where the gel-crusher for use in the gel-crushing step of an embodiment of the present invention is a screw extruder (for example, a meat chopper), the rotation speed of a screw shaft of the screw extruder cannot be specified by a particular value because the peripheral speed of the impeller blades varies depending on the inner diameter of the casing of the screw extruder, the outer diameter of the screw axis, and the like. The shaft rotation speed is preferably 80 rpm to 500 rpm, more preferably 90 rpm to 400 μm, even more preferably 100 rpm to 300 rpm.

Incidentally, the inner diameter of the casing is suitably about 15 mm to 2,500 mm and more suitably about 25 mm to 1,500 mm.

In a case where the shaft rotation speed is 80 rpm or more, shearing and compressing forces necessary for gel-crushing are achieved. In a case where the shaft rotation speed is 500 rpm or less, the shearing and compressive forces applied to the crosslinked hydrogel polymer are not excessive and therefore physical properties are not likely to deteriorate, and the gel-crusher does not experience large load and thus is not prone to breakage of the device.

Meanwhile, in a case where the rotation speed of the axis is less than 80 rpm, shearing stress and compressive force required for the gel-crushing are difficult to obtain. In a case where the rotation speed of the axis is more than 500 rpm, shearing stress and compressive force to be applied to the crosslinked hydrogel polymer become excessive. This deteriorates the physical properties and increases load on the gel-crusher thereby damaging the device.

Further, the rate of a periphery of a rotational blade at this time is preferably 0.5 m/s to 10 m/s and more preferably 0.5 m/s to 8 m/s.

Further, the gel-crusher in the present invention is heated or kept to have a temperature preferably in a range of 30° C. to 120° C. and more preferably 40° C. to 100° C. so as to prevent the crosslinked hydrogel polymer from adhering thereto.

Further, the temperature of the gel-crusher in the present invention is also suitably set to be in a temperature range of the gel temperature described below.

(Number of Times of Gel-Crushing Treatment)

In the present invention, the number of times of the gel-crushing treatment is not particularly limited as long as the particle diameter after gel-crushing is significantly small, but according to an embodiment of the present invention, the number of times of the gel-crushing treatment is multiple times.

In a case where the gel-crushing is performed multiple times, a method in which treatment is performed multiple times with use of one gel-crusher may be employed or treatment may be continuously performed by disposing a plurality of gel-crushers in series. By performing the gel-crushing multiple times, the weight average particle diameter of the particulate hydrogel can be adjusted in a desired range by gel-crushing under relatively mild conditions, the physical properties of the water-absorbing resin are less likely to degrade, and a load applied to a gel-crusher is small so that there is no concern that the device is damaged.

Gel-crushers in the case of performing the treatment multiple times do not need to be the same type of machine, and different types of machine may be combined, or even in the same type of machine, setting condition and operation conditions may be changed.

Therefore, according to the preferred embodiment of the present invention, the gel-crushing step is performed with use of a plurality of gel-crushers. According to such an embodiment, the technical effect of lowering a load applied to one crusher is achieved.

The preferable number of times of treatment in the case of performing the treatment multiple times is preferably 2 to 5 times, more preferably 2 to 4 times, and still more preferably 2 to 3 times. Incidentally, performing the gel-crushing twice indicates that hydrogel particles discharged from a discharge port of a gel-crusher are introduced again into the gel-crusher and then the gel-crushing is performed. The same applies to the case of performing the gel-crushing three or more times.

Further, if the particle diameter after gel-crushing is significantly small, it is sufficient to perform the gel-crushing once. In the case of performing the gel-crushing once, costs of introduction and maintenance of a gel-crusher are suppressed and space for production facility is also suppressed. Further, energy burden can be reduced, which is preferable.

(Gel Temperature)

Gel temperature, specifically, the temperature of a crosslinked hydrogel polymer that has not been subjected to gel-crushing, is preferably 40° C. to 120° C., more preferably 50° C. to 120° C., even more preferably 52° C. to 110° C., even more preferably 48° C. to 80° C., particularly preferably 56° C. to 70° C., from the viewpoint of particle size control and physical properties. Incidentally, the gel temperature may be 65° C. to 110° C.

Further, the numerical value of the gel temperature may be applied to the temperature of the gel-crusher.

In a case where the gel temperature is lower than 40° C., in terms of the characteristics of the crosslinked hydrogel polymer, adherability becomes relatively high. Thus, it is difficult to control the particle shape and the particle size distribution during gel-crushing. Further, in a case where gel temperature is higher than 120° C., evaporation of water from the gel becomes significant so that the solids content of the hydrogel is changed. This makes the crushing difficult. Thus, it is difficult to control the particle diameter and the particle shape of the particulate hydrogel. Such a gel temperature can be appropriately controlled by the polymerization temperature, heating, warming, or cooling after polymerization, and the like.

(Gel CRC)

The gel CRC of a crosslinked hydrogel polymer that has not been subjected to gel-crushing and the particulate hydrogel (hydrogel particles) after gel-rushing are preferably one of the values is 25 g/g to 50 g/g, and more preferably, both values are 25 g/g to 50 g/g, more preferably 26 g/g to 45 g/g, and still more preferably 27 g/g to 40 g/g. In a case where the gel CRC is in the above ranges, particle shape and particle size distribution are easy to control when gel-crushing is performed, and thus such a case is preferred. Such a gel CRC can be appropriately controlled by the amount of a crosslinking agent added during polymerization and other parameters such as polymerization concentration. It is noted that it is well known that a water absorbent resin having a high CRC is preferred. However, in a case where the gel CRC exceeds the above range, in some cases, it may be difficult to control the particle shape and the particle size distribution.

In a case where there in a change between CRC of the crosslinked hydrogel polymer before gel-crushing and CRC of the hydrogel particles after gel-crushing, the change in CRC in the gel-crushing step in which the crosslinked hydrogel polymer is crushed to obtain hydrogel particles (a value obtained by subtracting CRC of the hydrogel particles after gel-crushing from CRC of the crosslinked hydrogel polymer before gel-crushing, unit is g/g) is preferably −10 to +10, more preferably −8 to +8, still more preferably −6 to +6, particularly preferably −5 to +5, and most preferably −4 to +4.

When the change in CRC becomes larger than −10 and CRC of the resulting hydrogel particles becomes small, it is difficult to adjust CRC in the drying step. When the change in CRC becomes larger than +10, damage to the gel in the gel-crushing step is increased to increase the eluted component. Thus, there is a concern that GCA and FGBP of the water-absorbing agent are lowered.

The gel CRC of the crosslinked hydrogel polymer is determined by the measurement method which is described later in section of [Examples], after cutting and grain-refining the crosslinked hydrogel polymer that has not been subjected to gel-crushing into pieces 1 mm to 3 mm on a side with the use of scissors, a cutter, or the like. And, the gel CRC of the particulate hydrogel (hydrogel particles) after gel-crushing is determined by the measurement method which is described later in section of [Examples] without being cut or fragmented by the measurement method that is described in [Examples] described later.

(Solids Content of Resin Before and after Gel-Crushing)

In the present invention, from the viewpoint of physical properties, the solids content of the resin of the crosslinked hydrogel polymer before gel-crushing is preferably 10 wt % to 80 wt %, more preferably 20 wt % to 60 wt %, still more preferably 30 wt % to 55 wt %, still more preferably 33 wt % to 50 wt %, and particularly preferably 36 wt % to 46 wt %.

In the present invention, from the viewpoint of physical properties, the solids content of the resin of the particulate hydrogel (hydrogel particles) after gel-crushing is 10 wt % to 80 wt %, preferably 20 wt % to 60 wt %, more preferably 30 wt % to 55 wt %, still more preferably 33 wt % to 50 wt %, and still more preferably 36 wt % to 46 wt %.

By adjusting the solids content of the resin of the particulate hydrogel (hydrogel particles) after gel-crushing in the above range, preferably, by adjusting the solids content of the resin of the crosslinked hydrogel polymer before gel-crushing in the above range, damage (an increase in water soluble component, or the like) caused by drying is decreased.

Incidentally, the solids content of the resin of the hydrogel particles after gel-crushing can be appropriately controlled, if necessary, by adding water before gel-crushing or during gel-crushing, by evaporating moisture by heating during gel-crushing, or the like.

In a case where there is a change in solids content between the crosslinked hydrogel polymer before gel-crushing and the hydrogel particles after gel-crushing, the change in solids content in the gel-crushing step in which the crosslinked hydrogel polymer is crushed to obtain hydrogel particles (a value obtained by subtracting the solids content of the hydrogel particles after gel-crushing from the solids content of the crosslinked hydrogel polymer before gel-crushing, unit is wt %) is preferably −10 to +10, more preferably −8 to +8, still more preferably −6 to +6, particularly preferably −5 to +5, and most preferably −4 to +4. Herein, the minus symbol means that the solids content is decreased (the moisture content is increased), and plus (+) symbol means that the solids content is increased (the moisture content is decreased).

When the change in solids content becomes larger than −10, a load to the drying step is increased by an increase in the moisture content of the hydrogel particles. This makes sufficient drying difficult or a larger quantity of thermal energy necessary. That is, the production efficiency is degraded.

When the change in solids content becomes larger than +10, damage to the gel in the gel-crushing step is increased to increase the eluted component. Thus, there is a concern that GCA and FGBP of the water-absorbing agent are lowered.

(Use of Water)

In the gel-crushing step of an embodiment of the present invention, water may be added to a crosslinked hydrogel polymer before subjecting the crosslinked hydrogel polymer to gel-crushing. It is assumed in an embodiment of the present invention that "water" includes at least one of the solid, liquid, and gaseous forms.

How and when water is added are not particularly limited, provided that water is fed to the gel-crusher while a crosslinked hydrogel polymer resides in the gel-crusher. Alternatively, a crosslinked hydrogel polymer to which water has been added may be fed into the gel-crusher. Furthermore, the water is not limited to "water alone" and may be in the form of a mixture of water and another additive (for example, surfactant, base for neutralization) or a solvent other than water. However, in this case, the water content is preferably 90 weight % to 100 weight %, more preferably 99 weight % to 100 weight %, even more preferably substantially 100 weight %.

In an embodiment of the present invention, the water in at least one of the solid, liquid, and gaseous forms may be used, but the water in liquid and/or gaseous form is preferred from the viewpoint of handleability. The amount of water fed is preferably 0 parts by weight to 4 parts by weight or less, more preferably 0 parts by weight to 2 parts by weight or less, relative to 100 parts by weight of the crosslinked hydrogel polymer. In a case where the amount of the water fed is more than 4 parts by weight, this may cause some problems such as undried materials left undried even after drying.

In a case where the water is fed in liquid form, the temperature of the water when fed is preferably 10° C. to 100° C., more preferably 40° C. to 100° C. The water in the form of liquid is appropriately added by means of spray, mist, showering, droplet, a straight pipe, or the like. In a case where the water is fed in gaseous form, the temperature of the water fed is preferably 100° C. to 220°, more preferably 100° C. to 160° C., even more preferably 100° C. to 130° C. It is noted that, when water is fed in gaseous form, a method of preparing the water in gaseous form is not particularly limited. The water in gaseous form may be prepared by, for example: a method using water vapor generated from heat made by a boiler; a method using water in gaseous form released from the surface of water ultrasonically vibrated; or the like. In an embodiment of the present invention, in a case where water is fed in gaseous form, the water is preferably water vapor with higher pressure than atmospheric pressure, more preferably water vapor generated by a boiler.

In order to solve the problem of the present invention, it is preferable to employ aqueous solution polymerization rather than reverse phase suspension polymerization in which gel-crushing is not necessary, and it is particularly preferable to employ aqueous solution polymerization in which gel-crushing is performed during polymerization (for example, kneader polymerization) or after polymerization (for example, belt polymerization and further, if necessary, kneader polymerization).

(2-3-2) Addition of Adhesion Controlling Agent

In order to more sophisticatedly solve the problem of the present invention, the gel contains an adhesion controlling agent during gel-crushing. In other words, it is sufficient to add an adhesion controlling agent before the gel-crushing is completely finished. For doing this, an adhesion controlling agent is added in at least one step of the step (i): the step for preparing a (meth)acrylic acid (salt)-based aqueous monomer solution, the step (ii): the polymerization step, and the step (iii): the gel-crushing step, or an adding step may be provided between the step (i) and the step (ii) or between the step (ii) and the step (iii). As a step performed between the step (i) and the step (ii), for example, a step for storing and transporting the prepared (meth)acrylic acid (salt)-based aqueous monomer solution is exemplified, and as a step performed between the step (ii) and the step (iii), for example, a step for aging a hydrogel-like polymer is exemplified. In this way, by containing an adhesion controlling agent in the inside and/or the surface of the hydrogel particles in the step (iii) or before the step (iii), the desired effect of the present invention can be exerted.

Further, the step (iii) is a step for gel-crushing the crosslinked hydrogel polymer during polymerization or after polymerization to obtain hydrogel particles. However, adding an adhesion controlling agent to "the crosslinked hydrogel polymer" before performing gel-crushing or "a product obtained by cutting or grinding the crosslinked hydrogel polymer" is also encompassed in the concept of "adding an adhesion controlling agent in the step (iii)."

The adhesion controlling agent may be in the form of liquid or solid, and may be added without any change or may be added in a state of a solution or a suspension.

Further, when the adhesion controlling agent is a radically polymerizable adhesion controlling agent having an unsaturated bond, in the case of adding the radically polymerizable adhesion controlling agent in the step (i) or the step (ii), the radically polymerizable adhesion controlling agent may be consumed by reaction during polymerization so that the radically polymerizable adhesion controlling agent may not remain. Furthermore, in the case of addition in the step (iii), the radically polymerizable adhesion controlling agent may not be sufficiently consumed to remain in a final product, which causes coloration. Thus, the adhesion controlling agent is preferably non-radically polymerizable.

In the case of adding the adhesion controlling agent in the state of a solution or, in the case of adding the adhesion controlling agent in the state of a suspension, a solvent and a dispersion medium are not particularly limited, but water or alcohol is preferable and water is particularly preferable.

The concentration of the adhesion controlling agent in the case of addition in the state of a solution or a suspension is preferably 0.1 wt % to 99 wt %, more preferably 0.1 wt % to 75 wt %, and still more preferably 0.1 wt % to 50 wt %.

The temperature when the adhesion controlling agent is added in the state of a solution is a melting point or higher and boiling point or lower, and further, is used at 0° C. to 100'C and 20° C. to 50° C. For improving solubility, if necessary, it may be heated.

(Amount of Adhesion Controlling Agent Added)

The amount of the adhesion controlling agent added is not particularly limited, and may be determined in consideration of the type of the adhesion controlling agent.

Although depending on the type of the adhesion controlling agent, the amount of the adhesion controlling agent added is preferably 0.01 wt % to 5 wt %, more preferably 0.02 wt % to 3 wt %, and still more preferably 0.03 wt % to 2 wt % with respect to the raw material monomer of the crosslinked hydrogel polymer.

Incidentally, when the adhesion controlling agent is added in the step (iii), the amount of the adhesion controlling agent added is regarded as the amount of the adhesion controlling agent added with respect to the raw material monomer and the raw material monomer is not the remaining raw material monomer but the raw material monomer used in the step (i) for preparing.

Therefore, according to the preferred embodiment of the present invention, the amount of the adhesion controlling agent added is 0.01 wt % to 5 wt % with respect to the raw material monomer of the crosslinked hydrogel polymer. When the addition amount is less than these lower limits, the adhesion control effect is difficult to confirm. When the addition amount is more than these upper limits, improvement in the adhesion prevention effect does not match with the addition amount, which is not economical.

The amounts of (a) the polyol and (b-1) the glycidyl-modified polyol, which is described below, added may be in the above range of the amount of the adhesion controlling agent added with respect to the raw material monomer of the crosslinked hydrogel polymer, but are preferably 0.01 wt % to 5 wt %, more preferably 0.02 wt % to 3 wt %, still more preferably 0.03 wt % to 2 wt %, still more preferably 0.1 wt % to 1.8 wt %, and particularly preferably 0.2 wt % to 1.5 wt %.

When the addition amount is less than these lower limits, the adhesion control effect is difficult to confirm. When the addition amount is more than these upper limits, improvement in the adhesion prevention effect does not match with the addition amount, which is not economical.

Further, the amounts of (b-2) the alkylene oxide adduct of higher alcohol, (b-3) the alkylene oxide adduct of the polyhydric alcohol fatty acid ester, (c) side-chain and/or terminal polyether-modified polysiloxane, (d) the alkylene oxide adduct of higher aliphatic amine, (e) the alkylaminobetaine, (f) the alkylamine oxide, (g) the sulfuric acid ester salt of the higher alcohol alkylene oxide adduct, (h) the alkyl diphenyl ether sulfonate, and (i) the ammonium salt, which is described below, added may be in the above range of the amount of the adhesion controlling agent added with respect to the crosslinked hydrogel polymer, but is preferably 0.01 wt % to 5 wt %, more preferably 0.01 wt % to 2 wt %, still more preferably 0.01 wt % to 1 wt %, and particularly preferably 0.01 wt % to 0.5 wt %.

When the addition amount is less than these lower limits, the adhesion control effect is difficult to confirm. When the addition amount is more than these upper limits, improvement in the adhesion prevention effect does not match with the addition amount, which is not economical.

Incidentally, in this Example, the raw material monomer is acrylic acid and sodium acrylate.

The adhesion controlling agent described in the present invention is present on the surface of the crosslinked hydrogel polymer and/or the hydrogel particles during gel-crushing, therefore the adhesion controlling agent is an agent capable of lowering adhesion between gel-crosslinked hydrogel polymers, between hydrogel particles, or between dried products adhesion between a crosslinked hydrogel polymer and hydrogel particles; or adhesion between hydrogel particles and a dried product after gel-crushing or after drying.

As an index of adhesion lowering, as compared to a case where the adhesion controlling agent is not added and a case where the water-absorbing resin powder after gel-crushing have the same particle size (water-absorbing resin powder passing through a sieve having a mesh size of 500 μm and not passing through a sieve having a mesh size of 425 μm), it appeared that the BET specific surface area is increased, or the vortex is shortened by 3 seconds or longer, more preferably 5 seconds or longer, and still more preferably 7 seconds or longer. In this Example, comparison is carried out with "the same particle size."

As described below in (2-4) the drying step, in the present invention, it is preferable that the weight average particle diameter of the water-absorbing agent be smaller than the weight average particle diameter of the hydrogel particles after gel-crushing so that the shape in which primary particles are granulated more often appears in the resulting water-absorbing agent. That is, each particle of the primary particles is in loosely contact with each other (the contact area is relatively small). Therefore, the surface area can be increased so that desired physical properties can be achieved.

On the other hand, in a case where the adhesion controlling agent is not added, since adhesion cannot be lowered, granulation excessively proceeds so that particles are difficult to exist as primary particles, and thus desired physical properties are difficult to achieve.

The value obtained by dividing the weight average particle diameter of the water-absorbing agent by the weight average particle diameter of the hydrogel particles after gel-crushing converted to the dried product is preferably 0.40 to 10.0, more preferably 0.45 to 5.0, and still more preferably 0.50 to 4.0.

The hydrogel particles obtained by adding an adhesion controlling agent improves slippage by controlling adhesion between the hydrogel particles. For this reason, the hydrogel particles undergoing through the gel-crushing step is easy to flow in a drier, the treatment amount can be increased, and productivity can be improved. Further, when the gel is easy to flow, thickness unevenness in the drier is lowered, dry unevenness during drying is lowered, and the physical properties of the resulting dried product are stable. Thus, it is more preferable to use an adhesion controlling agent.

When the strength of the gel-dried product obtained through the drying step (iv) is too high, in the pulverizing step of the dried product using a crusher of the pulverizing and classification steps (step v), a large load is applied to the crusher so that the lifespan of the device may be shortened. For this reason, a lower strength of the dried product is preferable. Since the dried product of the hydrogel particles produced by adding an adhesion controlling agent can also control adhesion between water-absorbing resin powders, the strength of the dried product of the hydrogel particles can be lowered. Also, from this reason, it is preferable to use an adhesion controlling agent.

This adhesion controlling agent is an additive that suppresses excessive adhesion between particles (also referred to as primary particles) that constitute granulated shaped particles. In other words, appropriate adhesion between primary particles occurs to perform granulation. As a result of appropriate granulation of the primary particles, the adhesion controlling agent may be present in the inside of the water-absorbing agent (granulated shaped particles) as well as in the vicinity of the surface thereof.

Whether the adhesion controlling agent is present in the vicinity of the surface of the particle or in the inside thereof may be confirmed by analyzing the cut surface of the water-absorbing agent particle to find out distribution of the adhesion controlling agent or by polishing the water-absorbing agent particle by a polishing method or a sputtering method to find out a change in the amount of the adhesion controlling agent component contained. At this time, as for the number of particles to be analyzed, it is preferable that 10 or more particles be arbitrary taken out from particles near the weight average particle diameter and evaluation be carried out with an average value of the analysis value. The inside described herein indicates a portion having a depth of 50 μm or more from the surface of the water-absorbing agent particle.

According to the preferred embodiment of the present invention, the adhesion controlling agent is one or more compounds selected from a nonionic substance, an amphoteric substance, an anionic substance, and a cationic substance, and the nonionic substance is (a) a polyol, (b) a hydroxy group-modified product of a polyol, (c) side-chain and/or terminal polyether-modified polysiloxane, or (d) an alkylene oxide adduct of higher aliphatic amine, the amphoteric substance is (e) alkylaminobetaine or (f) alkylamine oxide, the anionic substance is (g) a sulfuric acid ester salt of a higher alcohol alkylene oxide adduct or (h) alkyl diphenyl ether disulfonate, and the cationic substance is (i) an ammonium salt. With such a configuration, the desired effect of the present invention can be efficiently exerted.

Specific examples of the adhesion controlling agent described in the present invention include, as a nonionic substance, (a) a polyol, (b) a hydroxy group-modified product of a polyol, (c) side-chain and/or terminal polyether-modified polysiloxane, or (d) an alkylene oxide adduct of higher aliphatic amine, as an amphoteric substance, (e) alkylaminobetaine, or (f) alkylamine oxide as an anionic substance, (g) a sulfuric acid ester salt of a higher alcohol alkylene oxide adduct, or (h) alkyl diphenyl ether disulfonate, and as a cationic substance, (i) an ammonium salt.

((a) Polyol)

Examples of a polyol having a plurality of hydroxy groups include (a-1) a non-polymeric polyol and (a-2) a polymeric polyol.

((a-1) Non-Polymeric Polyol)

specific examples of the non-polymeric polyol having a plurality of hydroxy groups include di-, tri- and tetraols such as ethylene glycol, diethylene glycol, triethylene glycol, glycerin, diglycerin, propanediol, butanediol, pentanediol, hexanediol, and octanediol and the like.

((a-2) Polymeric Polyol)

Specific examples of the polymeric polyol having a plurality of hydroxy groups include polyalkylene glycols such as polyethylene glycol and polypropylene glycol, and a block copolymer or random copolymer of polyethylene glycol and polypropylene glycol. Herein, the number of carbon atoms in the repeating unit of the alkylene unit is preferably C1 to C6, more preferably C2 to C4, and particularly preferably C2 to C3. (In the present specification, in some cases, the number of carbon atoms is expressed as a numerical value after "C." For example, when the number of carbon atoms is 1, it is expressed as C1, and when the number of carbon atoms is 10, it is expressed as C10.)

Incidentally, the polyalkylene glycol such as a block copolymer or random copolymer of polyethylene glycol and polypropylene glycol can be obtained from the market easily, and for example, the following products are preferably exemplified.

Products manufactured by ADEKA CORPORATION
Pluronic series
Pluronic L-34, Pluronic L-44, Pluronic L-64, Pluronic P-84, Pluronic P-85, Pluronic P-103, Pluronic F-68, Pluronic F-88, Pluronic F-108, Pluronic 17R-3, Pluronic 17R-4, Pluronic TR-704, and Pluronic TR-913R Products Manufactured by NOF CORPORATION
PLONON #104, PLONON #204, PLONON #248, UNILUBE 70DP-600B, and UNILUBE 70DP-950B Products Manufactured by DKS Co., Ltd.
EPAN 450, EPAN 485, EPAN 680, EPAN 740, EPAN 750, EPAN 785, EPAN U-103, EPAN U-105, and EPAN U-108

According to the preferred embodiment of the present invention, (a) the polyol is (poly)alkylene glycol. According to such an embodiment, adhesion between crushed hydrogel particles can be controlled.

((b) Hydroxy Group-Modified Product of Polyol)

As for the hydroxy group-modified product of the polyol, it is preferable that one or more hydroxy groups be modified with an ester and/or an ether. Ether and/or ester modification is preferably a hydrocarbon group, and the hydrocarbon group has preferably C1 to C30, more preferably C2 to C28, still more preferably C3 to C26, particularly preferably C4 to C24, and most preferably C6 to C22. When the number of carbon atoms is more than C30, hydrophobicity may become strong and the surface tension may be decreased, which is not preferable.

Further, the hydrocarbon group is not limited to a straight chain, and may be a branched or cyclic saturated hydrocarbon group and/or unsaturated hydrocarbon group, or an aromatic hydrocarbon group such as a phenyl group or an alkylphenyl group. Moreover, the hydrocarbon group may have a reactive functional group such as a hydroxy group, an amino group, or a glycidyl group.

However, a compound having two or more unsaturated hydrocarbon bonds at structural ends of the compound is not included. Specifically, a di(meth)acrylate compound having polyethylene glycol at both ends is not included, when the adhesion controlling agent is a radically polymerizable adhesion controlling agent having two or more unsaturated bonds at structural ends of the compound, in the case of adding the radically polymerizable adhesion controlling agent in the step (i) or the step (ii), the radically polymerizable adhesion controlling agent may be consumed by reaction during polymerization so that the radically polymerizable adhesion controlling agent may not remain. Furthermore, in the case of addition in the step (iii), the radically polymerizable adhesion controlling agent may not be sufficiently consumed to remain in a final product, which causes coloration.

When the adhesion controlling agent has a substituent, such as a hydroxy group, an amino group, a glycidyl group or the like, this substituent has reactivity with the carboxyl group included the water-absorbing resin as a functional group. Therefore the adhesion controlling agent remains on the surface of the gel particle so that excessive adhering of gel during gel-crushing is reduced. Moreover, the functional group reacts during drying so that crosslinking between gel particles also occurs and thus collapse of granulated particles can be further suppressed.

Examples of the hydroxy group-modified product of the polyol include (b-1) a glycidyl-modified polyol, (b-2) an alkylene oxide adduct of higher alcohol, (b-3) an alkylene oxide adduct of a polyhydric alcohol fatty acid ester.

According to the preferred embodiment of the present invention, (b) the hydroxy group-modified product of the polyol is (b-1) a glycidyl-modified polyol, (b-2) an alkylene oxide adduct of higher alcohol, or (b-3) an alkylene oxide adduct of a polyhydric alcohol fatty acid ester, (b-1) is (poly)alkylene glycol of which at least one of ends is modified with a glycidyl group, (b-2) is (poly)alkylene glycol of which one end is modified with a substituent having a C1 to C30 hydrocarbon, and (b-S) is polyhydric alcohol of which at least one hydroxy group is added by alkylene oxide and of which at least one hydroxy group is modified with a substituent having a C1 to C30 hydrocarbon via an ester bond, and the polyhydric alcohol is glycerin, pentaerythritol, sorbitol, sorbitan, or sugar. With such a configuration, adhesion between crushed hydrogels can be controlled.

((b-1) Glycidyl-Modified Polyol)

The glycidyl-modified polyol is (poly)alkylene glycol of which at least one of ends is modified with a glycidyl group. Specific examples thereof include water-soluble (poly)alkylene glycol diglycidyl ethers such as ethylene glycol diglycidyl ether, diethylene glycol diglycidyl ether, and polyethylene glycol diglycidyl ether; and water-soluble polyglycidyl ethers of polyols such as propylene glycol diglycidyl ether, polypropylene glycol diglycidyl ether, hexanediol diglycidyl ether, glycerol polyglycidyl ether, trimethylolpropane polyglycidyl ether, pentaerythritol polyglycidyl ether, diglycerol polyglycidyl ether, polyglycerol polyglycidyl ether, and sorbitol polyglycidyl ether.

When the adhesion controlling agent is (poly)alkylene glycol of which two or more hydroxy groups are modified with a glycidyl group, in the case of adding in the step (i) or the step (ii), the adhesion controlling agent may be consumed by reaction during polymerization so that the amount of the adhesion controlling agent may be decreased or the adhesion controlling agent may not remain during gel-crushing. Therefore, it is preferable to add the adhesion controlling agent after the step (ii).

The amount of (b-1) the glycidyl-modified polyol added may be in the above range of the amount of the adhesion controlling agent added, but is preferably 0.01 wt % to 5 wt %, more preferably 0.02 wt % to 3 wt %, and still more preferably 0.03 Wt % to 2 wt % with respect to the raw material monomer of the crosslinked hydrogel polymer.

The glycidyl-modified polyol can be obtained from the market easily, and for example, the following products are preferably exemplified.

Products manufactured by Nagase ChemteX Corporation
Denacol EX-145, Denacol EX-171, Denacol EX-211, Denacol EX-212, Denacol EX-252, Denacol EX-810, Denacol EX-811, Denacol EX-850, Denacol EX-851, Denacol EX-821, Denacol EX-830, Denacol EX-832, Denacol EX-841, Denacol EX-861, Denacol EX-911, Denacol EX-941, Denacol EX-920, Denacol EX-931, Denacol EX-313, Denacol EX-314, Denacol EX-321, Denacol EX-411, Denacol EX-421, Denacol EX-512, Denacol EX-521, Denacol EX-612, Denacol EX-614, and Denacol EX-614B ((b-2) Alkylene Oxide Adduct of Higher Alcohol)

The alkylene oxide adduct of higher alcohol is (poly) alkylene glycol of which one end is modified with a substituent having a C1 to C30 hydrocarbon, and the general formula thereof is represented in "Chemical Formula 1."

[Chemical Formula 1]

(Chemical Formula 1)

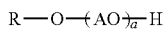

$R-O-(AO)_{\overline{a}}-H$

As R, the above-described hydrocarbon group having carbon atoms of C1 to C30 is not limited to a straight chain, and may be a branched or cyclic saturated hydrocarbon group and/or unsaturated hydrocarbon group, an aromatic hydrocarbon group such as an alkylphenyl group or an alkylbenzyl group, or a polycyclic aromatic hydrocarbon such as a naphthyl group. Further, the hydrocarbon group may have a reactive functional group such as a hydroxy group, an amino group, or a glycidyl group, or may have an ether bond, an ester bond, a urethane bond, or an amide bond. The number of carbon atoms of the hydrocarbon group is preferably C1 to C30, more preferably C2 to C28, still more preferably C3 to C26, particularly preferably C4 to C24, and most preferably C6 to C22. When the hydrocarbon group has more than C30, hydrophobicity becomes too strong and the surface tension of the water-absorbing agent is significantly decreased, which is not preferable.

AO is a repeating unit that can also be represented by $C_nH_{2n}O$ (n is a natural number). The number of carbon atoms thereof is preferably C1 to C6, more preferably C1 to C3, still more preferably C2 to C3, and particularly preferably C2, that is, in a case where the repeating unit is $CH_2CH_2O$ that is a structure derived from ethylene oxide addition or ethylene glycol condensation, it is particularly preferable.

The repeating unit may be a polymer of units having the same number of carbon atoms or may be a block polymer or random polymer of units having the different number of carbon atoms.

a is the number of repetitions of repeating units of AO, and is preferably from 1 to 1,000, more preferably from 2 to 500, and still more preferably from 2 to 300. When the number of repetitions of the repeating unit is more than 1,000, the viscosity is increased and addition is not uniform, which is not preferable.

The HLB of (b-2) the alkylene oxide adduct of higher alcohol as measured by a Griffin method is preferably 10 to 20, more preferably 12 to 20, and still more preferably 14 to 20. When the HLB is less than the above range, hydrophobicity becomes strong so that GCA is reduced, the absorption speed is decreased, or the surface tension is significantly decreased, which is not preferable. Further, the upper limit value is 20 in the method of determining the HLB.

The amount of (b-2) the alkylene oxide adduct of higher alcohol added may be in the above range of the amount of the adhesion controlling agent added, but is preferably 0.01 wt % to 5 wt %, more preferably 0.01 wt % to 2 wt %, and still more preferably 0.01 wt % to 0.5 wt % with respect to the raw material monomer of the crosslinked hydrogel polymer.

(b-2) The alkylene oxide adduct of higher alcohol can be obtained from the market easily, and for example, the following products are preferably exemplified.

Products manufactured by Kao Corporation

Polyoxyethylene lauryl ether

EMULGEN 106 (HLB=10.5), EMULGEN 109 (HLB=12.1), EMULGEN 109P (HLB=13.6), EMULGEN 120 (HLB=15.3), EMULGEN 123P (HLB=16.9), EMULGEN 130K (HLB=18.1), EMULGEN 147 (HLB=16.3), and EMULGEN 150 (HLB=18.4)

Polyoxyethylene cetyl ether

EMULGEN 210P (HLB=10.7) and EMULGEN 220 (HLB=14.2)

Polyoxyethylene-stearyl ether

EMULGEN 320P (HLB=13.9) and EMULGEN 350 (HLB=17.8)

Polyoxyethylene oleyl ether

EMULGEN 408 (HLB=10.0), EMULGEN 409PV (HLB=12.0), EMULGEN 420 (HLB=13.6), and EMULGEN 430 (HLB=16.2)

Polyoxyethylene myristyl ether

EMULGEN 4085 (HLB=18.9)

Polyoxyethylene octyl dodecyl ether

EMULGEN 2020G-HA (HLB=13.0) and EMULGEN 2025G (HLB=15.7)

Products Manufactured by NOF CORPORATION

Polyoxyethylene isodecyl ether

Nonion ID-203 (HLB=12.5) and Nonion ID-209 (HLB=14.3)

Polyoxyethylene-2-ethylhexyl ether

Nonion EH-204 (HLB=11.5) and Nonion EH-208 (HLB=14.6)

Products Manufactured by NIPPON NYUKAZAI CO., LTD.

Polyoxyethylene nonylphenyl ether

Newcol 560 (HLB=10.9), Newcol 564 (HLB=12.3), Newcol 565 (HLB=13.3), Newcol 566 (HLB=14.1), Newcol 568 (HLB=15.2), Newcol 504 (HLB=16.0), Newcol 506 (HLB=17.2), Newcol 509 (HLB=18.0), and Newcol 516 (HLB=18.8)

((b-3) Alkylene Oxide Adduct of Polyhydric Alcohol Fatty Acid Ester)

The ethylene oxide adduct of the polyhydric alcohol fatty acid ester is polyhydric alcohol of which at least one hydroxy group is added alkylene oxide and of which at least one hydroxy group is modified with a substituent having a C1 to C30 hydrocarbon via an ester bond. As the polyhydric alcohol, glycerin, pentaerythritol, sorbitol, sorbitan, sugar, and the like are exemplified.

Preferably, an alkylene oxide adduct of a glycerin fatty acid monoester and an alkylene oxide adduct of a sorbitan fatty acid monoester are exemplified, and the general formula of the alkylene oxide adduct of the glycerin fatty acid monoester is represented in "Chemical Formula 2." Since the alkylene oxide adduct of the sorbitan fatty acid monoester includes a structural isomer, the alkylene oxide adduct of the sorbitan fatty acid monoester is separately represented in general formulae "Chemical Formula 3" and "Chemical Formula 4,"

[Chemical Formula 2]

(Alkylene Oxide Adduct of Glycerin Fatty Acid Ester)

Chemical Formula 2

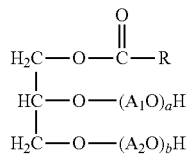

[Chemical Formula 4]

Chemical Formula 4

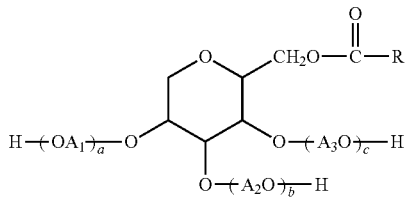

(Ethylene oxide adduct 2 of sorbitan fatty acid ester)

As R, the above-described hydrocarbon group having carbon atoms of C1 to C30 is not limited to a straight chain, and may be a branched or cyclic saturated hydrocarbon group and/or unsaturated hydrocarbon group, an aromatic hydrocarbon group such as an alkylphenyl group or an alkylbenzyl group, or a polycyclic aromatic hydrocarbon such as a naphthyl group. Further, the hydrocarbon group may have a reactive functional group such as a hydroxy group, an amino group, or a glycidyl group, or may have an ether bond, an ester bond, a urethane bond, or an amide bond. The number of carbon atoms of the hydrocarbon group is preferably C1 to C30, more preferably C2 to C28, still more preferably C3 to C26, particularly preferably C4 to C24, and most preferably C6 to C22. When the hydrocarbon group has more than C30, hydrophobicity becomes too strong and the surface tension of the water-absorbing agent is significantly decreased, it is not preferable.

$A_1O$ and $A_2O$ are a repeating unit that can also be represented by $C_nH_{2n}O$ (n is a natural number). The number of carbon atoms thereof is preferably C1 to C6, more preferably C1 to C3, still more preferably C2 to C3, and particularly preferably C2, that is, in a case where the repeating unit is $CH_2CH_2O$ that is a structure derived from ethylene oxide addition or ethylene glycol condensation, it is particularly preferable.

The repeating unit may be a polymer of units having the same number of carbon atoms or may be a block polymer or random polymer of units having the different number of carbon atoms. $A_1O$ and $A_2O$ may be different from each other or may be the same.

a and b are the number of repetitions of repeating units of $A_1O$ and $A_2O$, and the total of a+b is preferably from 1 to 1,000, more preferably from 2 to 500, and still more preferably from 2 to 300. a and b may be different from each other or may be the same. When the total of a+b is more than 1,000, the viscosity is increased and addition is not uniform, which is not preferable.

[Chemical Formula 3]

Chemical Formula 3

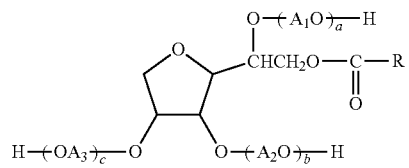

(Ethylene oxide adduct 1 of sorbitan fatty acid ester)

As R, the above-described hydrocarbon group having carbon atoms of C1 to C30 is not limited to a straight chain, and may be a branched or cyclic saturated hydrocarbon group and/or unsaturated hydrocarbon group, an aromatic hydrocarbon group such as an alkylphenyl group or an alkylbenzyl group, or a polycyclic aromatic hydrocarbon such as a naphthyl group. Further, the hydrocarbon group may have a reactive functional group such as a hydroxy group, an amino group, or a glycidyl group, or may have an ether bond, an ester bond, a urethane bond, or an amide bond. The number of carbon atoms of the hydrocarbon group is preferably C1 to C30, more preferably C2 to C28, still more preferably C3 to C26, particularly preferably C4 to C24, and most preferably C6 to C22. When the hydrocarbon group has more than C30, hydrophobicity becomes too strong and the surface tension of the water-absorbing agent is significantly decreased, it is not preferable.

$A_1O$, $A_2O$, and $A_3O$ are a repeating unit that can also be represented by $C_nH_{2n}O$ (n is a natural number). The number of carbon atoms thereof is preferably C1 to C6, more preferably C1 to C3, still more preferably C2 to C3, and particularly preferably C2, that is, in a case where the repeating unit is $CH_2CH_2O$ that is a structure derived from ethylene oxide addition or ethylene glycol condensation, it is a repeating unit is particularly preferable.

The repeating unit may be a polymer of units having the same number of carbon atoms or may be a block polymer or random polymer of units having the different number of carbon atoms. $A_1O$, $A_2O$, and $A_3O$ may be different from each other or may be the same.

a, b, and c are the number of repetitions of the repeating units, and the total of a+b+c is preferably from 1 to 1,000, more preferably from 2 to 500, and still more preferably from 2 to 300. a and b may be different from each other or may be the same. When the total of a+b+c is more than 1,000, the viscosity is increased and addition is not uniform, it is not preferable.

a, b, and c are an average repeating unit of polyethylene glycol, and the total amount of a+b+c is preferably from 1 to 300, more preferably from 2 to 200, and still more preferably from 2, to 100. a, b, and c may be different from each other or may be the same.

The HLB of (b-3) the alkylene oxide adduct of the polyhydric alcohol fatty acid ester as measured by a Griffin method is preferably 10 to 20, more preferably 12 to 20, and still more preferably 14 to 20. When the HLB is less than the above range, hydrophobicity becomes strong so that GCA is reduced, the absorption speed is decreased, or the surface tension is significantly decreased, it is not preferable. Further, the upper limit value is 20 in the method of determining the HLB.

The amount of (b-3) the alkylene oxide adduct of a polyhydric alcohol fatty acid ester added may be in the above range of the amount of the adhesion controlling agent added, but is preferably 0.01 wt % to 5 wt %, more preferably 0.01 wt % to 2 wt %, and still more preferably 0.01 wt % to 0.5 wt % with respect to the raw material monomer of the crosslinked hydrogel polymer.

(b-3) The alkylene oxide adduct of a polyhydric alcohol fatty acid ester can be obtained from the market easily, and for example, the following products are preferably exemplified.

Products Manufactured by Kao Corporation

Polyoxyethylene sorbitan monolaurate

RHEODOL TW-L120 (HLB=16.7), RHEODOL TW-L106 (HLB=13.3), and RHEODOL SUPER TW-L120

Polyoxyethylene sorbitan monopalmitate

RHEODOL TW-P120 (HLB=15.6)

Polyoxyethylene sorbitan monostearate

RHEODOL TW-S120V (HLB=14.9)

Polyoxyethylene sorbitan tristearate

RHEODOL TW-S320V (HLB=10.5)

Polyoxyethylene sorbitan monooleate

RHEODOL TW-O120V (HLB=15.0) and RHEODOL TW-O106V (HLB=10.0)

Polyoxyethylene sorbitan trioleate

RHEODOL TW-O320V (HLB=11.0)

Products Manufactured by NOF CORPORATION

Polyoxyethylene glyceryl coconut oil fatty acid

UNIGLY MK-207 (HLB=13.0) and UNIGLY MK-230 (HLB=17.4)

((c) Side-Chain and/or Terminal Polyether-Modified Polysiloxane)

The polyether-modified site in the polysiloxane is not particularly limited, but may be a side chain of the polysiloxane, both ends of the polysiloxane, one end of the polysiloxane, or both of a side chain and both ends of the polysiloxane. Examples of a polyether-modified group include a polyoxyethylene group, a polyoxypropylene group, and a group having both of a polyoxyethylene group and a polyoxypropylene group.

The HLB of the polyether-modified polysiloxane as measured by a Griffin method is preferably 10 to 20, more preferably 12 to 20, and still more preferably 14 to 20. When the HLB is less than the above range, hydrophobicity becomes strong so that GCA is reduced, the absorption speed is decreased, or the surface tension is significantly decreased, it is not preferable. Further, the upper limit value is 20 in the method of determining the HLB.

The amount of (C) the side-chain and/or terminal polyether-modified polysiloxane added may be in the above range of the amount of the adhesion controlling agent added, but is preferably 0.01 wt % to 5 wt %, more preferably 0.01 wt % to 2 wt %, and still more preferably 0.01 wt % to 0.5 wt % with respect to the raw material monomer of the crosslinked hydrogel polymer.

The polyether-modified siloxane can be obtained from the market easily, and for example, the following products are preferably exemplified.

Products manufactured by Shin-Etsu Chemical Co., Ltd.

KF-351A (HLB=12), KF-353 (HLB=10), KF-354L (HLB=16), KF-355A (HLB=12), KF-615A (HLB=10), KF-640 (HLB=14), KF-642 (HLB=12), KF-643 (HLB=14), and KF-6011 (HLB=12)

Products manufactured by Dow Corning Toray Co., Ltd.

FZ-77 (HLB=11) and L-7604 (HLB=11)

((d) Alkylene Oxide Adduct of Higher Aliphatic Amine)

According to the preferred embodiment of the present invention, (d) the alkylene oxide adduct of higher aliphatic amine is primary amine having a C1 to C30 hydrocarbon of which two hydrogens of the primary amine are added by alkylene oxide. With such a configuration, adhesion between crushed hydrogels can be controlled.

The alkylene oxide adduct of higher aliphatic amine is primary amine having a C1 to C30 hydrocarbon group of which two hydrogens are modified with (poly)alkylene glycol, and the general formula thereof is represented in "Chemical Formula 5."

[Chemical Formula 5]

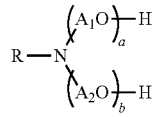

Chemical Formula 5

As R, the above-described hydrocarbon group having carbon atoms of C1 to C30 is not limited to a straight chain, and may be a branched or cyclic saturated hydrocarbon group and/or unsaturated hydrocarbon group, an aromatic hydrocarbon group such as an alkylphenyl group or an alkylbenzyl group, or a polycyclic aromatic hydrocarbon such as a naphthyl group. Further, the hydrocarbon group may have a reactive functional group such as a hydroxy group, an amino group, or a glycidyl group, or may have an ether bond, an ester bond, a urethane bond, or an amide bond. The number of carbon atoms of the hydrocarbon group is preferably C1 to C30, more preferably C2 to C28, still more preferably C3 to C26, particularly preferably C4 to C24, and most preferably C6 to C22. When the hydrocarbon group has more than C30, hydrophobicity becomes too strong and the surface-tension of the water-absorbing agent is significantly decreased, which is not preferable.

$A_1O$ and $A_2O$ are a repeating unit that can also be represented by $C_nH_{2n}O$ (n is a natural number). The number of carbon atoms thereof is preferably C1 to C6, more preferably C1 to C3, still more preferably C2 to C3, and particularly preferably C2, that is, a case where $CH_2CH_2O$ that is a structure derived from ethylene oxide addition or ethylene glycol condensation is a repeating unit is particularly preferable. The alkylene unit may be a polymer of units having the same number of carbon atoms or may be a block polymer or random polymer of units having the different number of carbon atoms. $A_1O$ and $A_2O$ may be different from each other or may be the same.

a and b are a repeating unit of an alkylene glycol unit, and the total of a+b is preferably from 1 to 1,000, more preferably from 2 to 500, and still more preferably from 2 to 300. a and b may be different from each other or may be the same. When the total of a+b is more than 1,000, the viscosity is increased and addition is not uniform, it is not preferable.

The HLB of (d) the alkylene oxide adduct of higher aliphatic amine as measured by a Griffin method is preferably 10 to 20, more preferably 12 to 20, and still more preferably 14 to 20. When the HLB is less than the above range, hydrophobicity becomes strong so that GCA is reduced, the absorption speed is decreased, or the surface tension is significantly decreased, it is not preferable. Further, the upper limit value is 20 in the method of determining the HLB.

The amount of (d) the alkylene oxide adduct of higher aliphatic amine added may be in the above range of the amount of the adhesion controlling agent added, but is preferably 0.01 wt % to 5 wt %, more preferably 0.01 wt % to 2 wt %, and still more preferably 0.01 wt % to 0.5 Wt % with respect to the raw material monomer of the crosslinked hydrogel polymer.

(d) The alkylene oxide adduct of higher aliphatic amine can be obtained from the market easily, and for example, the following products are preferably exemplified.

Products manufactured by NOF CORPORATION
Polyoxyethylene lauryl amine
NYMBEN L-207 (HLB=12.5)
Polyoxyethylene alkyl(coconut) amine
NYMEEN F-215 (HLB=15.4)
Polyoxyethylene stearylamine
NYMEEN S-210 (HLB=12.5), NYMEEN S-215 (HLB=14.5), and NYMEEN S-220 (HLB=15.4)
Polyoxyethylene beef tallow alkyl amine
NYMEEN T2-210 (HLB=12.5) and NYMEEN T2-230 (HLB=16.7)
Polyoxyethylene alkyl propylene diamine
NYMEEN DT-208 (HLB=10.7)
Products manufactured by Kao Corporation
AMIET 105A (HLB=10.8), AMIET 320 (HLB=15.4)
((e) Alkylaminobetaine)

The alkylaminobetaine has a cationic group and an anionic group at positions which are not adjacent in the same molecule, the cationic group is secondary to quaternary ammoniums, at least one of secondary to quaternary ammoniums is modified with a substituent having a C1 to C3D hydrocarbon group, and the general formula thereof is represented in "Chemical Formula 6."

[Chemical Formula 6]

Chemical Formula 6

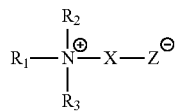

As $R_1$, the above-described hydrocarbon group having carbon atoms of C1 to C30 is not limited to a straight chain, and may be a branched or cyclic saturated hydrocarbon group and/or unsaturated hydrocarbon group, an aromatic hydrocarbon group such as an alkylphenyl group or an alkylbenzyl group, or a polycyclic aromatic hydrocarbon such as a naphthyl group. Further, the hydrocarbon group may have a reactive functional group such as a hydroxy group, an amino group, or a glycidyl group, or may have an ether bond, an eater bond, a urethane bond, or an amide bond. The number of carbon atoms of the hydrocarbon group is preferably C1 to C30, more preferably C2 to C28, still more preferably C3 to C26, particularly preferably C4 to C24, and most preferably C6 to C22. When the hydrocarbon group has more than C30, hydrophobicity becomes too strong and the surface tension of the water-absorbing agent is significantly decreased, which is, not preferable.

$R_2$ and $R_3$ are hydrogen or a hydrocarbon group, and the above-described hydrocarbon group having carbon atoms of C1 to C30 is not limited to a straight chain, and may be a branched or cyclic saturated hydrocarbon group and/or unsaturated hydrocarbon group, an aromatic hydrocarbon group such as an alkylphenyl group or an alkylbenzyl group, or a polycyclic aromatic hydrocarbon such as a naphthyl group. Further, the hydrocarbon group may have a reactive functional group such as a hydroxy group, an amino group, or a glycidyl group, or may have an ether bond, an ester bond, a urethane bond, or an amide bond. The number of carbon atoms of the hydrocarbon group is preferably C1 to C30, more preferably C1 to C25, and still more preferably C1 to C20. When the hydrocarbon group has more than C30, hydrophobicity becomes too strong and the surface tension of the water-absorbing agent is significantly decreased, which is not preferable. $R_1$, $R_2$, and $R_3$ may be different from each other or may be the same.

The structure of X is not particularly limited except that X has carbon atoms of C1 or more.

Examples of an anionic portion (Z) include carboxylates, sulfonates, and phosphates.

However, in addition to the matter that is represented in the general formula "Chemical Formula 6," the alkylaminobetaine has a cationic group on an imidazolium ring like AMPHITOL 20YB (manufactured by Kao Corporation) represented in the following "Chemical Formula 7."

[Chemical Formula 7]

Chemical Formula 7

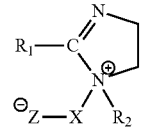

As $R_1$, the above-described hydrocarbon group having carbon atoms of C1 to C30 is not limited to a straight chain, and may be a branched or cyclic saturated hydrocarbon group and/or unsaturated hydrocarbon group, an aromatic hydrocarbon group such as an alkylphenyl group or an alkylbenzyl group, or a polycyclic aromatic hydrocarbon such as a naphthyl group. Further, the hydrocarbon group may have a reactive functional group such as a hydroxy group, an amino group, or a glycidyl group, or may have an ether bond, an ester bond, a urethane bond, or an amide bond. The number of carbon atoms of the hydrocarbon group is preferably C1 to C30, more preferably C2 to C28, still more preferably C3 to C26, particularly preferably C4 to C24, and most preferably C6 to C22. When the hydrocarbon group has more than C30, hydrophobicity becomes too strong and the surface tension of the water-absorbing agent is significantly decreased, which is not preferable.

$R_2$ is hydrogen or a hydrocarbon group, and the above-described hydrocarbon group having carbon atoms of C1 to C30 is not limited to a straight chain, and may be a branched or cyclic saturated hydrocarbon group and/or unsaturated hydrocarbon group, an aromatic hydrocarbon group such as an alkylphenyl group or an alkylbenzyl group, or a polycyclic aromatic hydrocarbon such as a naphthyl group. Further, the hydrocarbon group may have a reactive functional group such as a hydroxy group, an amino group, or a glycidyl group, or may have an ether bond, an ester bond, a urethane bond, or an amide bond. The number of carbon atoms of the hydrocarbon group is preferably C1 to C30, more preferably C1 to C25, and still more preferably C1 to C20. When the hydrocarbon group has more than C30, hydrophobicity becomes too strong and the surface tension of the water-absorbing agent is significantly decreased, it is not preferable. $R_1$ and $R_2$ may be different from each other or may be the same.

The structure of X is not particularly limited except that X has carbon atoms of C1 or more.

Examples of an anionic portion (Z) include carboxylates, sulfonates, and phosphates.

(f) Alkylamine Oxide

The alkylamine oxide has a cationic group and an anionic group at positions which are not adjacent in the same molecule, the cationic group is secondary to quaternary ammoniums, secondary to quaternary ammoniums is modified with at least one of a substituent having a C1 to C30 hydrocarbon group, and the general formula thereof is represented in "Chemical Formula 8."

[Chemical Formula 8]

[Chemical Formula 8]

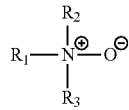

Chemical Formula 8

As $R_1$, the above-described hydrocarbon group having carbon atoms of C1 to C30 is not limited to a straight chain, and may be a branched or cyclic saturated hydrocarbon group and/or unsaturated hydrocarbon group, an aromatic hydrocarbon group such as an alkylphenyl group or an alkylbenzyl group, or a polycyclic aromatic hydrocarbon such as a naphthyl group. Further, the hydrocarbon group may have a reactive functional group such as a hydroxy group, an amino group, or a glycidyl group, or may have an ether bond, an ester bond, a urethane bond, or an amide bond. The number of carbon atoms of the hydrocarbon group is preferably C1 to C30, more preferably C2 to C28, still more preferably C3 to C26, particularly preferably C4 to C24, and most preferably C6 to C22. When the hydrocarbon group has more than C30, hydrophobicity becomes too strong and the surface tension of the water-absorbing agent is significantly decreased, which is not preferable.

$R_2$ and $R_3$ are hydrogen or a hydrocarbon group, and the above-described hydrocarbon group having carbon atoms of C1 to C30 is not limited to a straight chain, and may be a branched or cyclic saturated hydrocarbon group and/or unsaturated hydrocarbon group, an aromatic hydrocarbon group such as an alkylphenyl group or an alkylbenzyl group, or a polycyclic aromatic hydrocarbon such as a naphthyl group. Further, the hydrocarbon group may have a reactive functional group such as a hydroxy group, an amino group, or a glycidyl group, or may have an ether bond, an ester bond, a urethane bond, or an amide bond. The number of carbon atoms of the hydrocarbon group is preferably C1 to C30, more preferably C1 to C25, and still more preferably C1 to C20. When the hydrocarbon group has more than C30, hydrophobicity becomes too strong and the surface tension of the water-absorbing agent is significantly decreased, which is not preferable. $R_1$, $R_2$, and $R_1$ may be different from each other or may be the same.

The amounts of (e) the alkylaminobetaine and (f) the alkylamine oxide added may be in the above range of the amount of the adhesion controlling agent added, but are preferably 0.01 wt % to 5 wt %, more preferably 0.01 wt % to 2 wt %, and still more preferably 0.01 wt % to 0.5 wt % with respect to the raw material monomer of the crosslinked hydrogel polymer.

(e) The alkylaminobetaine and (f) the alkylamine oxide can be obtained from the market easily, and for example, the following products are preferably exemplified.

Products manufactured by Kao Corporation:
AMPHITOL 20BS, AMPHITOL 24B (desalinated product of 20S), AMPHITOL 86B, AMPHITOL 20N, AMPHITOL 20YB, AMPHITOL 20AB, AMPHITOL 55AB, and AMPHITOL 20HD Products manufactured by DKS Co., Ltd.:
AMOGEN S-H, AMOGEN K, AMOGEN LB-C, AMOGEN CB-H, AMOGEN HB-C, and AMOGEN AOL Products manufactured by ADEKA CORPORATION:
ADEKA AMPHOTE PB-30L and ADEKA AMPHOTE AB-35L Products manufactured by NOF CORPORATION:
NISSANANON BF, NISSANANON BL, NISSANANON BL-SF, NISSANANON BDF-R, NISSANANON BDF-SF, NISSANANON BDC-SF, NISSANANON BDL-SF, NISSANANON GLM-R, UNISAFE A-LM, UNISAFE A-SM, and UNISAFE A-LE Products manufactured by NIPPON NYUKAZAI CO., LTD.:
Texnol R2

((g) Sulfuric Acid Ester Salt of Higher Alcohol Ethylene Oxide Adduct)

According to the preferred embodiment of the present invention, (g) the sulfuric acid ester salt of the higher alcohol alkylene oxide adduct is (poly)alkylene glycol of which one end is modified with a substituent having a C1 to C30 hydrocarbon and the other end is a sulfuric acid ester salt. With such a configuration, adhesion between crushed hydrogels can be controlled.

The sulfuric acid ester salt of the higher alcohol alkylene oxide adduct is (poly)alkylene glycol of which one end is modified with a substituent having a C1 to C30 hydrocarbon and the other end is a sulfuric acid ester salt, and the general formula thereof is represented in "Chemical Formula 9."

[Chemical Formula 9]

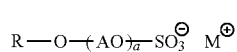

Chemical Formula 9

As R, the above-described hydrocarbon group having carbon atoms of C1 to C30 is not limited to a straight chain, and may be a branched or cyclic saturated hydrocarbon group and/or unsaturated hydrocarbon group, an aromatic hydrocarbon group such as an alkylphenyl group or an alkylbenzyl group, or a polycyclic aromatic hydrocarbon such as a naphthyl group. Further, the hydrocarbon group may have a reactive functional group such as a hydroxy group, an amino group, or a glycidyl group, or may have an ether bond, an eater bond, a urethane bond, or an amide bond. The number of carbon atoms of the hydrocarbon group is preferably C1 to C30, more preferably C2 to C28, still more preferably C3 to C26, particularly preferably C4 to C24, and most preferably C6 to C22. When the hydrocarbon group has more than C30, hydrophobicity becomes too strong and the surface tension of the water-absorbing agent is significantly decreased, which is not preferable.

AO is a repeating unit that can also be represented by $C_nH_{2n}O$ (n is a natural number). The number of carbon atoms thereof is preferably C1 to C6, more preferably C1 to C3, still more preferably C2 to C3, and particularly preferably C2, that is, in a case where the repeating unit is $CH_2CH_2O$ that is a structure derived from ethylene oxide addition or ethylene glycol condensation, it is a repeating unit is particularly preferable.

The repeating unit may be a polymer of units having the same number of carbon atoms or may be a block polymer or random polymer of units having the different number of carbon atoms.

a is the number of repetitions of repeating units of AO, and is preferably from 1 to 1,000, more preferably from 2 to 500, and still more preferably from 2 to 300. When the number of repetitions of the repeating unit is more than 1,000, the viscosity is increased and addition is not uniform, which is not preferable.

As M, alkali metals (Li, Na, and K) and ammonium ions are exemplified.

The amount of (g) the sulfuric acid ester salt of the higher alcohol alkylene oxide adduct added may be in the above range of the amount of the adhesion controlling agent added, but is preferably 0.01 wt % to 5 wt %, more preferably 0.01 wt % to 2 wt %, and still more preferably 0.01 wt % to 0.5 wt % with respect to the raw material monomer of the crosslinked hydrogel polymer.

(g) The sulfuric acid ester salt of the higher alcohol alkylene oxide adduct can be obtained from the market easily, and for example, the following products are preferably exemplified.

Products manufactured by Kao Corporation
Sodium polyoxyethylene lauryl ether sulfate
EMAL 20C, EMAL E-27C, EMAL 270J, and EMAL 20CM
Products manufactured by NIPPON NYUKAZAI CO., LTD.
Polyoxyethylene alkyl ether sulfuric acid ester salt
Newcol 1020-SN, Newcol 2308-SF, Newcol 2320-SN, Newcol 2360-SN, Newcol 1305-SN, Newcol 1330-SF, Newcol 1703-SFD, and Newcol 1525-SFC
Products manufactured by NOF CORPORATION
Polyoxyethylene alkyl ether sulfate sodium
PERSOFT EP, NISSAN TRAX K-40, NISSAN TRAX K-300, PERSOFT EF, PERSOFT EDO, PERSOFT EL, and PERSOFT EK ((h) Alkyl Diphenyl Ether Disulfonate)

The general formula of the alkyl diphenyl ether disulfonate is represented in "Chemical Formula 10."

[Chemical Formula 10]

Chemical Formula 10

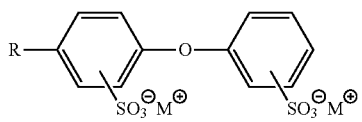

As R, the above-described hydrocarbon group having carbon atoms of C1 to C30 is not limited to a straight chain, and may be a branched or cyclic saturated hydrocarbon group and/or unsaturated hydrocarbon group, an aromatic hydrocarbon group such as an alkylphenyl group or an alkylbenzyl group, or a polycyclic aromatic hydrocarbon such as a naphthyl group. Further, the hydrocarbon group may have a reactive functional group such as a hydroxy group, an amino group, or a glycidyl group, or may have an ether bond, an ester bond, a urethane bond, or an amide bond. The number of carbon atoms of the hydrocarbon group is preferably C1 to C30, more preferably C2 to C28, still more preferably C3 to C26, particularly preferably C4 to C24, and most preferably C6 to C22. When the hydrocarbon group has more than C30, hydrophobicity becomes too strong and the surface tension of the water-absorbing agent is significantly decreased, which is not preferable.

As M, alkali metals (Li, Na, and K) and ammonium ions are exemplified.

The amount of (h) the alkyl diphenyl ether disulfonate added may be in the above range of the amount of the adhesion controlling agent added, but is preferably 0.01 wt % to 5 wt %, more preferably 0.01 wt % to 2 wt %, and still more preferably 0.01 wt % to 0.5 wt % with respect to the raw material monomer of the crosslinked hydrogel polymer.

(h) The alkyl diphenyl ether disulfonate can be obtained from the market easily, and for example, the following products are preferably exemplified.

Products manufactured by Kao Corporation
Sodium alkyl diphenyl ether disulfonate
PELEX SS-L and PELEX SS-H
Products manufactured by TAKEMOTO OIL & FAT Co., Ltd.
Sodium alkyl diphenyl ether disulfonate
PIONIN A-43-D and TAKESURF A-43-NQ ((i) Ammonium Salt)

The ammonium salt is ammonium salt of which at least one hydrogen is modified with a substituent having a C1 to C30 hydrocarbon, and the general formula thereof is represented in "Chemical Formula 11."

[Chemical Formula 11]

Chemical Formula 11

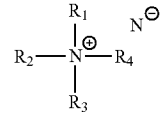

As $R_1$, the above-described hydrocarbon group having carbon atoms of C1 to C30 is not limited to a straight chain, and may be a branched or cyclic saturated hydrocarbon group and/or unsaturated hydrocarbon group, an aromatic hydrocarbon group such as an alkylphenyl group or an alkylbenzyl group, or a polycyclic aromatic hydrocarbon such as a naphthyl group. Further, the hydrocarbon group may have a reactive functional group such as a hydroxy group, an amino group, or a glycidyl group, or may have an ether bond, an ester bond, a urethane bond, or an amide bond. The number of carbon atoms of the hydrocarbon group is preferably C1 to C30, more preferably C2 to C28, still more preferably C3 to C26, particularly preferably C4 to C24, and most preferably C6 to C22. When the hydrocarbon group has more than C30, hydrophobicity becomes too strong and the surface tension of the water-absorbing agent is significantly decreased, which is not preferable.

$R_2$, $R_3$, and $R_4$ are hydrogen or a hydrocarbon group, and the above-described hydrocarbon group having carbon atoms of C1 to C30 is not limited to a straight chain, and may be a branched or cyclic saturated hydrocarbon group and/or unsaturated hydrocarbon group, an aromatic hydrocarbon group such as an alkylphenyl group or an alkylbenzyl group, or a polycyclic aromatic hydrocarbon such as a naphthyl group. Further, the hydrocarbon group may have a reactive functional group such as a hydroxy group, an amino group, or a glycidyl group, or may have an ether bond, an ester bond, a urethane bond, or an amide bond. The number of carbon atoms of the hydrocarbon group is preferably C1 to C30, more preferably C1 to C25, and still more preferably C1 to C20. When the hydrocarbon group has more than C30, hydrophobicity becomes too strong and the surface tension of the water-absorbing agent is significantly decreased, which is not preferable. $R_1$, $R_2$, $R_3$, and $R_4$ may be different from each other or may be the same.

N is counter anion of ammonium cation, and examples thereof include halogen ion, carboxylate ion, sulfonate ion, hydroxy ion, $BF^{4-}$, $PF^{6-}$, $ClO^{4-}$, $AsF^{6-}$, and $SbF^{6-}$.

The amount of (i) the ammonium salt added may be in the above range of the amount of the adhesion controlling agent added, but is preferably 0.01 wt % to 5 wt %, more preferably 0.01 wt % to 2 wt %, and still more preferably 0.01 wt % to 0.5 wt % with respect to the raw material monomer of the crosslinked hydrogel polymer.

(i) The ammonium salt can be obtained from the market easily, and for example, the following products are preferably exemplified.

Products manufactured by Kao Corporation
Coconut amine acetate
ACETAMIN 24
Stearylamine acetate
ACETAMIN 86
Lauryl trimethyl ammonium chloride
QUARTAMIN 24P
Stearyl trimethyl ammonium chloride
QUARTAMIN 86W
Cetyl trimethyl ammonium chloride
QUARTAMIN 60W
Distearyl dimethyl ammonium chloride
QUARTAMIN D86P
Alkylbenzyl dimethyl ammonium chloride
SANISOL C and SANISOL B-50
Products manufactured by NOF CORPORATION
Tetradecyl amine acetate
NISSANCATION MA
Dodecyl trimethyl ammonium chloride
NISSANCATION BB
Coco alkyl trimethyl ammonium chloride
NISSANCATION FB
Hexadecyl trimethyl ammonium chloride
NISSANCATION PB-300
Beef-tallow-alkyl trimethyl ammonium chloride
NISSANCATION ABT2-500
Octadecyl trimethyl ammonium chloride
NISSANCATION AB and NISSANCATION AB-600
Behenyl trimethyl ammonium chloride
NISSANCATION VB-M Flake and NISSANCATION VB-F
Didecyl dimethyl ammonium chloride
NISSANCATION 2-DB-500E
Dioleyl dimethyl ammonium chloride
NISSANCATION 2-OLR
Coco alkyl dimethyl benzyl ammonium chloride
NISSANCATION F2-50R
Tetradecyl dimethyl benzyl ammonium chloride
NISSANCATION M2-100R The adhesion controlling agent used in the present application preferably has a hydrophilic unit (a cationic group such as a quaternary ammonium salt, sulfonate, amine, or polyethylene glycol chain) and a hydrophobic unit (a hydrocarbon group) in the same compound. As the hydrophilic unit, a quaternary ammonium salt and a polyethylene glycol chain are particularly preferable.

It is considered that the hydrophilic unit of the adhesion controlling agent interacts with the inside or/and the surface of the hydrophilic particulate absorbing agent so as to be less likely to be eluted from the absorbing agent. For this reason, it is considered that a decrease in the surface tension of the absorbing agent is suppressed and the re-wet of liquid from a water-absorbing material is suppressed according to the decrease in the surface tension.

It is considered that the adhesion controlling agent is gathered on the surface layer (a portion close to an air layer) of the hydrogel particles after gel-crushing because of its hydrophobic property. So the hydrophobic unit of the adhesion controlling agent re-adhesion between gel particles can be suppressed since the effect of suppressing adhesion between the crushed gels is enhanced. Meanwhile, it is considered that the hydrophilic unit interacts with the gel so as to serve as an anchor for causing the adhesion controlling agent to remain on the surface of the gel particles.

Further, the adhesion controlling agent used in the present application is also preferably polyethylene glycol having only a hydrophilic unit without a hydrophobic unit. Particularly, it is considered that the polyethylene glycol having only a hydrophilic unit interacts with the inside or/and the surface of the hydrophilic particulate absorbing agent so as to be particularly less likely to be eluted from the absorbing agent. Further, since the optimal value range of the addition amount is wide and it is insensitive to a variation in the addition amount, the operation control range in production can be wide, which is preferable. Furthermore, when the polyethylene glycol is present on the surface of the hydrogel particles, a carboxyl group that is a functional group of the water-absorbing resin reacts with hydroxy groups at both ends of the polyethylene glycol in the drying step so as to crosslink primary particles that constitute granulated shaped particles, and thus the effect of suppressing collapse of the granulated shaped particles is achieved when the granulated shaped particles absorb water to be swollen, which is preferable.

As a main effect obtained by using an adhesion controlling agent, controlling adhesion between primary particles of the hydrogel particles is exemplified. Further, as an adventitious effect, improving flowability of the hydrogel and suppressing the strength of the dried product of the hydrogel particles are exemplified.

Further, when an adhesion controlling agent is used, it is possible to reduce a load to a gel-crusher by the lubrication effect of the adhesion controlling agent, productivity is further increased, and degradation of the gel during gel-crushing is suppressed, which is preferable.

The HL of the nonionic substance as measured by a Griffin method is preferably 10 to 20, more preferably 12 to 20, and still more preferably 14 to 20. When the HLB is less than the above range, hydrophobicity becomes strong so that GCA is reduced, the absorption speed is decreased, or the surface tension is significantly decreased, which is not preferable. Further, the upper limit value is 20 in the method of determining the HLB.

The molecular weight (weight average molecular weight) of the adhesion controlling agent is not particularly limited. However, in order to exert the effect with a smaller addition amount or to avoid negative effect such as a decrease in fluid retention capacity, the molecular weight (hereinafter, the weight average molecular weight in a case where the adhesion controlling agent is a polymer) is preferably in a range of 100 to 1,000,000, more preferably in a range of 150 to 500,000, still more preferably in a range of 200 to 500,000 or 300 to 300,000, still more preferably in a range of 500 to 200,000, particularly preferably in a range of 1,000 to 50,000 or less, and most preferably in a range of 30,000 or less. Further, particularly, in a case where polyethylene glycol is used as an adhesion controlling agent, when the weight average molecular weight is 500 or more, the desired effect of the present invention can be efficiently exerted.

When the molecular weight is less than the above range, the adhesion controlling agent is easily volatilized and the effect thereof is decreased, which is not preferable. When the molecular weight is more than the above range, the viscosity is increased and addition is not uniform, which is not preferable.

According to the preferred embodiment of the present invention, weight average molecular weights of the nonionic substance and (g) the sulfuric acid ester salt of the higher alcohol alkylene oxide adduct are each independently 200 to 200,000. According to such an embodiment, the adhesion between crushed hydrogel particles can be controlled, Further, in this embodiment, the weight average molecular weight is particularly preferably 50,000 or less and most preferably 30,000 or less (2-4) Drying Step (Step (iv))

This is a step for drying the hydrogel (hydrogel particles) obtained through the polymerization step and the like to obtain a dry polymer (dried product). Incidentally, in a case where the polymerization step is aqueous, solution polymerization, gel-crushing (grain refining) is performed before drying the hydrogel. Further, the dry polymer (agglomerate) (dried product) obtained in the drying step may be supplied to the pulverizing step as it is.

The drying method in the present invention is not particularly limited, and various methods can be employed. Specific examples thereof include heat drying, hot air drying, drying under reduced pressure, infrared drying, microwave drying, drying by azeotropic dehydration with a hydrophobic organic solvent, and high humidity drying using hot water vapor or the like. One kind of these can be used, or two kinds of these can be used together.

By performing drying in this drying step, finely crushed particulate hydrogels adhere to each other to form particles having a granulated form.

Incidentally, granulation in the present invention means formation of a particle larger than the original particle (primary particle) by attaching the particles together by a physical or chemical method, and it is characterized that the adhesion of the primary particles is loose or in contact with each other in point. A granulated product or granulated particles of the present invention are particles adhering to each other in a state where primary particles are clearly identified as shown in the drawings of Examples. Incidentally, the degree of adhesion is controlled by existence and types of the adhesion controlling agent so that GCA, FGBP, vortex, AAP, and the like can be controlled.

The drying temperature in the present invention is preferably 100° C. to 300° C. and more preferably 150° C. to 250° C. Further, the drying time depends on the surface area and the moisture content of the hydrogel particles, the kind of a drier, and the like, and thus is, for example, preferably 1 minute to 5 hours and more preferably 5 minutes to 1 hour.

Furthermore, the solids content of the water-absorbing resin (dried product) determined from an amount lost from drying (1 g of powder or particles is dried at 180° C. for 3 hours) is preferably 80 wt % or more, more preferably 85 wt % to 99 wt %, still more preferably 90 wt % to 98 wt %, and particularly preferably 92 wt % to 97 wt %.

(2-5) Pulverizing and Classification Step (Step (V))

This is a step for pulverizing and/or classifying the dry polymer (dried product) obtained in the drying step to preferably obtain water-absorbing resin powder having a specific particle size. Incidentally, this step is different from the above (2-3) Gel-Crushing Step in that the object to be crushed has passed through the drying step.

This step is performed before and/or after (2-6) Surface Crosslinking Step, is preferably performed before (2-6) Surface Crosslinking Step, and is more preferably performed at least two times before and after (2-6) Surface Crosslinking Step.

Examples of a device (pulverizer) used in the pulverizing step in the present invention include a high-speed rotary pulverizer such as a roll mill, a hammer mill, a screw mill, or a pin mill, a vibration mill, a knuckle type pulverizer, and a cylindrical mixer or the like. These devices are used together, if necessary.

(Particle Size)

The weight average particle diameter (D50) of the water-absorbing resin powder before surface crosslinking is preferably 300 μm to 500 μm, more preferably 310 μm to 480 μm, and still more preferably 320 μm to 450 μm from the viewpoint of handleability (particularly, handleability under moisture absorption), GCA, FGBP, the water absorption speed, the fluid retention capacity under pressure, and the like.

Further, a smaller amount of fine particles, which have a particle diameter of less than 150 μm specified by standard sieve classification, contained is better. The amount is preferably 0 wt % to 5 wt %, more preferably 0 wt % to 3 wt %, and still more preferably 0 wt % to 2 wt % with respect to the entire water-absorbing resin powder.

Furthermore, a smaller amount of coarse particles, which have a particle diameter of 850 μm or more specified by standard sieve classification, contained is better. The amount is preferably 0 wt % to 5 wt %, more preferably 0 wt % to 3 wt %, and still more preferably 0 wt % to 1 wt % with respect to the entire water-absorbing resin powder from the viewpoint of the water absorption speed and the like.

Further, the proportion of particles having a particle diameter of 150 μm or more and less than 850 m is preferably 90 wt % or more, more preferably 95 wt % or more, still more preferably 98 wt % or more, and particularly preferably 99 wt % or more (the upper limit is 100 wt %) with respect to the entire water-absorbing resin powder from the viewpoint of GCA, FGBP, the water absorption speed, the fluid retention capacity under pressure, and the like.

Further, the logarithmic standard deviation ($\sigma\zeta$) of the particle size distribution is preferably 0.20 to 0.50, more preferably 0.25 to 0.45, and still more preferably 0.30 to 0.40.

When the amount of fine particles which have a particle diameter of less than 150 μm contained is adjusted to a small value as the above range, dusting is reduced, handling becomes easier, and GCA, FGBP, and the fluid retention capacity under pressure are improved.

When this range is compared to the particle diameter range adjusted in the step for pulverizing and classifying and the particle diameter range of the water-absorbing agent, the particle diameter at the stage of gel-crushing is smaller, and thus the dried water-absorbing resin particles are in a state where the granulated form is highly developed.

Figure 2:
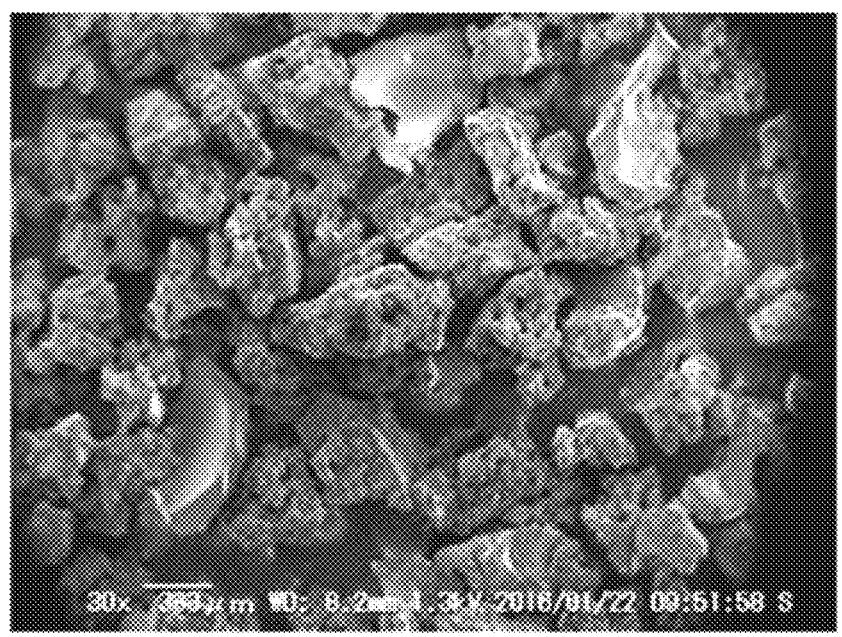
FIG. 2 is an SEM photograph (magnification: 30) of water-absorbing resin powder of Example 9.

That is, when a value obtained by dividing the weight average particle diameter of the water-absorbing agent by the weight average particle diameter of the hydrogel particles after gel-crushing converted to the dried product is increased, the proportion of the granulated particles shown in FIG. 2, {granulated particle/(particles having irregularly-crushed shape+granulated particle)}, is increased. The weight average particle diameter of the hydrogel particles converted to the dried product become smaller than the weight average particle diameter of 300 μm to 500 μm set in the particulate absorbing agent (water-absorbing resin powder), and the proportion of the granulated particles in the particulate water-absorbing agent is increased as the proportion of small particles is increased (refer to FIG. 2).

Figure 4:
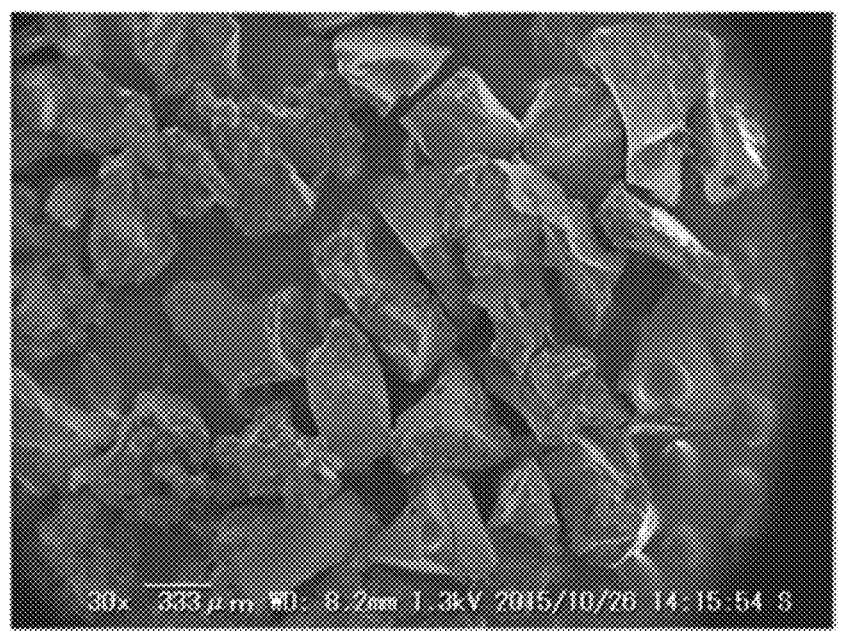
FIG. 4 is an SEM photograph (magnification: 30) of water-absorbing resin powder of Comparative Example 1.

As compared to FIG. 4 (the water-absorbing resin powder of Comparative Example 1), as seen in FIG. 2 (the water-absorbing resin powder of Example 9), it is obvious that the surface area is increased as the granulated particle ratio of the water-absorbing resin powder is increased in accordance with a decrease in the weight average particle diameter of the hydrogel particles converted to the dried product.

Figure 3:
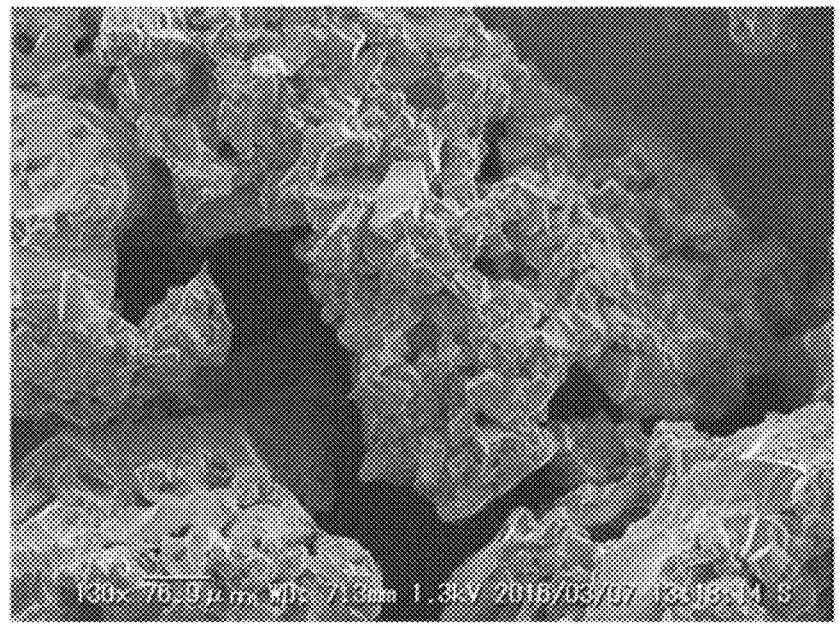
FIG. 3 is an SEM photograph (magnification: 130) of the water-absorbing resin powder of Example 9.
Figure 5:
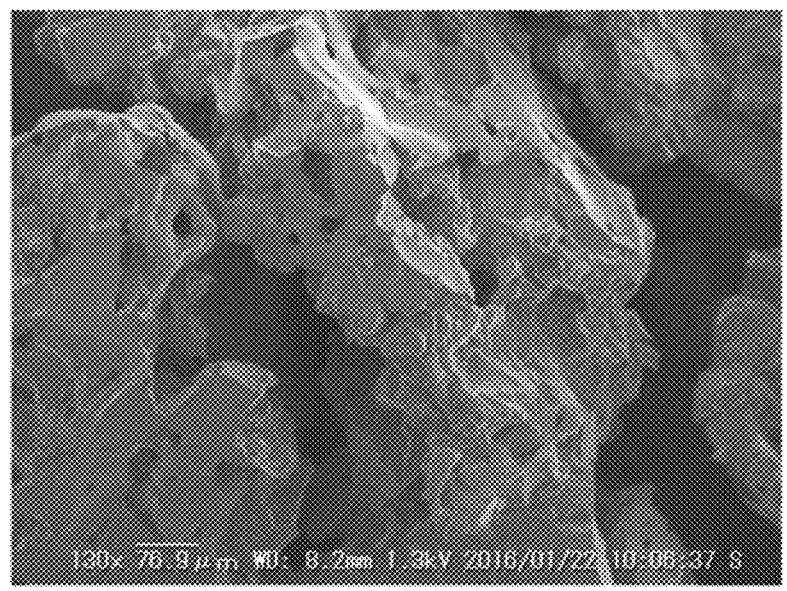
FIG. 5 is an SEM photograph (magnification: 130) of water-absorbing resin powder of Comparative Example 5.
Figure 6:
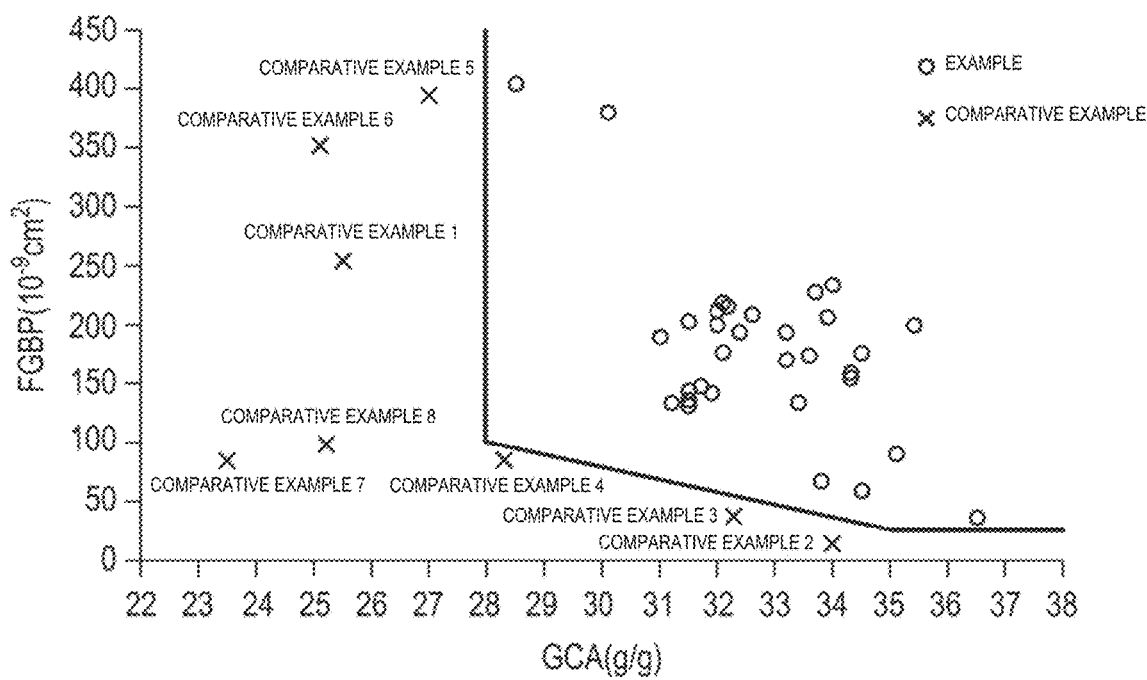
FIG. 6 is a correlation diagram showing a relation between Examples and Comparative Examples.
Figure 7:
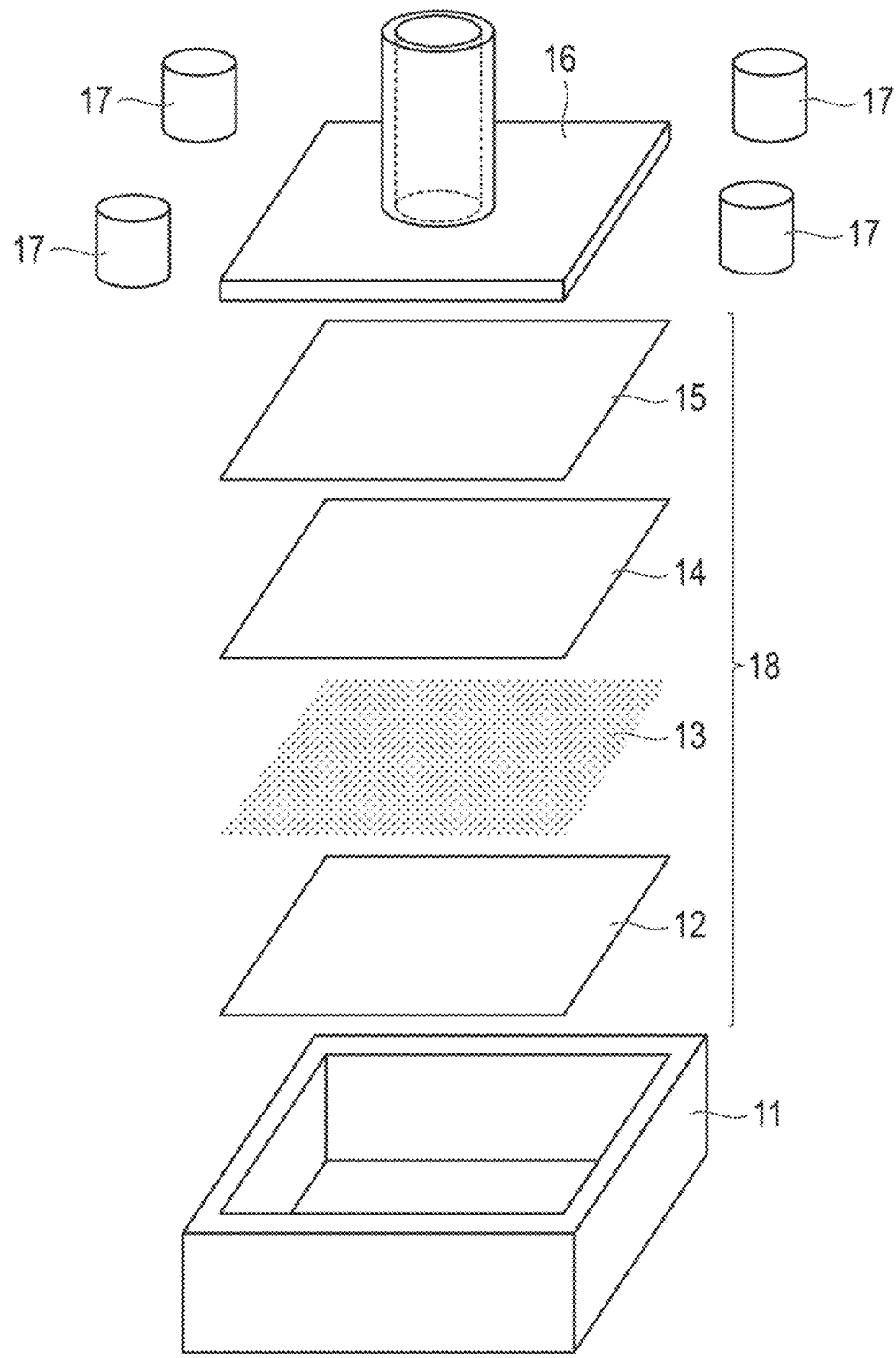
FIG. 7 is a schematic diagram of an apparatus used for evaluating an absorbent material of the present invention.

Further, as compared to FIG. 5 (the water-absorbing resin powder of Comparative Example 5), as seen in FIG. 3 (the water-absorbing resin powder of Example 9), it is obvious that with use of the adhesion controlling agent, the surface area of the granulated particles of the water-absorbing resin powder is increased.

A BET specific surface area described below in Examples can be employed as an index of the surface area.

The BET specific surface area of the water-absorbing resin powder having the same particle size (water-absorbing resin powder passing through a sieve having a mesh size of 425 μm and not passing through a sieve having a mesh size of 300 μm) is preferably 29 $m^2$/kg or more, more preferably 30 $m^3$/kg or more, and still more preferably 31 $m^2$/kg or more. Incidentally, the water-absorbing resin powder fractionated into a particle size of 300 μm or more and less than 425 μm is described as water-absorbing resin powder (425/300) in Table 5.

As described above, control of the particle size can be performed during polymerization, during gel-crushing, or during pulverizing or classification after drying, and is particularly preferably performed during pulverizing and/or classification after drying. Further, the particle size is measured using a JIS standard sieve in conformity with the method specified by WO 2004/69915 A or EDANA-ERT420.2-02.

In order to further solve the problem of the present invention, the particle size may also be applied to a water-absorbing resin particles after surface crosslinking or a particulate water-absorbing agent as a final product.

Fine particles (for example, particles passing through a wire mesh of 150 μm) generated by the control of the particle size may be discarded or recovered according to a recovery method into an aqueous monomer solution before polymerization (WO 92/001008 A and WO 92/020723 A) or a recovery method into a hydrogel during polymerization (WO 2007/074167 A, WO 2009/109563 A, WO 2009/153196 A, and WO 2010/006937 A) as known conventionally.

Further, the shape of the water-absorbing resin powder of the present invention is not limited to a spherical shape, a fibrous shape, a rod shape, a nearly spherical shape, a flat shape, an irregular shape, a granulated particle shape, and a particle having a porous structure, and the like.

(CRC Before Surface Crosslinking)

Since it is preferable that the water-absorbing agent of the present invention satisfy CRC ≥28 g/g, CRC of the water-absorbing resin powder before surface crosslinking is also preferably 28 g/g or more and more preferably 30 g/g or more. It is sufficient that the amount of the crosslinking agent during polymerization is appropriately adjusted in the ranges. CRC of the water-absorbing resin powder before surface crosslinking is appropriately adjusted in a range of preferably 30 g/g to 60 g/g, more 16 preferably 32 g/g to 55 g/g, and still more preferably 33 g/g to 50 g/g by the amount of the crosslinking agent, polymerization temperature, drying temperature, and the like.

In general, polymerization or drying at a high temperature tends to improve CRC. Further, an increase in the amount of the crosslinking agent leads to decrease of CRC. Thus, CRC of the water-absorbing agent of the present invention may be appropriately controlled by CRC before surface crosslinking, and the amount of the crosslinking agent in surface crosslinking, reaction temperature, and reaction time described below.

(2-6) Surface Crosslinking Step (Step (vi))

This step more specifically includes a step for adding a surface crosslinking agent described in (2-6-1) and a heat treatment step described in (2-6-2) described below.

(2-6-1) Step for Adding Surface Crosslinking Agent

This is a step for mixing the water-absorbing resin powder with a surface crosslinking agent to prepare water-absorbing resin powder containing a surface crosslinking agent provided to the surface crosslinking step.

In general, surface crosslinking is performed by addition of an organic surface crosslinking agent described below, polymerization of a monomer (polymerizable surface crosslinking agent) on the surface of the water-absorbing resin powder, or addition of a radical polymerization initiator (surface crosslinking agent in a broad sense) such as a persulfate and heating or irradiation with an ultraviolet ray, or the like. In the present invention, it is preferable to add an organic surface crosslinking agent to the water-absorbing resin powder obtained above.

(Organic Surface Crosslinking Agent)

As the organic surface crosslinking agent which can be used in the present invention, from the viewpoint of the physical properties of the resulting water-absorbing resin particles, an organic compound having a reactive group such as a hydroxy group and/or an amino group or the like to perform a dehydration esterification reaction or a dehydration amidation reaction with a carboxyl group as a functional group of the poly(meth)acrylic acid (salt)-based water-absorbing resin particles is preferable.

The organic compound is not limited to an alcohol compound and an amine compound directly having a hydroxy group or an amino group, and includes even a cyclic compound having a reactive group to generate a hydroxy group or an amino group and/or a reactive group to directly react with the carboxyl group, such as an alkylene carbonate compound or an oxazolidinone compound.

Examples of the organic surface crosslinking agent include a polyhydric alcohol compound, an epoxy compound, a polyvalent amine compound or a condensate thereof with a haloepoxy compound, an oxazoline compound, a (mono-, di-, or poly-) oxazolidinone compound, an oxetane compound, and an alkylene carbonate compound. A polyhydric alcohol compound, an alkylene carbonate compound, an oxazolidinone compound are more preferable.

Specific examples of the organic surface crosslinking agent include a polyalcohol compound (polyhydric alcohol) such as (di-, tri-, tetra-, or poly-) ethylene glycol, (di- or poly-) propylene glycol, 1,3-propanediol, 2,2,4-trimethyl-1,3-pentanediol, (poly)glycerin, 2-butene-1,4-diol, 1,4-butanediol, 1,3-butanediol, 1,5-pentanediol, 1,6-hexanediol, trimethylolpropane, di- or tri-ethanolamine, pentaerythritol, or sorbitol;

an epoxy compound such as (poly)ethylene glycol diglycidyl ether, (di- or poly-) glycerol polyglycidyl ether, or glycidol;

2-oxazadone or N-hydroxyethyl-2-oxazolidone;

an oxazoline compound such as 1,2-ethylene bisoxazoline;

an alkylene carbonate compound such as 1,3-dioxolan-2-one (that is, ethylene carbonate), 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxane-2-one, 4-methyl-1,3-dioxane-2-one, 4,6-dimethyl-1,3-dioxane-2-one, or 1,3-dioxopan-2-one;

a haloepoxy compound such as epichlorohydrin, epibromohydrin, or α-methylepichlorohydrin, and a polyvalent amine adduct thereof (for example, Kaimen manufactured by Hercules Inc.; registered trademark);

a slime coupling agent such as γ-glycidoxypropyltrimetboxysilane or γ-aminopropyltriethoxysilane;

an oxetane compound such as 3-methyl-3-oxetane methanol, 3-ethyl-3-oxetane methanol, 3-butyl 3-oxetane methanol, 3-methyl-3-oxetane ethanol, 3-ethyl-3-oxetane ethanol, 3-butyl 3-oxetane ethanol, 3-chloromethyl-3-methyloxetane, 3-chloromethyl-3-ethyloxetane, or a polyvalent oxetane compound; and a cyclic urea compound such as 2 imidazolidinone.

As the polyhydric alcohol, a polyhydric alcohol having 2 to 8 carbon atoms is preferable, a polyhydric alcohol having 3 to 6 Carbon atoms is more preferable, and a polyhydric alcohol having 3 or 4 carbon atoms is still more preferable. Further, a diol is preferable, and examples thereof include ethylene glycol, propylene glycol, 1,3-propanediol, and 1,4-butanediol. A polyhydric alcohol selected from propylene glycol, 1,3-propanediol, and 1,4-butanediol is preferable.

Further, as the epoxy compound, a polyglycidyl compound is preferable, and ethylene glycol diglycidyl ether is suitably used.

As the oxazoline compound, 2-oxazolidinone is suitably used.

As the alkylene carbonate compound, 1,3-dioxolan-2-one (that is, ethylene carbonate) is suitably used.

Furthermore, two or more compounds selected from the polyhydric alcohol compound, the epoxy compound, the oxazoline compound, and the alkylene carbonate compound are preferably used in combination. From the viewpoint of higher physical properties, a combination of a polyhydric alcohol and the organic surface crosslinking agent other than the polyhydric alcohol is preferable, a combination of a polyhydric alcohol and an epoxy compound or an alkylene carbonate compound is more preferable, and a combination of a polyhydric alcohol and an alkylene carbonate compound is still more preferable.

In a case where a plurality of the organic surface crosslinking agents are combined, particularly in a combination of the polyhydric alcohol and the organic surface crosslinking agent other than the polyhydric alcohol, the ratio (the weight ratio) is, which is expressed as polyhydric alcohol any compound other than polyhydric alcohol, preferably 1:100 to 100:1, more preferably 1:50 to 50:1, and still more preferably 1:30 to 30:1.

(Solvent and Concentration)

The total amount of the organic surface crosslinking agent added is preferably 0.001 parts by weight to 15 parts by weight and more preferably 0.01 parts by weight to 5 parts by weight with respect to 100 parts by weight of the water-absorbing resin powder before addition.

Further, in a case where two kinds of the compounds, that is, a polyhydric alcohol compound and a compound other than the polyhydric alcohol are used as the organic surface crosslinking agent, the total amount of the polyhydric alcohol compound is preferably 0.001 parts by weight to 10 parts by weight and more preferably 0.01 parts by weight to 5 parts by weight with respect to 100 parts by weight of, the water-absorbing resin powder before addition.

Further, the total amount of the compound other than the polyhydric alcohol is preferably 0.001 parts by weight to 10 parts by weight and more preferably 0.01 parts by weight to 5 parts by weight with respect to 100 parts by weight of the water-absorbing resin powder.

The organic surface crosslinking agent is preferably added as an aqueous solution. The amount of water used for the aqueous solution is preferably 0.5 parts by weight to 20 parts by weight and more preferably 0.5 part by weight to 10 parts by weight as the total amount with respect to 100 parts by weight of the water-absorbing resin powder before the addition treatment. Incidentally, the amount of water also includes crystal water, hydrated water, and the like of the surface crosslinking agent.

Furthermore, a hydrophilic organic solvent may be added to the aqueous organic surface crosslinking agent solution. In this case, the amount of the hydrophilic organic solvent is preferably more than 0 parts by weight and 10 parts by weight or less, and more preferably more than 0 parts by weight and 5 parts by weight or less with respect to 100 parts by weight of the water-absorbing resin powder before the addition treatment. Examples of the hydrophilic organic solvent include a primary alcohol having 1 to 4 carbon atoms, especially a primary alcohol having 2 or 3 carbon atoms, and a lower ketone having 4 or less carbon atoms such as acetone. Particularly, a volatile alcohol having a boiling point of lower than 150° C., more preferably lower than 100° C., is preferable because the volatile alcohol evaporates during a surface crosslinking treatment and no residue is left.

Specific examples thereof include lower alcohols such as methyl alcohol, ethyl alcohol, n-propyl alcohol, isopropyl alcohol, n-butyl alcohol, isobutyl alcohol, and t-butyl alcohol; ketones such as acetone; ethers such as dioxane, tetrahydrofuran, and methoxy (poly)ethylene glycol; amides such as ε-caprolactam and N,N-dimethylformamide; sulfoxides such as dimethyl sulfoxide; and polyhydric alcohols such as polyoxypropylene and oxyethylene-oxypropylene block copolymers.

Further, upon mixing a surface crosslinking agent solution to the water-absorbing resin powder, water-insoluble fine particles or a surfactant may be present together within a range not impairing the effect of the present invention, in an amount of more than 0 parts by weight and 10 parts by weight or less, preferably more than 0 parts by weight and 5 parts by weight or less, and more preferably more than 0 parts by weight and 1 part by weight or less with respect to 100 parts by weight of the water-absorbing resin powder before the addition treatment. In this case, a surfactant used or the like is disclosed in U.S. Pat. No. 7,473,739 or the like.

The concentration of the surface crosslinking agent in the aqueous surface crosslinking agent solution is determined appropriately, and is 1 wt % to 80 wt %, 5 wt % to 60 wt %, 10 wt % to 40 wt %, or 15 wt % to 30 wt % from the viewpoint of physical properties. As the remnant, the hydrophilic organic solvent or other components are contained.

The temperature of the aqueous organic surface crosslinking agent solution is determined appropriately from the solubility of the organic surface crosslinking agent used, the viscosity of the aqueous solution, and the like, and is preferably in a range of −10° C. to 100° C., more preferably in a range of 5° C. to 70° C., still more preferably in a range of DC to 65° C., and particularly preferably in a range of 25° C. to 50° C.

A high temperature is not preferable because a cyclic compound may be hydrolyzed (for example, decomposition from ethylene carbonate to ethylene glycol or decomposition from oxazolidinone to ethanol amine), water or a hydrophilic organic solvent may evaporate to reduce a miscibility, or the like, before mixing or reaction with the water-absorbing resin powder. Further, a too low temperature is not preferable because the surface crosslinking agent solution may be solidified or the surface crosslinking agent may be precipitated.

(Combined Use of Acid or Base in Surface Crosslinking Agent Solution)

In order to accelerate a reaction or uniform mixing of a surface crosslinking agent, the surface crosslinking agent solution may contain an acid or a base in addition to the organic surface crosslinking agent, the hydrophilic organic solvent, the surfactant, and the water-insoluble fine particles.

As the acid or the base, an organic acid or a salt thereof, an inorganic acid or a salt thereof, and an inorganic base are used, and are used appropriately in an amount of 0 parts by weight to 10 parts by weight, preferably 0.001 parts by weight to 5 parts by weight, and more preferably 0.01 parts by weight to 3 parts by weight with respect to 100 parts by weight of the water-absorbing resin powder before the addition treatment. Examples of the organic acid include a water-soluble organic acid having 1 to 6 carbon atoms, preferably 2 to 4 carbon atoms, and a water-soluble saturated organic acid, particularly a saturated organic acid having a hydroxyl group.

Other examples thereof include a non-crosslinkable water-soluble inorganic base (preferably, an alkali metal salt, an ammonium salt, an alkali metal hydroxide, and ammonia or a hydroxide thereof) and a non-reducing alkali metal salt pH buffer (preferably a hydrogen carbonate, a dihydrogen phosphate, a hydrogen phosphate, and the like).

(Method for Adding Organic Surface Crosslinking Agent Solution)

The organic surface crosslinking agent is added to the water-absorbing resin powder by an addition treatment. A method for the addition treatment is not particularly limited. Examples thereof include a method for immersing water-absorbing resin powder in a hydrophilic organic solvent such that the added crosslinking agent is adsorbed thereby, and a method for spraying or dropwise adding a crosslinking agent solution directly to water-absorbing resin powder and mixing. The latter method is preferable from the viewpoint of adding a predetermined amount uniformly. Furthermore, for the uniform addition, the addition treatment is preferably performed while water-absorbing resin powder is stirred, and further the organic surface crosslinking agent solution is preferably sprayed.

In the addition treatment, two or more kinds of the added crosslinking agents having different compositions may be added simultaneously, for example, by using different spraying nozzles. However, a single composition is more preferable from the viewpoint of uniformity and the like. Further, in the case of a single composition, a plurality of spraying nozzles may be used, considering the size of the addition treatment apparatus, the treatment amount thereof, the spraying angle of the spraying nozzle, or the like.

As an apparatus for use in the addition treatment (hereinafter, referred to as a mixing apparatus in some cases), for example, a cylindrical mixer, a double-wall conical mixer, a V-shaped mixer, a ribbon type mixer, a screw type mixer, a fluidization type furnace, a rotary disc mixer, an air current type mixer, a double-arm kneader, an internal mixer, a pulverizing type kneader, a rotary mixer, a screw extruder, Turbulizer, a ploughshare mixer, or the like are suitably used. Further, in large-scale production such as commercial production, the mixing apparatus is preferably an apparatus capable of performing continuous mixing. Furthermore, one and the same apparatus may be used in each of the addition treatments, or separate, apparatuses may be used in the addition treatments.

The water-absorbing resin powder to be provided in the present step is preferably heated or warmed. The temperature of the water-absorbing resin powder is preferably in a range of 10° C. to 100° C., more preferably in a range of 15° C. to 80° C., and still more preferably in a range of 20° C. to 70° C.

This temperature of 10° C. or higher is preferable because precipitation of the surface crosslinking agent, moisture absorption of the water-absorbing resin powder or the like is suppressed and the surface treatment is performed sufficiently and uniformly. Further, this temperature of 100° C. or lower is preferable because evaporation of water from the aqueous surface crosslinking agent solution is suppressed and a risk such as precipitation of the surface crosslinking agent is reduced.

(2-6-2) Heat Treatment Step

This is a step for performing a heat treatment to perform a crosslinking treatment on the surface or the vicinity of the surface of the water-absorbing resin powder in order to improve fluid retention capacity under pressure or GCA of the water-absorbing resin particles. In this regard, an excessive surface crosslinking treatment may lower CRC too much. Therefore, this step is preferable to perform the surface crosslinking treatment until CRC is 28 g/g or more.

The preferable degree of the surface crosslinking can be confirmed by a decrease width of CRC before and after surface crosslinking, therefore the amount of the surface crosslinking agent and the reaction temperature/time may be appropriately selected such that a decrease of CRC caused by surface crosslinking is 0.5 g/g or more, and further 1 g/g to 20 g/g and 2 g/g to 15 g/g.

The heat treatment step may be performed simultaneously with or after the step for adding a surface crosslinking agent, and is preferably performed after the step for adding a surface crosslinking agent. Further, this step may be performed once, or may be performed multiple times under the same or different conditions.

The water-absorbing resin particles dried obtained until the step (2-5) has a granulated form. However, before surface crosslinking, the water-absorbing resin particles are in the form of the granulated particles which include primary particles adhered physically each other, and in some cases, the granulated form may be collapsed during swelling to be fragmented and water absorption performance and liquid permeability ability may be degraded.

However, by carrying out this surface crosslinking step, the crosslink density in the vicinity of the surface of the granulated particle is increased and further, primary particles (gel particles obtained in the gel-crushing step) that form the granulated particles are, chemically bound so that crosslinking between particles is also achieved while the adhesion of the primary particles is loose or in point contact with each other. Thus, the particles after surface crosslinking are difficult to collapse during swelling and thus the object of the present invention is achieved.

In this way, in the present invention, not only addition of the adhesion controlling agent but also combination with the surface crosslinking step have significance.

(Heating Apparatus)

A heating apparatus as used in the present invention is exemplified by a continuous or batch type heating apparatus including a known drier or a known heating furnace and a gas discharge structure and/or a gas supply structure for obtaining a predetermined atmosphere a predetermined atmosphere, and is suitably a continuous type heating apparatus. As the heating method of the heating apparatus, a conductive heat transfer type, a radiative heat transfer type, a hot-air heat transfer type, or a dielectric heating type are advantageous. The conductive heat transfer type and/or a hot-air heat transfer type heating method are more, and the conductive heat transfer type heating method is still more preferable.

The so-called controlled temperature of the heating apparatus may be any temperature at which the water-absorbing resin powder can be heated to a temperature to be described later, and it is not necessary for the control temperature to be constant from the beginning to the end of the process. However, in order to prevent partial overheating or the like, the control temperature of the heating apparatus is preferably 50° C. to 300° C. In a case where damage resistance is regarded as important among the physical properties of the resulting water-absorbing resin particles and water-absorbing agent, the controlled temperature is more preferably 250° C. or lower, still more preferably 70° C. to 230° C., and still more preferably 90° C. to 220° C.

On the other hand, in a case where the water absorption performance is regarded as important, the controlled temperature is more preferably 120° C. to 280° C., still more preferably 150° C. to 250° C., and particularly preferably 170° C. to 230° C.

Further, the heating time is preferably 1 minute to 180 minutes, more preferably 5 minutes to 120 minutes, still more preferably 10 minutes to 120 minutes, and still more preferably 15 minutes to 60 minutes. When the time for the heat treatment is shorter than 1 minute, the surface crosslinking treatment is not sufficient so that the fluid retention capacity under pressure (AAP) is decreased. On the other hand, when the time for the heat treatment is too long, coloration may occur or the fluid retention capacity without pressure (CRC) may be excessively decreased.

Further, in order to enhance the efficiency of heating and perform a uniform heat treatment, it is preferable to use an apparatus including a structure for continuously stirring and/or fluidizing the heating object. A stirring and/or a fluidizing method is preferably a groove stirring method, a method of a screw type, a method of a rotary type, a method of a disc type, a method of a kneading type, a method of a fluidized tank type, and the like, and more preferably a stirring method using stirring blades (paddles) and a stirring method based on movement of a heat transfer surface itself such as a rotary retort furnace. Incidentally, the stirring and/or fluidizing structure aims perform a uniform heat treatment, and therefore need not to be used in a case where the treated amount is small, for example, in a case where the drying object has a thickness of less than 1 cm.

The discharge structure corresponds to an air exit. If gas is discharged from an outlet of a heated product, the outlet also corresponds to the discharge mechanism. Further, it is preferable that the discharge structure adjust the amount of gas discharged therefrom and a pressure of the gas discharged therefrom by means of a blower or the like. Furthermore, an air exit point is not limited to one air exit point. A plurality of air exit points can be provided in consideration of the size of the heating apparatus and an adjustment status of the dew point and temperature. The heating apparatus includes the gas supply structure and can also control an atmospheric dew point and an atmospheric temperature in the heating portion by adjusting the structure, for example, by adjusting the amount of gas supplied.

It is preferable that the gas pressure of the heating portion be slightly lower than a normal pressure. Such a differential pressure is preferably in a range of 0 kPa to −10 kPa, more preferably in a range of 0 kPa to −5 kPa, and still more preferably in a range of 0 kPa to −2 kPa with respect to atmospheric pressure. In making industrial continuous production, it is possible to use a batch processing-type or continuous processing-type heating apparatus including the above structure.

Incidentally, when the addition treatment of an additive is performed before or after the heat treatment or before and after the heat treatment, one and the same apparatus as used in the above addition treatment may be used in these addition treatments. Alternatively, separate apparatuses may be used in these addition treatments. Particularly, in a case where a production apparatus of continuous type is used, it is preferable in terms of production efficiency that one and the same apparatus be used both in the addition treatment performed before heating and the heat treatment while another apparatus is used in the addition treatment performed after heating.

Further, for the purpose of preventing the occurrence of excessive crosslinking reaction and improving handling property in a subsequent step, the water-absorbing resin particles taken out of the heating apparatus may be cooled, as required, to a temperature of preferably lower than 100° C., and more preferably 0° C. to 95° C. or 40° C. to 90° C.

(2-7) Addition of Liquid Permeability Enhancer (Step (vii))

This is a step for adding a liquid permeability enhancer for increasing FGBP and is preferably performed during or after the surface crosslinking step.

(Liquid Permeability Enhancer)

The liquid permeability enhancer in the present invention is an additive selected from insoluble fine particle compounds and polyvalent cationic compounds or an additive for increasing FGBP as compared with a case where no liquid permeability enhancer is used.

The water-insoluble fine particle compound and the cationic compound in the present invention serve as a stereoscopic spacer or an electrostatic spacer on the surface of the water-absorbing resin particles. The water-insoluble fine particle compound and the cationic compound cause the resulting water-absorbing agent to have "increased liquid permeability (for example, FGBP increased by $10 \times 10^{-9}$ cm$^2$ or more, preferably $30 \times 10^{-9}$ cm$^2$ or more, and more preferably $50 \times 10^{-9}$ cm$^2$ or more as compared with FGBP obtained when these compounds are not used)."

Besides, these additives, depending on their kinds, can achieve effects such as "Anti-Caking," "deodorization/antibacterial activity," and "reduction of a residual surface crosslinking agent," but their effects and intended uses are not particularly limited in the present invention.

The liquid permeability enhancer essentially added in the production method according to the present invention is preferably selected from water-insoluble inorganic fine particles and polyvalent cationic compounds (cationic polymer compounds or water-soluble polyvalent metal cation-containing compounds).

According to the preferred embodiment of the present invention, the liquid permeability enhancer corresponds to the water-insoluble inorganic fine particles. According to such an embodiment, technical effectiveness of improvement in liquid permeability is achieved.

The "water soluble" compound used in the present specification refers to a compound that dissolves in an amount of 1 g or more or 5 g or more with respect to 100 g of water at 25° C. The "water insoluble" compound refers to a compound that dissolves in only an amount of less than 1 g, less than 0.5 g or less than 0.1 g with respect to 100 g of water at 25° C.

In the present invention, while the organic surface crosslinking agent crosslinks with a functional group of the water-absorbing resin powder by covalent bond, the polyvalent cationic compound (cationic polymer compound or water-soluble polyvalent metal cation-containing compound), which is preferably used as the liquid permeability enhancer in the present invention, is assumed to crosslink with the water-absorbing resin powder or the water-absorbing resin particles by ion crosslinking or is assumed to serve as a stereoscopic spacer or an electrostatic spacer, thereby improving liquid permeability.

(Inorganic Fine Particles)

Examples of the inorganic fine particles include: water-insoluble fine particulate inorganic powder such as silicon dioxide, titanium dioxide, aluminum oxide, magnesium oxide, zinc oxide, talc, metal phosphate (for example, calcium phosphate, barium phosphate, and aluminum phosphate), metal borate (for example, titanium borate, aluminum borate, iron borate, magnesium borate, manganese borate, and calcium borate), silicic acid or a salt thereof, clay, diatomaceous earth, zeolite, bentonite, kaolin, hydrotalcite, and activated clay; and organic fine powder such as calcium lactate, aluminum lactate, and a metal soap (polyvalent metal salt of long chain fatty acid). The volume average particle diameter of the inorganic fine particles is preferably 10 μm or less and more preferably 1 μm or less.

The inorganic fine particles may be mixed in the form of powder with the water-absorbing resin powder or the water-absorbing resin particles or may be mixed in the form of a water dispersion (slurry, for example, colloidal silica) with the water-absorbing resin powder or the water-absorbing resin particles. Alternatively, the inorganic fine particles may be mixed in the form of being dispersed in the surface crosslinking agent or the aqueous solution of the surface crosslinking agent with the water-absorbing resin particles.

(Cationic Polymer Compound)

The cationic polymer compound is not particularly limited, but cationic polymer compounds described in U.S. Pat. Nos. 5,382,610, 7,098,284, WO 2009/110645 A, WO 2009/041731 A, and WO 2009/041727 A can be suitably used.

Among the compounds described in the above-listed documents, the cationic polymer compound in the present invention is preferably polyethylene imine, polyvinyl amine, polyallylamine, or a condensate of dimethylamine/ammonia/epichlorohydrin.

As for a molecular weight of the cationic polymer compound, a weight average molecular weight is preferably 1,000 to 5,000,000, more preferably 2,000 to 1,000,000, and still more preferably 10,000 to 500,000.

The cationic polymer compound is preferably water soluble from the viewpoint of facilitating mixing. Here, the term "water soluble" means to be able to dissolve in an amount of 1 g or more with respect to 100 g of water at 25° C.

The cationic polymer compound may be directly mixed with the water-absorbing resin particles or may be mixed in the form of a solution, particularly in the form of an aqueous solution. Alternatively, the cationic polymer compound may be mixed in the form of being dissolved in the surface crosslinking agent or in the aqueous solution of the surface crosslinking agent.

(Water-Soluble Polyvalent Metal Cation-Containing Compound)

The water-soluble polyvalent metal cation-containing compound refers to a compound containing a bivalent or higher metal cation, preferably a trivalent or higher metal cation. The trivalent or higher metal cation is exemplified by aluminum, zirconium, and titanium. Among these, aluminum is preferable.

Examples of the polyvalent metal cation-containing compound include polyvalent metal compounds, which are inorganic surface crosslinking agents, including inorganic salts of polyvalent metals such as aluminum sulfate, aluminum chloride, zirconium chloride oxide, zirconium ammonium carbonate, zirconium potassium carbonate, zirconium potassium carbonate, zirconium sulfate, zirconium acetate, and zirconium nitrate; and organic salts of polyvalent metals such as aluminum acetate, aluminum lactate, hydroxy zirconium chloride, titanium triethanol aminate, and titanium lactate.

Among these as the polyvalent metal cation, a compound containing aluminum is preferable.

These compounds may be directly mixed in the form of powder with the water-absorbing resin particles, may be mixed in the form of a solution or a dispersion, particularly in the form of an aqueous solution, or may be mixed in the form of being dissolved in the surface crosslinking agent or the aqueous solution of the surface crosslinking agent.

In the production method according to the present invention, the water-soluble polyvalent metal cation-containing compound may be added twice or more times. For example, in a case where the water-soluble polyvalent metal cation-containing compound is added twice, a ratio between a first addition and a second addition (a first addition/a second addition) is defined in a range of 1/99 to 99/1 and preferably in a range of 10/90 to 90/10. A ratio falling outside the above ranges is not preferable because it is extremely close to one-time addition, which reduces effectiveness of a plurality of additions.

In the meantime, a non-metallic ion crosslinking agent such as a cationic polymer compound may express tackiness at the aforementioned mixing. Therefore, the addition of the non-metallic ion crosslinking agent is preferably performed after the last heat treatment.

In a case where a solvent is used for mixing of the water-soluble polyvalent metal cation-containing compound, the solvent is preferably water or the aqueous crosslinking agent solution. For improvement in dispersity, solubility, and blendability, water may be used in combination with a hydrophilic organic solvent (alcohol or polyglycol) or a surfactant, if necessary.

The amount of water used is appropriately determined according to a kind of additive and an addition method, for example, the amount of water used is 0 parts by weight (drying blending) to 50 parts by weight, 0.1 parts by weight to 10 parts by weight, or 0.5 parts by weight to 5 parts by weight with respect to 100 parts by weight of the water-absorbing resin particles.

Further, as a liquid permeability enhancer other than the above liquid permeability enhancers, a water-soluble polysiloxane described in WO 2009/093708 A, primary to tertiary amine compounds described in WO 2008/108343 A, or the like are preferably used.

The amount of the liquid permeability enhancer is preferably 0.001 parts by weight to 5 parts by weight, more preferably 0.002 parts by weight to 2 parts by weight, and still more preferably 0.005 parts by weight to 1 part by weight with respect to 100 parts by weight of the water-absorbing resin particles to be added.

Incidentally, for the water-soluble polyvalent metal cation-containing compound, these values are expressed in terms of the amount of polyvalent metal cation (for example, for the aluminum sulfate, it is a value based on the amount of $Al^{3+}$).

Further, as for the addition timing, the liquid permeability enhancer is appropriately added after pulverization and before surface crosslinking, during surface crosslinking, or after surface crosslinking.

(2-8) Step for Adding Other Additives

This is a step for adding other additives in order to provide various functions to the water-absorbing resin powder or the surface crosslinked water-absorbing resin particles and includes one or two or more steps. Examples of the additives include a deodorant, a perfume, antimicrobial agent, a foaming agent, a chelating agent such as trisodium diethylenetriamine pentaacetate, or pentasodium diethylenetriamine pentaacetate, a surfactant, a coloring preventing agent, a pigment, a dye, a fertilizer, an oxidizing agent, a reducing agent and the like, these additives can provide or enhance functions. Further, as for addition of the additives, the additives may be added in a state of a solution or added by dry blending.

This step may be performed between any steps of the steps (i) to (vii), and may be simultaneously performed with any steps of the steps (i) to (vii). Preferably, this step is performed during the step (vi) or after the step (vi).

The proportion of these additives used is less than 10 wt %, preferably less than 5 wt %, and more preferably less than 1 wt % of the water-absorbing resin powder or the surface crosslinked water-absorbing resin particles. Further, these additives may be simultaneously added with the surface crosslinking step or may be separately added from the surface crosslinking step.

In the production method of the present invention, the resulting polyacrylic acid (salt)-based water-absorbing agent is adjusted to have a surface tension of 60 mN/m or more and fluid retention capacity without pressure of 28 g/g or more.

In order to adjust the fluid retention capacity without pressure to 28 g/g or more, it is preferable to control the crosslink density by the drying temperature and time of the hydrogel or the degree of the surface crosslinking of the water-absorbing resin powder. Further, it is preferable to control the surface tension by the type of an additive and the amount of an additive added.

According to the preferred embodiment of the present invention, by adjusting the fluid retention capacity without pressure (CRC) and the surface tension of the water-absorbing agent to be in a specific range, it is possible to achieve excellent Gel Capillary Absorption (GCA) and Free Gel Bed Permeability (FGBP) and to efficiently achieve the desired object of the present invention.

[3] Physical Properties of Poly(Meth)Acrylic Acid (Salt)-Based Particulate Water-Absorbing Agent In the present invention, there is also provided a particulate water-absorbing agent containing polyacrylic acid (salt)-based water-absorbing resin particles as a main component, the particulate water-absorbing agent satisfying the following (1) to (5).

That is, the particulate water-absorbing agent is a polyacrylic acid (salt)-based particulate water-absorbing agent containing polyacrylic acid (salt)-based water-absorbing resin particles as a main component and satisfying the following (1) to (5): (1) a fluid retention capacity without pressure (CRC) is 28 g/g or more; (2) GCA is 28.0 g/g or more; (3) FGBP satisfies, in a case where GCA is in a range of 28.0 g/g or more and less than 36.0 g/g, mathematical formula: (FGBP=$-10\times10^{-9}$ GCA+$380\times10^{-9}$) cm² or more, and FGBP is, in a case where GCA is 36.0 g/g or more, $30\times10^{-9}$ cm² or more; (4) a weight average particle diameter (D50) of the particulate water-absorbing agent is 300 μm to 500 μm; and (5) a surface tension is 60 mN/m or more.

Incidentally, the water-absorbing agent of the present invention is not limited by the production method of the present invention as long as it satisfies the above (1) to (5).

(3-1) Above Physical Property (1) of Water-Absorbing Agent; Fluid Retention Capacity Without Pressure (CRC)

The fluid retention capacity without pressure (CRC) of the particulate water-absorbing agent of the present invention is controlled to be 28 g/g or more, more preferably 29 g/g or more, still more preferably 30 g/g or more, particularly preferably 31 g/g or more, and most preferably 32 g/g or more by appropriately producing internal crosslinking or surface crosslinking with the above-described production method.

A higher CRC is preferable and there is no particular limitation on the upper limit thereof. However, from the viewpoint of a balance with other physical properties (particularly, liquid permeability), CRC is preferably 50 g/g or less, more preferably 45 g/g or less, and still more preferably 42 g/g or less.

CRC can be controlled by adjusting the type and the amount of a crosslinking agent during polymerization or in surface crosslinking in the ranges described in the above (2-1) to (2-6).

In order to achieve the range of GCA according to the present invention, it is preferable to control the fluid retention capacity without pressure (CRC) in the above-described ranges.

(3-2) Above Physical Property (2) of Water-Absorbing Agent; Gel Capillary Absorption (GCA)

GCA evaluates liquid absorption ability under a load of 0.05 psi for 10 minutes with a difference in height of 10 cm between the upper surface of a glass filter and the meniscus at the lower portion of a Mariotte tube. GCA evaluates absorption ability for as short time as 10 minutes. The conventionally known fluid retention capacity under pressure (AAP) or FHA described in U.S. Pat. No. 7,108,916 evaluates absorption ability in a saturation state for 1 hour, and thus is an evaluation method based on a different idea from GCA according to the present invention. A higher value of GCA of a particulate water-absorbing agent improves the ability of absorbing urea from pulp in a disposable diaper, can reduce a re-wet amount, and can suppress skin rash or urine leakage.

The value of GCA of the particulate water-absorbing agent of the present invention is calculated by the method described in Examples below. A higher value thereof indicates better performance, and higher values of 28.0 g/g or more, 29.0 g/g or more, and 30.0 g/g or more in this order are preferable. The value is more preferably 31.0 g/g or more, still more preferably 31.5 g/g or more, still more preferably 33 g/g or more, and most preferably 34 g/g or more. A higher upper limit of GCA is more preferable. However, the upper limit of GCA is usually preferably about 50.0 g/g from the viewpoint of a balance with other physical properties.

Therefore, according to the preferred embodiment of the present invention, GCA is 31.0 g/g or more. According to such an embodiment, the re-wet amount of liquid can be decreased and the technical effect of improving the speed of absorbing liquid is achieved.

Incidentally, in the preset invention, it is particularly important that GCA is in the above range. In addition, it is preferable that the fluid retention capacity under pressure is high, and the water absorption speed is high (the water absorption time by the Vortex method is short).

(3-3) Physical Property (3) of Water-Absorbing Agent; FGBP

FGBP is a method of evaluating physiological saline solution penetrating ability of the gel layer after a physiological saline solution is poured from the upper portion of the gel layer in a state where a load of 0.3 psi is applied to the water-absorbing agent layer freely swollen in a cell having a mesh structure on the bottom surface. When a value of FGBP is higher, the speed of absorbing liquid and the re-Wet amount in the absorbent material having a high concentration of the absorbing agent can be decreased.

In the present invention, in a case where GCA is in a range of 28.0 g/g or more and less than 35.0 g/g, it is preferable to satisfy FGBP $\geq -10 \times 10^{-9} \times GCA + 380 \times 10^{-9}$ cm$^2$ (formula 1)

Further, in the case of GCA $\geq 35.0$ g/g, it is preferable to satisfy FGBP $\geq 30 \times 10^{-9}$ cm$^2$, more preferable to satisfy FGBP $\geq 50 \times 10^{-9}$ cm$^2$, and still more preferable to satisfy FGBP $\geq 75 \times 10^{-9}$ cm$^2$.

Meanwhile, in consideration of only FGBP, it is more preferable to satisfy FGBP $\geq 100 \times 10^{-9}$ cm$^2$, still more preferable to satisfy FGBP $\geq 120 \times 10^{-9}$ cm$^2$, still more preferable to satisfy FGBP $\geq 140 \times 10^{-9}$ cm$^2$, still more preferable to satisfy FGBP $\geq 160 \times 10^{-9}$ cm$^2$, particularly preferable to satisfy FGBP $\geq 200 \times 10^{-9}$ cm$^2$, and most preferable to satisfy FGBP $\geq 300 \times 10^{-9}$ cm$^2$. A higher upper limit of FGBP is more preferable, but the upper limit of FGBP is usually preferably about $500 \times 10^{-9}$ cm$^2$ from the viewpoint of a balance with other physical properties.

Incidentally, in the preset invention, it is particularly important that FGBP is in the above range. In addition, it is preferable that the fluid retention capacity under pressure is high, and the water absorption speed is high (the water absorption time by the Vortex method is short).

(3-4) Physical Property (4) of Water-Absorbing Agent; Particle Size

The weight average particle diameter (D50) of the particulate water-absorbing agent of the present invention is preferably 300 μm to 500 μm, more preferably 310 μm to 480 μm, and still more preferably 320 μm to 450 μm.

Therefore, according to the preferred embodiment of the present invention, the weight average particle diameter (D50) of the polyacrylic acid (salt)-based particulate water-absorbing agent is 300 μm to 500 μm. According to such an embodiment, GCA, FGBP, and the fluid retention capacity under pressure can be improved.

As for other preferred particle size characteristics, the amount of fine particles, which have a particle diameter of less than 150 μm, contained in the particulate water-absorbing agent is preferably 0 wt % to 5 wt %, more preferably 0 wt % to 3 wt %, and still more preferably 0 wt % to 2 wt % in 100 wt %.

Furthermore, the amount of coarse particles, which have a particle diameter of 850 μm or more, contained in the particulate water-absorbing agent is preferably 0 wt % to 5 wt %, more preferably 0 wt % to 3 wt %, and still more preferably 0 wt % to 1 wt % of the whole particles.

Further, the proportion of particles having a particle diameter of 150 μm or more and less than 850 μm in the particulate water-absorbing agent is preferably 90 wt % or more, more preferably 95 wt % or more, still more preferably 98 wt % or more, and particularly preferably 99 wt % or more (the upper limit is 100 wt %) of the whole particles.

Further, the logarithmic standard deviation ($\sigma\zeta$) of the particle size distribution of the particulate water-absorbing agent is preferably 0.20 to 0.50, more preferably 0.25 to 0.45, and still more preferably 0.30 to 0.40.

(3-5) Physical Property (5) of Water-Absorbing Agent; Surface Tension

The surface tension (specified by the measurement method in Examples) of the particulate water-absorbing agent of the present invention is 60 mN/m or more, more preferably 61 mN/m or more, still more preferably 62 mN/m or more, and may be 63 MN/m or more or 64 mN/m or more. Usually, as the upper limit, 75 mN/m is enough.

Conventionally, when a large amount of a surfactant or a hydrophobic substance (for example, 0.1 to 10 wt %) is used during gel-crushing in order to control the water absorption speed as in Literature 13, there have been problems that the surface tension of the obtained water-absorbing resin particles is lowered (particularly less than 60 mN/m, furthermore less than 55 mN/m) and that the re-wet amount of a disposable diaper is increased.

In the present invention, it is particularly important to control the surface tension in the above range. Therefore, as the control method, the surface tension can be controlled by adjusting the structure, (LB, and the addition amount of the adhesion controlling agent described in the above (2-3-2) in the above-described ranges.

Incidentally, the method for controlling the surface tension of the particulate water-absorbing agent of the present invention to 60 mN/m or more is not particularly limited, but a method of adjusting the type and the addition amount of the adhesion controlling agent or the like is exemplified.

(3-6) More Preferred Physical Property (1); Fluid Retention Capacity Under Pressure (AAP)

As described in Examples below, the fluid retention capacity under pressure of the particulate water-absorbing agent of the present invention is specified as a fluid retention capacity with respect to a 0.90 wt % aqueous sodium chloride solution under a pressure of 2.06 kPa, and is controlled to preferably 24 g/g or more, more preferably 25 g/g or more, still more preferably 26 g/g or more, particularly preferably 27 g/g or more, and most preferably 28 g/g or more.

A higher upper limit of AAP is more preferable, but the upper limit of AAP is usually preferably about 40 g/g from the viewpoint of a balance with other physical properties.

If GCA is improved within the range specified in the present invention and the fluid retention capacity under pressure (AAP) can be controlled in the above range, performance of a disposable diaper can be further improved.

(3-7) More Preferred Physical Property (2); Water Absorption Time (Vortex Method)

The water absorption time (Vortex method) of the particulate water-absorbing agent of the present invention is preferably 40 seconds or shorter, more preferably 35 seconds or shorter, still more preferably 30 seconds or shorter, still more preferably 28 seconds or shorter, still more preferably 26 seconds or shorter, still more preferably 24 seconds or shorter, particularly preferably 22 seconds or shorter, and most preferably 19 seconds or shorter.

When GCA and FGBP are improved within the range specified in the present invention and the water absorption time (Vortex method) can be controlled in the above range, performance of a disposable diaper can be further improved.

(3-8) More Preferred Physical Property (4); Moisture Content

The moisture content (specified by an weight lost from drying at 180° C.×3 hours) of the particulate water-absorbing agent of the present invention is not particularly limited as long as it satisfies the above-described physical properties, but is adjusted to 0.1% to 20%, further 1% to 15%, and particularly 2% to 10%. When the moisture content is high, physical properties are difficult to satisfy. When the moisture content is low, the water absorption speed tends to be decreased and abrasion resistance of particles tends to deteriorate.

According to the preferred embodiment of the present invention, one or more compounds selected from a nonionic substance, an amphoteric substance, an anionic substance, and a cationic substance are contained in the inside and/or the surface of the polyacrylic acid (salt)-based particulate water-absorbing agent, the nonionic substance is (a) a polyol, (b) a hydroxy group-modified product of a polyol, (c) side-chain and/or terminal polyether-modified polysiloxane, or (d) an alkylene oxide adduct of higher aliphatic amine, the amphoteric substance is (e) alkylaminobetaine or (f) alkylamine oxide, the anionic substance is (g) a sulfuric acid ester salt of a higher alcohol alkylene oxide adduct or (h) alkyl diphenyl ether disulfonate, and the cationic substance is (i) an ammonium salt.

According to the preferred embodiment of the present invention, the polyacrylic acid (salt)-based particulate water-absorbing agent further contains the liquid permeability enhancer. According to such an embodiment, the technical effect of improving liquid permeability is achieved.

[4] Absorbent Article

An application of the particulate water-absorbing agent of the present invention is not particularly limited. The particulate water-absorbing agent of the present invention is preferably used for an absorbent body used for disposable diapers or sanitary napkins.

In the present invention, an absorbent material means an absorbing material formed by using the particulate water-absorbing agent of the present invention and a hydrophilic fiber as a main component. In the absorbent material of the present invention, the amount of the particulate water-absorbing agent contained (core concentration) is preferably 20 wt % to 100 wt %, more preferably 30 wt % to 95 wt %, and particularly preferably 50 wt % to 90 wt % with respect to the total weight of the particulate water-absorbing agent and the hydrophilic fiber. As described above, in the case of using a water-absorbing agent having improved GCA, there are problems that the effect of reducing the re-wet amount is exerted in the absorbent material containing a water-absorbing agent in a small amount (less than 20 wt %), however, in a high-concentration absorbent material or an absorbent material without use of pulp, the expected effect is not always recognized in view of the speed of absorbing liquid and the re-wet amount. On the other hand, in the present invention, by highly achieving a balance between GCA and FGBP, not only the speed of absorbing liquid can be improved but also the re-wet amount of liquid can be reduced even in the high-concentration absorbent material or the absorbent material without use of pulp.

Further, in a case where the absorbent material of the present invention is thin, the thickness of the absorbent material is preferably as thin as 1 mm to 5 mm. A thin absorbent article can be obtained by using such a thin absorbent material. For example, an absorbent article including the above-described thin absorbent material of the present invention, a surface sheet having liquid permeability, and a back sheet having liquid impermeability is obtained.

A method for producing a thin absorbent article of the present invention may be as follows. An absorbent article, particularly a disposable diaper or a sanitary napkin, may be formed, for example, by forming an absorbent material (absorbent core) by blending or sandwiching a fiber substrate and a particulate water-absorbing agent, sandwiching the absorbent material with a substrate such as a surface sheet having liquid permeability and a substrate such as a back sheet having liquid impermeability, and providing an elastic member, a diffusion layer, an adhesive tape, or the like, as required. Such an absorbent article is compressed and shaped so as to have a density of 0.06 g/cc to 0.50 g/cc and a basis weight of 0.01 g/cm$^2$ to 0.20 g/cm$^2$. Incidentally, examples of the fiber substrate used may include a hydrophilic fiber such as a crushed wood pulp, a cotton linter, a crosslinked cellulose fiber, rayon, cotton, wool, acetate, and vinylon. An air-laid substrate thereof is preferable.

The particulate water-absorbing agent of the present invention exhibits excellent absorption characteristics. Therefore, specific examples of the absorbent article of the present invention include a hygienic material such as disposable diapers for adults, which are significantly growing recently, diapers for children, and sanitary napkins and a so-called incontinence pads. The leakage amount or skin rash is reduced due to the particulate water-absorbing agent of the present invention in the absorbent article. Therefore, burden on a person wearing the absorbent article and nursing people can be largely reduced.

According to the preferred embodiment of the present invention, the hygienic material contains the above-described polyacrylic acid (salt)-based particulate water-absorbing agent.

[5] Comparison to Above Related Arts

Hereinbefore, although there are many parameter-controlled water-absorbing resins and the present inventors have filed Patent Literature 7 which is focused on Gel Capillary Absorption (GCA) as a new parameter as compared with the related prior arts such as Patent Literatures 1 to 6, insufficient points have still been found. In this regard, in order to solve the above-described problem, the present inventors have conducted intensive studies. As a result, liquid permeability has still been insufficient in Patent Literature 7 which is focused on Gel Capillary Absorption (GCA) as a new parameter. The present inventors have found that the above-described problem can be solved when Free Gel Bed Permeability (FGBP) as a newer index of liquid permeability is high in addition to GCA, thereby providing the new water-absorbing agent described above and the production method therefor.

While many parameter-controlled water-absorbing resins have been proposed, in conventional water-absorbing agents disclosed in Patent Literatures 1 to 6, proceeding Patent Literature 7, and the like, there is neither suggestion nor disclosure on the water-absorbing agent of the present invention in which a balance between GCA and FGBP is achieved. Further, although gel-crushing after polymerization or during polymerization in the production process for the water-absorbing resin has been often proposed in the above Patent Literatures 10 to 21, and the like, there is no disclosure in the related prior arts that an adhesion controlling agent is used, the particle diameter after gel-crushing is adjusted to be significantly small, and a liquid permeability enhancer is thereafter used.

The present invention provides a new production method in which the particle diameter after gel-crushing is adjusted to be significantly small and an adhesion controlling agent and a liquid permeability enhancer are used. Providing the new water-absorbing agent of the present invention by such a new production method described above is as described in the above specification and the following Examples.

EXAMPLES

Hereinafter, the invention is described according to the Examples but the present invention should not be construed as being limited to the Examples. Various physical properties described in the claims of the present invention or Examples were determined according to the following measurement methods (a) to (i). Incidentally, unless otherwise specified, each step in each Example was performed substantially at, a normal pressure (±5% of the atmospheric pressure, preferably within 1% thereof), and was performed without pressure change by intentionally increasing or reducing the pressure in the same step.

(a) Fluid Retention Capacity Without Pressure (CRC) (ERT441.1-02)

The fluid retention capacity without pressure (CRC) was measured in conformity with ERT441.2-02. That is, 0.200 g (weight $W0$ $(g)$) of a sample was weighed and uniformly placed in an unwoven fabric bag (60 mm×85 mm) and the bag was heat-sealed. Then, the bag was immersed in 500 mL of a 0.90 wt % aqueous sodium chloride solution, the temperature of which was adjusted to 23° C.±2° C. After 30 minutes, the bag was pulled out and drained by using a centrifugal separator (centrifuge manufactured by KOKUSAN Co., Ltd., type H-122) at 250 G for 3 minutes. Thereafter, a weight ($W1$ $(g)$) of the bag was measured. A bag containing no sample was subjected to the similar operation, and a weight ($W2$ $(g)$) of the bag was measured. The fluid retention capacity without pressure (CRC) was calculated according to the following (formula 1) based on the obtained $W0$ $(g)$, $W1$ $(g)$, and $W2$ $(g)$.

[Mathematical Formula 3]

$$\text{CRC (g/g)}\{(W1-W2)/W0\}-1 \qquad \text{(Formula 1)}$$

Gel CRC was obtained through the similar operation to above description except that 0.6 g of hydrogel particles or the crosslinked hydrogel polymer was used as a sample and a free swelling time was set to 24 hours. Furthermore, the solids content of the resin of the crosslinked hydrogel polymer or the hydrogel particles was measured separately so as to obtain a weight of the water-absorbing resin in 0.6 g of the crosslinked hydrogel polymer or the hydrogel particles. Gel CRC was calculated based on Formula (2) below. Incidentally, each sample was measured five times, and an average of values obtained by the measurement was employed.

$$\text{Gel CRC (g/g)}[(\{(mwi-mb)/msi\}- \\ 1]\times(100/Wn) \qquad \text{[Mathematical Formula 4]}$$

Incidentally, herein, msi: a weight (g) of the crosslinked hydrogel polymer or the hydrogel particles before measurement mb: a weight (g) of Blank (unwoven fabric only) which has freely swollen and been drained mwi: a total weight (g) of the crosslinked hydrogel polymer and the unwoven fabric which have freely swollen and been drained Wn: solids content (wt %) of the crosslinked hydrogel polymer or the hydrogel particles (b) Fluid Retention Capacity Under Pressure (AAP) (ERT442.2-02)

The fluid retention capacity under pressure (AAP) of the particulate water-absorbing agent according to the present invention was measured in conformity with ERT442.2-02. That is, 0.900 g (weight $W3$ $(g)$) of the particulate water-absorbing agent was put into a measurement apparatus, and the weight ($W4$ $(g)$) of the whole measurement apparatus was measured. Next, 0.90 wt % of aqueous sodium chloride solution, the temperature of which was adjusted to 23° C.±2° C., was absorbed under a load of 2.06 kPa (0.3 psi, 21 g/cm$^2$). After 1 hour, the weight ($W5$ $(g)$) of the whole measurement apparatus was measured, and the fluid retention capacity under pressure (AAP) was calculated according to the following (formula 3) based on the obtained $W3$ $(g)$, $W4$ $(g)$, and $W5$ $(g)$.

[Mathematical Formula 5]

$$\text{AAP (g/g)}=(W5-W4)/W3 \qquad \text{(formula 3)}$$

(c) Water Absorption Time (Vortex Method)

0.02 parts by weight of Food Blue No. 1 that is a food additive was added to 1,000 parts by weight of a 0.90 wt % aqueous sodium chloride solution prepared in advance, and the liquid temperature was adjusted to 30° C. 50 ml of the 0.90 wt % aqueous sodium chloride solution colored in blue was measured and put into a 100 ml beaker. 2.00 g of the particulate water-absorbing agent was put thereinto while the aqueous sodium chloride solution was stirred at 600 rpm with a cylindrical stirrer having a length of 40 mm and a thickness of 8 mm. The water absorption time (second) was measured. The end point was in conformity with a standard described in JIS K 7224-1996 fiscal year "Testing method for water absorbent speed of water-absorbing resins." A period of time until the water-absorbing agent absorbs the physiological saline solution and the test liquid covers a stirrer chip was measured as the water absorption time (second).

(d) Particle Size Distribution, Weight Average Particle Diameter (D50), and Logarithmic Standard Deviation (a) of Water-Absorbing Agent (Water-Absorbing Resin Powder)

The particle size (PSD) and the logarithmic standard deviation (αζ) in the particle size distribution of the particulate water-absorbing agent (water-absorbing resin powder) according to the present invention were measured in conformity with the measurement method disclosed in US 2006/204755 A.

That is, 10.00 g of the sample was classified using a JIS standard sieve (The IIDA TESTING SIEVE: internal diameter of 80 mm; JIS Z8801-1 (2000)) having a mesh size of 850 Mm, 600 μm, 500 μm, 425 μm, 300 μm, 150 μm, or 45 μm or a sieve corresponding to the JIS standard sieve. After the classification, the weight of each sieve was measured, and the weight percent (wt %) of particles having a particle diameter of less than 150 μm was calculated. Incidentally, the term "weight percent of particles having a particle diameter of less than 150 μm" refers to the weight ratio (%)

of particles passing through a JIS standard sieve having a mesh size of 150 μm with respect to the whole sample.

Further, regarding the weight average particle diameter (D50), the residual percentage R of each particle size was plotted on a logarithmic probability paper and the particle diameter corresponding to R=50 wt % was read as the weight average particle diameter (D50) from this graph. The weight average particle diameter (D50) means a particle diameter corresponding to 50 wt % of the whole particulate water-absorbing agent (sample). Further, the logarithmic standard deviation (σζ) in the particle size distribution is represented by the following (Formula 4). A smaller σζ value means a narrower particle size distribution.

[Mathematical Formula 6]

$$\sigma\zeta=0.5\times\ln(X2/X1) \quad \text{(Formula 4)}$$

(X1 represents the particle diameter at R=84.1%, X2 represents the particle diameter at R=15.9%, and ln represents logarithm natural.)

(e) Surface Tension 50 ml of a 0.90 wt % aqueous sodium chloride solution, a temperature of which was adjusted to 20° C., was put into a 100 ml beaker sufficiently washed. First, the surface tension of the 0.90 wt % aqueous sodium chloride solution was measured using a surface tension meter (K11 automatic surface tension meter manufactured by KRUSS GmbH). In this measurement, the surface tension has to be in a range of 71 mN/m to 75 mN/m. Subsequently, a sufficiently washed cylindrical stirrer having a length of 25 mm and −0.500 g of the particulate water-absorbing agent were put into a beaker containing 50 ml of the 0.90 wt % aqueous sodium chloride solution after the measurement of the surface tension, the temperature of which was adjusted to 20° C. The resulting mixture was stirred at 350 rpm for 3 minutes. After 3 minutes, stirring was stopped. After the water-containing particulate water-absorbing agent, which has been left to stand still for 2 minutes, was precipitated, a similar operation was performed again, and the surface tension of the supernatant was measured. Herein, when the supernatant does not remain in required volume for measurement after the particulate water-absorbing agent is precipitated because the water absorption speed thereof is high or the absorption capacity thereof is high, measurement was conducted by appropriately adjusting the amount of 50 ml of the 0.90 wt % aqueous sodium chloride solution to be in the minimum range necessary for measurement. Incidentally, the present invention employs a plate method using a platinum plate. The plate was sufficiently washed with deionized water and was heated and washed with a gas burner before each measurement, and used.

(f) Solids Content and Moisture Content

About 1 g (weight W9 (g)) of a water-absorbing resin (water-absorbing agent) (particulate hydrogel) was measured and put into an aluminum cup (weight W8 (g)) having a diameter of the bottom surface of about 5 cm, and was left for 3 hours in a dryer without wind at 180° C. and then dried. The total weight (W10 (g)) of the aluminum cup and the water-absorbing resin (water-absorbing agent) after drying was measured, and the solids content was determined by the following (Formula 5). Further, the moisture content was determined by the following (Formula 6).

[Mathematical Formula 7]

$$\text{solids content (wt \%)}=\{(W10-W8)/W9\}\times100 \quad \text{(Formula 5)}$$

[Mathematical Formula 8]

$$\text{moisture content (wt \%)}=100-\text{solids content (wt \%)} \quad \text{(Formula 6)}$$

(g) GCA (Gel Capillary Absorption)

An apparatus and a method for measuring GCA is described with reference to FIG. 1. A glass filter 2 used in this measurement method is a 500 ml glass filtration apparatus as specified by ISO 4793 (1980), has a pore diameter of P40 (16 μm to 40 μm) and a thickness of 7 mm, and is, for example, a Duran grade 3 glass filtration apparatus manufactured by Schott Inc. Further, the filter having a radius of 30 cm has to have a water flowing ability of 50 ml/min at 20° C. at a pressure difference of 50 mbar. A silicone tube 3 is connected to the lower part of the filtration apparatus 1 with the glass filter, and is further connected to the lower part of a tank 6 provided with a glass tube 5 and a stop cock 4. At this time, the upper surface of the glass filter is fixed at a position 10 cm higher than the meniscus of the lower part of the glass tube in the tank. The system is filled with 0.90 wt % of aqueous sodium chloride solution. A high humidity strength cellulose tissue 8 cut into an 8 cm square is fixed to the bottom of a plastic support cylinder 7 having an inner diameter of 60 mm with a metal ring. The tissue has a maximum basis weight of 24.6 g/m$^2$ and a minimum humidity tensile strength of 0.32 N/cm (CD direction) and 0.8 N/cm (MD direction) (the flowing direction when paper is produced by a paper machine is referred to as the MD direction, and a direction perpendicular thereto is referred to as the CD direction), and is available from Fripa Inc. in Germany, for example. 100.2 g (weight W11 (g)) of the particulate water-absorbing agent was scattered uniformly on the tissue under the conditions of a room temperature (20° C. to 25° C.) and a humidity of 50 RH %. A piston 9 adjusted so as to uniformly apply a load of 0.39 kPa (0.05 psi) to the water-absorbing agent, having an outer diameter of slightly less than 60 mm, not causing a gap with the support cylinder, and capable of moving vertically without being hindered, was put on the particulate water-absorbing agent. The weight of the whole measurement apparatus (W12 [g]) was measured. The whole measurement apparatus was put on a glass filter. A valve of the fluid tank with a Mariotte tube was opened for absorption for 10 minutes. Thereafter, the whole measurement apparatus was pulled up, and the weight thereof (W13 (g)) was measured. GCA (g/g) was calculated according to the following (Formula 7) from W11, W12, and W13.

[Mathematical Formula 9]

$$\text{GCA (g/g)}=(W13-W12)/W11 \quad \text{(Formula 7)}$$

(h) FGBP

FGBP of the present invention was carried out in conformity with a gel bed permeability test under the "free swelling" condition described in WO 2004/096304 A, except that the water-absorbing agent in a range of 300 μm to 600 μm was not selected, the particle diameter of the water-absorbing agent was measured as it was, and a period of time for collecting data was changed from every 1 second for 20 seconds to every 5 seconds for 180 seconds.

(i) Particle Size Distribution and Weight Average Particle Diameter (D50) of Crosslinked Hydrogel Polymer (Hydrogel Particles)

20 g of the crosslinked hydrogel polymer (hydrogel particles) (solids content: a wt %) at a temperature of 20° C. to 25° C. was added to 1,000 g of a 20 wt % aqueous sodium chloride solution containing 0.08 wt % of EMAL 20C (surfactant, manufactured by Kao Corporation) (hereinafter, referred to as the "EMAL aqueous solution") to obtain a dispersion and the dispersion was stirred with a stirrer chip (length 50 mm×diameter 7 mm) at 300 rpm for 16 hours (using a columnar polypropylene vessel, height: 21 cm, diameter: 8 cm, having a capacity of about 1.14 L).

After finishing the stirring, the dispersion was supplied to a central portion of JIS standard sieves (diameter: 21 Cm, mesh sizes of the sieves; 8 mm/4 mm/2 mm/1 mm/0.60 mm/0.30 mm/0.15 mm/0.075 mm) disposed on a turntable. All the crosslinked hydrogel polymer (hydrogel particles) was washed with use of 100 g of the EMAL aqueous solution so that the crosslinked hydrogel polymer (hydrogel particles) would appear on the sieves, and then 6,000 g of the EMAL aqueous solution was uniformly poured from above at the height of 30 cm with use of a shower (with 72 holes, flow rate; 6.0 L/min) while the sieves were manually rotated (at 20 rpm) so that the water-pouring range (50 cm$^2$) would cover the entire sieves. This operation was repeated four times to classify the crosslinked hydrogel polymer (hydrogel particles). The classified crosslinked hydrogel polymer (hydrogel particles) on a first-stage sieve was drained for about 2 minutes and then weighed. The classified crosslinked hydrogel polymer (hydrogel particles) on second and subsequent sieves were classified by the similar operation and drained, and the crosslinked hydrogel polymer (hydrogel particles) remaining on each sieve was weighed. Incidentally, in a case where the hydrogel particle diameter becomes small, the mesh sizes of the sieves are 0.15 mm and 0.0-75 mm, and clogging occurs, measurement was carried out by replacing sieves with JIS standard sieves having a larger diameter (diameter: 30 cm, mesh sizes of the sieves; 0.15 mm/0.075 mm).

The wt % ratio with respect to the whole crosslinked hydrogel polymer (hydrogel particles) was calculated from the weight of the crosslinked hydrogel polymer (hydrogel particles) remaining on each sieve by the following formula (8). The mesh sizes of the sieves after draining were converted according to the following formula (9) and the particle size distribution of the crosslinked hydrogel polymer (hydrogel particles) was plotted on a logarithmic probability paper. From this graph, the particle diameter in which the residual percentage corresponds to 50 wt % was read as the weight average particle diameter (D50) of the crosslinked hydrogel polymer (hydrogel particles).

[Mathematical Formula 10]

$$X(\%)=(w/W)*100 \qquad \text{(Equation 8)}$$

[Mathematical Formula 11]

$$R(\alpha)(mm)=(20/W)^{1/3}*r \qquad \text{(Equation 9)}$$

Incidentally, here,

X; wt % (%) of the crosslinked hydrogel polymer (hydrogel particles) remaining on each of the sieves after being classified and drained w; a weight (g) of the crosslinked hydrogel polymer (hydrogel particles) remaining on each of the sieves after being classified and drained W; a total weight (g) of the crosslinked hydrogel polymer (hydrogel particles) remaining on each of the sieves after being classified and drained R($\alpha$); a mesh size (mm) of a sieve in terms of a crosslinked hydrogel polymer whose solids content is $\alpha$ wt % r; a mesh size (mm) of a sieve with which a crosslinked hydrogel polymer (hydrogel particles) having swollen in a 20 wt % aqueous sodium chloride solution is classified (j) Weight Average Particle Diameter Converted to Dried Product of Hydrogel Particles When GelD50 is a weight average particle diameter (μm) of the hydrogel particles, GS is a solids content (wt %) of the hydrogel particles, and SolidD50 is a weight average particle diameter (μm) in terms of the dried product of the hydrogel particles, the weight average particle diameter of the hydrogel particles in terms of the dried product is defined by the following formula.

$$\text{Solid}D50=\text{Gel}D50\times(GS/100)^{1/3} \qquad \text{(formula)}$$

(k) Weight Average Molecular Weight

Measurement was conducted by a size exclusion chromatography (GPC) in terms of polyethylene glycol under the following measurement conditions.

Measurement Conditions

Apparatus: Waters Alliance (2695) manufactured by Waters Corp.

Analysis Software: Empower professional+GPC option, manufactured by Waters Corp.

Used column: TSK guard column SWXL+TSKgel G4000SWXL+G3000SWXL+G2000SWXL, manufactured by Tosoh Corporation Detector: differential refractive index (RI) detector (manufactured by Waters Corp., Waters 2414)

Eluent: prepared by dissolving 115.6 g of sodium acetate tribydrate into a mixture solvent of 10,999 g of water and 6,001 g of acetonitrile and adjusting the pH of the mixture to 6.0 with acetic acid Standard substance for preparing calibration curve: polyethylene glycol [peak top molecular weights (Mp): 300,000, 200,000, 107,000, 50,000, 27,700, 11,840, 6,450, 1,470, and 472]

Calibration curve: Third-order calibration curve prepared based on the Mp values of the above polyethylene glycols and elution times thereof Flow rate: 1.0 mL/min Column temperature: 40° C.

Measurement time: 45 minutes

Amount of sample solution injected: 100 μL (eluent solution with a sample concentration of 0.5 wt %)

(l) BET Specific Surface Area

The BET specific surface area of the water-absorbing resin powder of the present invention was measured by the following method. A high-accuracy gas/vapor adsorption amount measuring apparatus (manufactured by Bell Japan Inc., BELSORP-max) was used in measurement of the BET specific surface area and a pretreatment apparatus for adsorption measurement (manufactured by Bell Japan Inc., BELSORP-vacII) was used in pretreatment.

A Pyrex (registered trademark) glass rod was put into a Pyrex (registered trademark) test tube attached to the BET specific surface area measurement apparatus, and reduced-pressure degassing was performed using a pretreatment apparatus for adsorption measurement. After a pressure reached a predetermined apparatus pressure, water-absorbing resin powder was put into the Pyrex (registered trademark) test tube by visual inspection so as to fill about 80% of the test chamber below using a Pyrex (registered trademark) sampling funnel for BELSORP-max attached to the measurement apparatus. At the time, the weight of the water-absorbing resin powder was recorded. Thereafter, the test tube was subjected to reduced-pressure degassing using the pretreatment apparatus for adsorption measurement. After a pressure reached a predetermined apparatus pressure, measurement was carried out by high-accuracy gas/vapor adsorption amount measuring apparatus at a liquid nitrogen temperature using krypton gas as an adsorbate. The BET specific surface area was obtained from the obtained adsorption isotherm by the BET theory with use of analysis software.

Example 1

(Preparation and Polymerization Steps of (Meth)Acrylic Acid (Salt)-Based Aqueous Monomer Solution)

Into a reaction vessel constituted of a lid equipped with a thermometer, a nitrogen gas introduction pipe and a discharge hole and a tray (bottom surface: 3.00 mm×220 mm, depth: 60 mm), 170 g of acrylic acid, 1,800 g of a 37 wt % aqueous sodium acrylate solution, 0.99 g of polyethylene glycol diacrylate (weight average molecular weight: 523), 6.688 g (0.8 wt % with respect to the monomer component) of polyethylene glycol (weight average molecular weight: 2,000, manufactured by Wako Pure Chemical Industries, Ltd.) and 216 g of deionized water were supplied and mixed, and the reaction vessel was immersed up to a height of 10 mm from the bottom of the tray in a water bath set at 20° C.

Nitrogen gas was introduced into this aqueous solution and degassed for 20 minutes. After confirming that this solution became 20° C., 6.61 g of a 20 wt % aqueous sodium persulfate solution and 6.33 g of a 0.1 wt % aqueous L-ascorbic acid solution were added thereto under a nitrogen flow atmosphere and mixed under stirring. The monomer concentration was 38 wt %. After 1 minute, polymerization was initiated, and the temperature of the reaction system at this time was 20° C. After initiation of polymerization, the polymerization system was, not stirred, and subsequently the reaction vessel was immersed in the water bath set at 20° C. so as to be cooled. After 17 minutes, the polymerization system showed the maximum reaching temperature of 89° C. Thereafter, the temperature of the water bath was adjusted to 70° C. and then the polymerization reaction was performed for 20 minutes to thereby obtain a crosslinked hydrogel polymer (GK1).

(Gel-Crushing Step)

The obtained crosslinked hydrogel polymer (GK1) was cut into blocks, put into UNIPACK (manufactured by SEISANNIPPONSHA LTD.), and left to stand still in a thermostat for 1 hour at a constant temperature of 60° C. The crosslinked hydrogel polymer (GK1), the temperature of which was maintained at a constant temperature of 60° C., was allowed to pass twice through a meat chopper (manufactured by REMACOM, model: HL-G22SN) having a die plate with a aperture diameter of 3.5 mm and warmed to 60° C. by using a sheet heater, thereby obtaining hydrogel particles (also referred to as "crosslinked hydrogel polymer crushed product") (GKF1).

The rotation speed of the screw axis of the meat chopper was set to 210 rpm, the crosslinked hydrogel polymer (GK1) was supplied at 360 g/min, and then the obtained gel-crushed product was also supplied similarly at 360 g/min and was allowed to pass twice through the meat chopper.

The physical properties of the crosslinked hydrogel polymer crushed product (GKF1) are presented in the following table. The following crosslinked hydrogel polymer crushed product (GKF) is presented similarly in the following table.

(Steps for Drying, Pulverizing and Classifying)

The obtained crosslinked hydrogel polymer crushed product (GKF1) was dried at 160° C. for 45 minutes by a hot air drier to obtain a dried product. Thereafter, the dried product was crushed by a roll mill (manufactured by Inokuchi Giken Limited Company), and was sifted with sieves having mesh sizes of 850 μm, 600 μm, 500 μm, 300 μm, and 150 μm. Then, blending was carried out such that particles passing through a sieve having a mesh size of 850 μm and not passing through a sieve having a mesh size of 600 μm were 3 wt %, particles passing through a sieve having a mesh size of 600 μm and not passing through a sieve having a mesh size of 500 μm were 10 wt %, particles passing through a sieve having a mesh size of 500 μm and not passing through a sieve having a mesh size of 300 μm were 54 wt %, particles passing through a sieve having a mesh size of 300 μm and not passing through a sieve having a mesh size of 150 μm were 31 wt %, and particles passing through a sieve having a mesh size of 150 μm and not passing through a sieve having a mesh size of 45 μm were 2 wt %. Thereby, water-absorbing resin powder (B1) was obtained. Incidentally, the blending was similarly performed except Example 15.

The weight average particle diameter D50, the logarithmic standard deviation, and CRC of the water-absorbing resin powder (B1) are presented in the following table. The water-absorbing resin powder (B) described below is presented similarly in the following table.

(Surface Crosslinking Step)

A surface crosslinking agent solution containing 0.025 parts by weight of ethylene glycol diglycidyl ether, 0.3 parts by weight of ethylene carbonate, 0.5 parts by weight of propylene glycol, and 2.0 parts by weight of deionized water was mixed with 100 parts by weight of the water-absorbing resin powder (B1) by spraying. The above-described mixture was subjected to the heat treatment at 200° C. for 35 minutes to obtain surface crosslinked water-absorbing resin particles (S1).

(Step for Adding Liquid Permeability Enhancer)

1 part by weight of a 1 wt % aqueous pentasodium diethylenetriamine pentaacetate (DTPA) solution with respect to 100 parts by weight of the surface crosslinked water-absorbing resin particles (S1) was added as a chelating agent under stirring and mixed for 1 minute. When the chelating agent is contained, urine resistance is improved.

Subsequently, the resultant mixture was left to stand in a hot air drier set at 60° C. for 30 minutes and was then allowed to pass through a wire mesh having a mesh size of 850 μm, and then 0.6 parts by weight of fumed silica (Aerosil 200, manufactured by NIPPON AEROSIL Co., Ltd.) was mixed therewith. For mixing, 30 g of the surface crosslinked water-absorbing resin particles (S1) was put with fumed silica into a mayonnaise jar having a volume of 225 ml and shaken for 3 minutes by using a paint shaker to obtain a particulate water-absorbing agent (EX-1). The performance of the obtained particulate water-absorbing agent (EX-1) is described below. The same applies hereafter.

Example 2

Water-absorbing resin powder (B2), surface-treated water-absorbing resin particles (S2), and a particulate water-absorbing agent (EX-2) were obtained by performing the operation similar to that of Example 1, except that the amount of polyethylene glycol used was changed to 3.344 g (0.4 wt % with respect to the monomer component).

Example 3

Water-absorbing resin powder (B3), surface-treated water-absorbing resin particles (S3), and a particulate water-absorbing agent (EX-3) were obtained by performing the operation similar to that of Example 1, except that the amount of polyethylene glycol used was changed to 10.03 g (1.2 wt % with respect to the monomer component).

Example 4

Water-absorbing resin powder (B4), surface-treated water-absorbing resin particles (S4), and a particulate water-absorbing agent (EX-4) were obtained by performing the operation similar to that of Example 1, except that the weight average molecular weight of polyethylene glycol used was changed to 400.

Example 5

Water-absorbing resin powder (B5S), surface-treated water-absorbing resin particles (S5), a particulate water-absorbing agent (EX-5) were obtained by performing the operation similar to that of Example 1, except that the weight average molecular weight of polyethylene glycol used was changed to 20,000.

Example 6

(Preparation and Polymerization Steps of (Meth)Acrylic Acid (Salt)-Based Aqueous Monomer Solution)

Into a reaction vessel constituted of a lid equipped with a thermometer, a nitrogen gas introduction pipe and a discharge hole, and a tray (bottom surface: 300 mm×220 mm, depth: 60 mm), 170 g of acrylic acid, 1,800 g of 37 wt % aqueous sodium acrylate solution, 0.99 g of polyethylene glycol diacrylate (average molecular weight: 523), and 216 g of deionized water were supplied and mixed, and the reaction vessel was immersed up to a height of 10 mm from the bottom of the tray in a water bath set at 20° C. Nitrogen gas was introduced into this aqueous solution and degassed for 20 minutes. After confirming that this solution became 20° C., 6.61 g of a 20 wt % aqueous sodium persulfate solution and 6.33 g of a 0.1 wt % aqueous L-ascorbic acid solution were added thereto under a nitrogen flow atmosphere and mixed under stirring. The monomer concentration was 38 wt %. After 1 minute, polymerization was initiated, and the temperature of the reaction system at this time was 20° C. After initiation of polymerization, the polymerization system was not stirred, and subsequently the reaction vessel was immersed in the water bath set at 20° C. so as to be cooled. After 17 minutes, the polymerization system showed the maximum reaching temperature of 89° C. Thereafter, the temperature of the water bath was adjusted to 70° C. and then the polymerization reaction was performed for 20 minutes to thereby obtain a crosslinked hydrogel polymer (GK6). The obtained crosslinked hydrogel polymer (GK6) was cut into blocks.

The obtained crosslinked hydrogel polymer (GK6) was cut into blocks, put into UNIPACK (manufactured by SEI-SANNIPPONSHA LTD.), and left to stand still in a thermostat for 1 hour at a constant temperature of 60° C. In the crosslinked hydrogel polymer (GK6), the temperature of which was maintained at a constant temperature of 60° C., 66.9 g of a methanol solution containing 10 wt % of polyethylene glycol (weight average molecular weight: 2,000, manufactured by Wako Pure Chemical Industries, Ltd.) was sprinkled uniformly on the surface of 2,200 g of the block-shaped crosslinked hydrogel polymer (GK6), and was allowed to pass twice through a meat chopper (manufactured by REMACOM, model: HL-G22SN) having a die plate with a aperture diameter of 3.5 mm and warmed to 60° C. by using a sheet heater, thereby obtaining a crosslinked hydrogel polymer crushed product (GKF6).

The rotation speed of the screw axis of the meat chopper was set to 210 rpm, the crosslinked hydrogel polymer (GK6) was supplied at 360 g/min, and then the obtained gel-crushed product was also supplied similarly at 360 g/min and was allowed to pass twice through the meat chopper.

(Steps for Drying, Pulverizing and Classifying)

The obtained crosslinked hydrogel polymer crushed product (GKF6) was dried at 160° C. for 45 minutes by a hot air drier to obtain a dried product. Thereafter, the dried product was crushed by a roll mill (manufactured by Inokuchi Giken Limited Company), and was sifted with sieves having mesh sizes of 850 μm, 600 μm, 500 μm, 300 μm, and 150 μm. Then, blending was carried out to obtain water-absorbing resin powder (B6). The performance of the obtained water-absorbing resin powder (B6) is presented in Table 1.

(Surface Crosslinking Step)

A surface crosslinking agent solution containing 0.025 parts by weight of ethylene glycol diglycidyl ether, 0.3 parts by weight of ethylene carbonate, 0.5 parts by weight of propylene glycol, and 2.0 parts by weight of deionized water was mixed with 100 parts by weight of the water-absorbing resin powder (B6). The above-described mixture was subjected to the heat treatment at 200° C. for 35 minutes to obtain surface crosslinked water-absorbing resin particles (S6).

(Step for Adding Liquid Permeability Enhancer)

1 part by weight of a 1 wt % aqueous DTPA solution with respect to 100 parts by weight of the surface crosslinked water-absorbing resin particles (S6) was added under stirring and mixed for 1 minute. Subsequently, the resultant mixture was left to stand in a hot air drier set at 60° C. for 30 minutes and was then allowed to pass through a wire mesh having a mesh size of 850 μm, and then 0.6 parts by weight of hydrotalcite (DHT-6, manufactured by Kyowa Chemical Industry Co., Ltd.) was mixed therewith. For mixing, 30 g of the surface crosslinked water-absorbing resin particles (S6) was put with hydrotalcite into a mayonnaise jar having a volume of 225 ml and shaken for 3 minutes by using a paint shaker to obtain a particulate water-absorbing agent (EX-6). The performance of the obtained particulate water-absorbing agent (EX-6) is presented in the following table.

Example 7

1 part by weight of a 1 wt % aqueous DTPA solution with respect to 100 parts by weight of the surface crosslinked water-absorbing resin particles (S1) in Example 1 was added under stirring and mixed for 1 minute. Further, a solution containing 1.17 parts by weight of a 27.5 wt % aqueous aluminum sulfate solution (8 wt % in terms of aluminum oxide), 0.196 parts by weight of a 60 wt % aqueous sodium lactate solution, and 0.029 parts by weight of propylene glycol was added thereto and mixed for 1 minute. Thereafter, the resultant mixture was left to stand in a hot air drier for 30 minutes and was then allowed to pass through a wire mesh having a mesh size of 850 μm to obtain a particulate water-absorbing agent (EX-7). The performance of the obtained particulate water-absorbing agent (EX-7) is presented in the following table.

Example 8

(Preparation and Polymerization Steps of (Meth)Acrylic Acid (Salt)-Based Aqueous Monomer Solution)

A crosslinked hydrogel polymer (GK8) was obtained by performing the operation similar to that of Example 1, except that the amount of polyethylene glycol diacrylate was changed to 1.73 g.

(Gel-Crushing Step)

The obtained crosslinked hydrogel polymer (GK8) was cut into blocks, put into UNIPACK (manufactured by SEI-SANNIPPONSHA LTD.), and left to stand still in a thermostat for 1 hour to at a constant temperature of 60° C. The crosslinked hydrogel polymer (GK8), the temperature of which was maintained at a constant temperature of 60° C., was supplied to a screw extruder, which has been warmed to 60° C. by using a sheet heater, and then gel-crushed. As the screw extruder, a meat chopper, which is provided with a porous plate (diameter: 100 mm, pore diameter: 3.2 mm, the number of pores: 316, opening ratio: 32.3%, thickness: 10 mm) at the tip end and in which the screw axis has an outer diameter of 86 mm and the internal diameter of the casing is B8 mm, was used.

The rotation speed of the screw axis of the meat chopper was set to 126 rpm, and the crosslinked hydrogel polymer (GK8) was supplied at 1,680 g/min and allowed to pass once, thereby obtaining a crosslinked hydrogel polymer crushed product (GKF8).

At this time, the gel grinding energy GGE (1) was 174.8 J/g and the gel grinding energy GGE (2) was 40.4 J/g.

(Steps for Drying, Pulverizing and Classifying)

Water-absorbing resin powder (B8) was obtained by performing the operation similar to that of Example 1, except that the obtained crosslinked hydrogel polymer crushed product (GKF8) was dried at 185° C. for 30 minutes by a hot air drier.

(Surface Crosslinking Step) and (Step for Adding Liquid Permeability Enhancer)

The obtained water-absorbing resin powder (B8) was subjected to the operation similar to that of Example 1 to obtain surface crosslinked water-absorbing resin particles (S8) and a particulate water-absorbing agent (EX-8). The performance of the obtained particulate water-absorbing agent (EX-8) is presented in the following table.

Example 91

(Preparation and Polymerization Steps of (Meth)Acrylic Acid (Salt)-Based Aqueous Monomer Solution)

A crosslinked hydrogel polymer (GK9) was obtained by performing the operation similar to that of Example 1, except that the amount of polyethylene glycol diacrylate was changed to 1.73 g and polyethylene glycol was not used.

(Gel-Crushing Step)

A crosslinked hydrogel polymer crushed product (GKF9) was obtained by performing the operation similar to that of Example 8, except that 6.688 g (0.8 wt % with respect to the monomer concentration) of polyethylene glycol (weight average molecular weight: 2,000, manufactured by Wako Pure Chemical Industries, Ltd.) was supplied at 20.5 g/min as a 20 wt % aqueous solution and the obtained crosslinked hydrogel polymer (GK9) was supplied at 1680 g/min.

At this time, the gel grinding energy GGE (1) was 175.7 J/g and the gel grinding energy GGE (2) was 41.3 J/g.

(Steps for Drying, Pulverizing and Classifying)

Water-absorbing resin powder (B9) was obtained by performing the operation similar to that of Example 1, except that the obtained crosslinked hydrogel polymer crushed product (GKF9) was dried at 185° C. for 30 minutes by a hot air drier.

(Surface Crosslinking Step) and (Step for Adding Liquid Permeability Enhancer)

The obtained water-absorbing resin powder (B9) was subjected to the operation similar to that of Example 1 to obtain surface crosslinked water-absorbing resin particles (S9) and a particulate water-absorbing agent (EX-9). The performance of the obtained particulate water-absorbing agent (EX-9) is presented in the following table.

In Example 9 described above, the adhesion controlling agent is not added during polymerization but the adhesion controlling agent is added while the meat chopper is operated (during gel-crushing).

Example 10

(Preparation and Polymerization Steps of (Meth)Acrylic Acid (Salt)-Based Aqueous Monomer Solution)

A crosslinked hydrogel polymer (GK10) was obtained by performing the operation similar to that of Example 1, except that the amount of polyethylene glycol diacrylate was changed to 1.73 g.

(Gel-Crushing Step)

The obtained crosslinked hydrogel polymer (GK10) was subjected to the operation similar to that of Example 8 to obtain a crosslinked hydrogel polymer crushed product (GKF11).

At this time, the gel grinding energy GGE (1) was 174.8 J/g and the gel grinding energy GGE (2) was 40.4 J/g.

(Steps for Drying, Pulverizing and Classifying)

Water-absorbing resin powder (B10) was obtained by performing the operation similar to that of Example 1, except that the obtained crosslinked hydrogel polymer crushed product (GKF10) was dried at 185° C. for 30 minutes by a hot air drier.

(Surface Cross-Linking Step)

Surface-treated water-absorbing resin particles (S10) were obtained by performing the operation similar to that of Example 1, except that the heat treatment time of the water-absorbing resin powder (B10) was set to 45 minutes.

(Step for Adding Liquid Permeability Enhancer)

The surface-treated water-absorbing resin particles (S10) were subjected to the operation similar to that of Example 1 to obtain a particulate water-absorbing agent (EX-10). The performance of the obtained particulate water-absorbing agent (EX-10) is presented in the following table.

In Example 11, the thermal treatment time of the surface crosslinking step was set to be relatively longer. According to this, the effect of improving FGBP is achieved.

Example 11

(Preparation and Polymerization Steps of (Meth)Acrylic Acid (Salt)-Based Aqueous Monomer Solution)

A monomer solution containing 380 g of acrylic acid, 158 g of a 48 wt % aqueous sodium hydroxide solution, 1.53 g of polyethylene glycol diacrylate (weight average molecular weight: 523), 3.74 g (0.8 wt % with respect to the monomer component) of polyethylene glycol (weight average molecular weight: 2,000, manufactured by Wako Pure Chemical Industries, Ltd.), 23.4 g of a 0.1 wt % aqueous trisodium diethylene triamine pentaacetate solution and 333 g of deionized water was prepared. Then, 162 g of a 48 wt % aqueous sodium hydroxide solution was added to the monomer solution adjusted to 45° C. with stirred. The temperature of the mixture was increased to 80° C. by neutralization heat at this time. Further, 18.58 g of a 4 wt % aqueous sodium persulfate solution was added and the mixture was flowed on Teflon (registered trademark) sheet (a reaction vessel having a size of 30 cm×30 cm whose four sides are surrounded by weirs having a height of 1.5 cm) whose the bottom surface has been already warmed to 50° C., in an ambient temperature of 60° C. so as to perform polymerization. After 1 minute from the addition of the aqueous sodium persulfate solution, the polymerization system showed the maximum reaching temperature of 105° C. After further 4 minutes, the obtained polymer was taken out to obtain a crosslinked hydrogel polymer (GK11).

(Gel-Crushing Step)

A crosslinked hydrogel polymer crushed product (GKF11) was obtained by performing the operation similar to that of Example 8, except that the rotation speed of the screw axis was set to 130 rpm and the crosslinked hydrogel polymer (GK11) was supplied at 4,640 g/min to the meat chopper.

At this time, the gel grinding energy GGE(1) was 69.4 J/g and the gel grinding energy GGE (2) was 24.0 J/g.

(Steps for Drying, Pulverizing and Classifying)

Water-absorbing resin powder (B11) was obtained by performing the operation similar to that of Example 1, except that the obtained crosslinked hydrogel polymer crushed product (GKF11) was dried at 190° C. for 30 minutes by a hot air drier.

(Surface Crosslinking Step)

Surface-treated water-absorbing resin particles (S11) were obtained by performing the operation similar to that of Example 1, except that the heat temperature treatment time of the water-absorbing resin powder (B11) was set to 25 minutes.

(Step for Adding Liquid Permeability Enhancer)

The surface-treated water-absorbing resin particles (S11) were subjected to the operation similar to that of Example 1 to obtain a particulate water-absorbing agent (EX-11). The performance of the obtained particulate water-absorbing agent (EX-11) is presented in the following table.

Example 12

(Preparation and Polymerization Steps of (Meth)Acrylic Acid (Salt)-Based Aqueous Monomer Solution)

A crosslinked hydrogel polymer (GK12) was obtained by performing the operation similar to that of Example 11, except that the amount of polyethylene glycol diacrylate was changed to 1.39 g and 1.17 g (0.075 wt % as an effective ingredient with respect to the monomer component) of AMPHITOL 20BS (Kao Corporation, effective ingredient: 30 wt %) was used instead of polyethylene glycol (weight average molecular weight: 2,000, manufactured by Wako Pure Chemical Industries, Ltd.).

(Gel-Crushing Step)

As the screw extruder, a meat chopper, which is provided with a porous plate (diameter: 100 mm, pore diameter: 6.4 mm, the number of pores: 83, opening ratio: 34.0%, thickness: 10 mm) at the tip end and in which the screw axis has an outer diameter of 86 mm and of which the internal diameter of the casing is 88 mm, was used. A crosslinked hydrogel polymer crushed product (GKF12) was obtained by performing the operation similar to that of Example 8, except that the meat chopper was used and the crosslinked hydrogel polymer (GK12) was supplied at 4,640 g/min and the rotation speed of the screw axis of 130 rpm to the meat chopper.

At this time, the gel grinding energy GGE (1) was 57.5 J/g and the gel grinding energy GGE (2) was 13.3 J/g.

(Steps for Drying, Pulverizing and Classifying)

Water-absorbing resin powder (B12) was obtained by performing the operation similar to that of Example 1, except that the obtained crosslinked hydrogel polymer crushed product (GKF12) was dried at 190° C. for 30 minutes by a hot air drier.

(Surface Crosslinking Step)

Surface-treated water-absorbing resin particles (S12) were obtained by performing the operation similar to that of Example 1, except that the heat temperature treatment time of the water-absorbing resin powder (B12) was set to 30 minutes.

(Step for Adding Liquid Permeability Enhancer)

The surface-treated water-absorbing resin particles (S12) were subjected to the operation similar to that of Example 1 to obtain a particulate water-absorbing agent (EX-12). The performance of the obtained particulate water-absorbing agent (EX-12) is presented in the following table.

In Example 12, the particle diameter of the crosslinked hydrogel polymer crushed product (GKF12) is increased by lowering GGE.

Example 13

(Preparation and Polymerization Steps of (Meth) Acrylic Acid (Salt)-Based Aqueous Monomer Solution)

A crosslinked hydrogel polymer (GK13) was obtained by performing the operation similar to that of Example 11, except that 1.17 g (0.075 wt % as an effective ingredient with respect to the monomer component) of AMPHITOL 20BS (manufactured by Kao Corporation, effective ingredient: 30 wt %) was used instead of polyethylene glycol (weight average molecular weight: 2,000, manufactured by Wako Pure Chemical Industries, Ltd.).

(Gel-Crushing Step)

A crosslinked hydrogel polymer crushed product (GKF13) was obtained by performing the operation similar to that of Example 8, except that the rotation speed of the screw axis was set to 130 rpm and the crosslinked hydrogel polymer (GK13) was supplied at 4,640 g/min to the meat chopper.

At this time, the gel grinding energy GGE (1) was 65.5 J/g and the gel grinding energy GGE (2) was 24.4 J/g.

(Steps for Drying, Pulverizing and Classifying)

Water-absorbing resin powder (B13) was obtained by performing the operation similar to that of Example 1, except that the obtained crosslinked hydrogel polymer crushed product (GKF13) was dried at 190° C. for 30 minutes by a hot air drier.

(Surface Crosslinking Step)

Surface-treated water-absorbing resin particles (S13) were obtained by performing the operation similar to that of Example 1, except that the heat temperature treatment time of the water-absorbing resin powder (B13) was set to 25 minutes.

(Step for Adding Liquid Permeability Enhancer)

The surface-treated water-absorbing resin particles (S13) were subjected to the operation similar to that of Example 1 to obtain a particulate water-absorbing agent (EX-13). The performance of the obtained particulate water-absorbing agent (EX-13) is presented in the following table.

This Example has excellent results as compared to other Examples. The reason for this is assumed that the polymerization method is short-term polymerization using neutralization heat, the molecular weight of the main chain is large, the molecular weight distribution is also narrow, the physical properties are improved, and the adhesion controlling agent is particularly suitable.

Example 14

(Preparation and Polymerization Steps of (Meth)Acrylic Acid (Salt)-Based Aqueous Monomer Solution)

A crosslinked hydrogel polymer (GK14) was obtained by performing the operation similar to that of Example 1, except that the amount of polyethylene glycol diacrylate was changed to 1.73 g and 2.090 g (0.075 wt % as an effective ingredient with respect to the monomer component) of AMPHITOL 20BS (manufactured by Kao Corporation, effective ingredient: 30 wt %) was used instead of polyethylene glycol (weight average molecular weight: 2,000, manufactured by Wako Pure Chemical Industries, Ltd.).

(Gel-Crushing Step)

A crosslinked hydrogel polymer crushed product (GKF14) was obtained by performing the operation similar to that of Example B, except that the number of revolutions of the screw axis was set to 225 rpm.

At this time, the gel grinding energy GGE (1) was 182.2 J/g and the gel grinding energy GGE (2) was 58.3 J/g.

(Steps for Drying, Pulverizing and Classifying)

Water-absorbing resin powder (B14) was obtained by performing the operation similar to that of Example 1, except that the obtained crosslinked hydrogel polymer crushed product (GKF14) was dried at 185° C. for 30 minutes by a hot air drier and blending was carried out such that particles passing through a sieve having a mesh size of 850 μm and not passing through a sieve having a mesh size of 600 μm were 12 wt %, particles passing through a sieve having a mesh size of 600 μm and not passing through a sieve having a mesh size of 500 μm were 25 wt %, particles passing through a sieve having a mesh size of 500 μm and not passing through a sieve having a mesh size of 300 μm were 41 wt %, particles passing through a sieve having a mesh size of 300 μm and not passing through a sieve having a mesh size of 150 μm were 21 wt %, and particles passing through a sieve having a mesh size of 150 μm and not passing through a sieve having a mesh size of 45 μm were 1 wt %.

(Surface Crosslinking Step)

Surface-treated water-absorbing resin particles (S14) were obtained by performing the operation similar to that of Example 1, except that the heat temperature treatment time of the water-absorbing resin powder (B14) was set to 25 minutes.

(Step for Adding Liquid Permeability Enhancer)

The surface-treated water-absorbing resin particles (S14) were subjected to the operation similar to that of Example 1 to obtain a particulate water-absorbing agent (EX-14). The performance of the obtained particulate water-absorbing agent (EX-14) is presented in the following table.

Example 15

(Preparation and Polymerization Steps of (Meth)Acrylic Acid (Salt)-Based Aqueous Monomer Solution)

A crosslinked hydrogel polymer (GK15) was obtained by performing the operation similar to that of Example 1, except that the amount of polyethylene glycol diacrylate was changed to 1.73 g and 2.090 g (0.075 wt % as an effective ingredient with respect to the monomer component) of AMPHITOL 20BS (manufactured by Xao Corporation, effective ingredient: 30 wt %) was used instead of polyethylene glycol (weight average molecular weight: 2,000, manufactured by Wako Pure Chemical Industries, Ltd.).

(Gel-Crushing Step)

A crosslinked hydrogel polymer crushed product (GKF15) was obtained by performing the operation similar to that of Example 8, except that the rotation speed of the screw axis was set to 225 rpm.

(Steps for Drying, Pulverizing and Classifying)

Water-absorbing resin powder (B15) was obtained by performing the operation similar to that of Example 1, except that the obtained crosslinked hydrogel polymer crushed product (GKF15) was dried at 185° C. for 30 minutes by a hot air drier.

(Surface Crosslinking Step)

Surface-treated water-absorbing resin particles (S15) were obtained by performing the operation similar to that of Example 1, except that the heat temperature treatment time of the water-absorbing resin powder (B15) was set to 25 minutes.

(Step for Adding Liquid Permeability Enhancer)

The surface-treated water-absorbing resin particles (S15) were subjected to the operation similar to that of Example 1 to obtain a particulate water-absorbing agent (EX-15). The performance of the obtained particulate water-absorbing agent (EX-15) is presented in the following table.

Example 161

(Preparation and Polymerization Steps of (Meth)Acrylic Acid (Salt)-Based Aqueous Monomer Solution)

A crosslinked hydrogel polymer (GK16) was obtained by performing the operation similar to that of Example 1, except that the amount of polyethylene glycol diacrylate was changed to 1.73 g and polyethylene glycol (weight average molecular weight: 2,000, manufactured by Wako Pure Chemical Industries, Ltd.) was not used.

(Gel-Crushing Step)

The obtained crosslinked hydrogel polymer (GK16) was cut into blocks, put into UNIPACK (manufactured by SEISANNIPPONSHA LTD.), and left to stand still in a thermostat for 1 hour at a constant temperature of 60° C. 62.7 g (0.075 wt % as an effective ingredient with respect to the raw material monomer component amount of the step (i)) of a methanol solution containing 1 wt % of AMPHITOL 20BS (manufactured by Kao Corporation, effective ingredient: 30 wt %) was sprinkled uniformly on the surface of the crosslinked hydrogel polymer (GK16) maintained at a constant temperature of 60° C., and was allowed to pass twice through a meat chopper (manufactured by Iizuka Corporation, model: ROYAL, type: VR-400K) having a die plate with an aperture diameter of 4.7 mm and warmed to 60° C. by using a sheet heater, thereby obtaining a crosslinked hydrogel polymer crushed product (GKF16).

The rotation speed of the screw axis of the meat chopper was set to 170 rpm, a crosslinked hydrogel polymer (GK17) was supplied at 150 g/min, and then the obtained gel-crushed product was also supplied similarly at 150 g/min and was allowed to pass twice through the meat chopper.

(Steps for Drying, Pulverizing and Classifying)

Water-absorbing resin powder (B16) was obtained by performing the operation similar to that of Example 1, except that the obtained crosslinked hydrogel polymer crushed product (GKF16) was dried at 185° C. for 30 minutes by a hot air drier.

(Surface Crosslinking Step)

Surface-treated water-absorbing resin particles (S16) were obtained by performing the operation similar to that of Example 1, except that the heat temperature treatment time of the water-absorbing resin powder (B16) was set to 30 minutes.

(Step for Adding Liquid Permeability Enhancer)

The surface-treated water-absorbing resin particles (S16) were subjected to the operation similar to that of Example 1 to obtain a particulate water-absorbing agent (EX-16). The performance of the obtained particulate water-absorbing agent (EX-16) is presented in the following table.

Example 17

(Preparation and Polymerization Steps of (Meth)Acrylic Acid (Salt)-Based Aqueous Monomer Solution)

A crosslinked hydrogel polymer (GK17) was obtained by performing the operation similar to that of Example 1, except that the amount of polyethylene glycol diacrylate was changed to 1.73 g and polyethylene glycol (weight average molecular weight: 2,000, manufactured by Wako Pure Chemical Industries, Ltd.) was not used.

(Gel-Crushing Step)

A crosslinked hydrogel polymer crushed product (GKF17) was obtained by performing the operation similar to that of Example 16, except that 62.7 g (0.075 wt % as an effective ingredient with respect to the raw material monomer component amount of the step (i)) of a methanol solution containing 1 wt % of AMPHITOL 20HD (manufactured by Kao Corporation, effective ingredient: 30 wt %) was sprinkled uniformly on the surface of the block obtained by cutting the obtained crosslinked hydrogel polymer (GK17).

(Steps for Drying, Pulverizing and Classifying)

Water-absorbing resin powder (B17) was obtained by performing the operation similar to that of Example 1, except that the obtained crosslinked hydrogel polymer crushed product (GKF17) was dried at 185° C. for 30 minutes by a hot air drier.

(Surface Crosslinking Step)

Surface-treated water-absorbing resin particles (S17) were obtained by performing the operation similar to that of Example 1, except that the heat temperature treatment time of the water-absorbing resin powder (B17) was set to 30 minutes.

(Step for Adding Liquid Permeability Enhancer)

The surface-treated water-absorbing resin particles (S17) were subjected to the operation similar to that of Example 1 to obtain a particulate water-absorbing agent (EX-17). The performance of the obtained particulate water-absorbing agent (EX-17) is presented in the following table.

Example 18

(Preparation and Polymerization Steps of (Meth)Acrylic Acid (Salt)-Based Aqueous Monomer Solution)

A crosslinked hydrogel polymer (GK18) was obtained by performing the operation similar to that of Example 1, except that the amount of polyethylene glycol diacrylate was changed to 1.73 g and polyethylene glycol (weight average molecular weight: 2,000, manufactured by Wako Pure Chemical Industries, Ltd.) was not used.

(Gel-Crushing Step)

A crosslinked hydrogel polymer crushed product (GKF18) was obtained by performing the operation similar to that of Example 17, except that 62.7 g (0.075 wt % as an effective ingredient with respect to the raw material monomer component amount of the step (i)) of a methanol solution containing 1 wt % of AMPHITOL 20N (manufactured by Kao Corporation, effective ingredient: 30 wt %) was sprinkled uniformly on the surface of the block obtained by cutting the obtained crosslinked hydrogel polymer (GK18).

(Steps for Drying, Pulverizing and Classifying)

Water-absorbing resin powder (B18) was obtained by performing the operation similar to that of Example 1, except that the obtained crosslinked hydrogel polymer crushed product (GKF18) was dried at 185° C. for 30 minutes by a hot air drier.

(Surface Crosslinking Step)

Surface-treated water-absorbing resin particles (S18) were obtained by performing the operation similar to that of Example 1, except that the heat temperature treatment time of the water-absorbing resin powder (B18) was set to 30 minutes.

(Step for Adding Liquid Permeability Enhancer)

The surface-treated water-absorbing resin particles (S18) were subjected to the operation similar to that of Example 1 to obtain a particulate water-absorbing agent (EX-18). The performance of the obtained particulate water-absorbing agent (EX-18) is presented in the following table.

Example 19

(Preparation and Polymerization steps of (Meth)Acrylic Acid (Salt)-Based Aqueous Monomer Solution)

A crosslinked hydrogel polymer (GK19) was obtained by performing the operation similar to that of Example 1, except that the amount of polyethylene glycol diacrylate was changed to 1.73 g and polyethylene glycol (weight average molecular weight: 2,000, manufactured by Wako Pure Chemical Industries, Ltd.) was not used.

(Gel-Crushing Step)

A crosslinked hydrogel polymer crushed product (GKF19) was obtained by performing the operation similar to that of Example 16, except that 55.7 g (0.050 wt % as an effective ingredient with respect to the raw material monomer component amount of the step (i)) of a methanol solution containing 0.75 wt % of AMIET 105A (manufactured by Kao Corporation, effective ingredient: 100 wt %) was sprinkled uniformly on the surface of the block obtained by cutting the obtained crosslinked hydrogel polymer (GK19).

(Steps for Drying, Pulverizing and Classifying)

Water-absorbing resin powder (B19) was obtained by performing the operation similar to that of Example 1, except that the obtained crosslinked hydrogel polymer crushed product (GKF19) was dried at 185° C. for 30 minutes by a hot air drier.

(Surface Crosslinking Step)

Surface-treated water-absorbing resin particles (S19) were obtained by performing the operation similar to that of Example 1, except that the heat temperature treatment time of the water-absorbing resin powder (B19) was set to 30 minutes.

(Step for Adding Liquid Permeability Enhancer)

The surface-treated water-absorbing resin particles (S19) were subjected to the operation similar to that of Example 1 to obtain a particulate water-absorbing agent (EX-19). The performance of the obtained particulate water-absorbing agent (EX-19) is presented in the following table.

Example 20

(Preparation and Polymerization Steps of (Meth)Acrylic Acid (Salt)-Based Aqueous Monomer Solution)

A crosslinked hydrogel polymer (GK20) was obtained by performing the operation similar to that of Example 1, except that the amount of polyethylene glycol diacrylate was changed to 1.73 g and polyethylene glycol (weight average molecular weight: 2,000, manufactured by Wako Pure Chemical Industries, Ltd.) was not used.

(Gel-Crushing Step)

A crosslinked hydrogel polymer crushed product (GKF20) was obtained by performing the operation similar to that of Example 16, except that 62.7 g (0.075 wt % as an effective ingredient with respect to the raw material monomer component amount of the step (i)) of an isopropyl alcohol solution containing 1 wt % of EMAL 20C (manufactured by Kao Corporation, effective ingredient: 25 wt %) was sprinkled uniformly on the surface of the block obtained by cutting the obtained crosslinked hydrogel polymer (GK20).

(Steps for Drying, Pulverizing and Classifying)

Water-absorbing resin powder (B20) was obtained by performing the operation similar to that of Example 1, except that the obtained crosslinked hydrogel polymer crushed product (GKF20) was dried at 185° C. for 30 minutes by a hot air drier.

(Surface Crosslinking Step)

Surface-treated water-absorbing resin particles (S20) were obtained by performing the operation similar to that of Example 1, except that the heat temperature treatment time of the water-absorbing resin powder (B20) was set to 30 minutes.

(Step for Adding Liquid Permeability Enhancer)

The surface-treated water-absorbing resin particles (S20) were subjected to the operation similar to that of Example 1 to obtain a particulate water-absorbing agent (EX-20). The performance of the obtained particulate water-absorbing agent (EX-20) is presented in the following table.

Example 21

(Preparation and Polymerization Steps of (Meth)Acrylic Acid (Salt)-Based Aqueous Monomer Solution)

A crosslinked hydrogel polymer (GK21) was obtained by performing the operation similar to that of Example 1, except that the amount of polyethylene glycol diacrylate was changed to 1.73 g and polyethylene glycol (weight average molecular weight: 2,000, manufactured by Wako Pure Chemical Industries, Ltd.) was not used.

(Gel-Crushing Step)

A crosslinked hydrogel polymer crushed product (GKF21) was obtained by performing the operation similar to that of Example 16, except that 62.7 g (0.075 wt % as an effective ingredient with respect to the raw material monomer component amount of the step (i)) of a methanol solution containing 1 wt % of ACETAMIN 24 (manufactured by Kao Corporation, effective ingredient: 98 wt %) was sprinkled uniformly on the surface of the block obtained by cutting the obtained crosslinked hydrogel polymer (GK21).

(Steps for Drying, Pulverizing and Classifying)

Water-absorbing resin powder (B21) was obtained by performing the operation similar to that of Example 1, except that the obtained crosslinked hydrogel polymer crushed product (GKF21) was dried at 185° C. for minutes by a hot air drier.

(Surface Crosslinking Step)

Surface-treated water-absorbing resin particles (S21) were obtained by performing the operation similar to that of Example 1, except that the heat temperature treatment time of the water-absorbing resin powder (B21) was set to 20 minutes.

(Step for Adding Liquid Permeability Enhancer)

The surface-treated water-absorbing resin particles (S21) were subjected to the operation similar to that of Example 1 to obtain a particulate water-absorbing agent (EX-21). The performance of the obtained particulate water-absorbing agent (EX-21) is presented in the following table.

Example 22

(Preparation and Polymerization Steps of (Meth)Acrylic Acid (Salt)-Based Aqueous Monomer Solution)

A crosslinked hydrogel polymer (GK22) was obtained by performing the operation similar to that of Example 1, except that the amount of polyethylene glycol diacrylate was changed to 1.73 g and polyethylene glycol (weight average molecular weight: 2,000, manufactured by Wako Pure Chemical Industries, Ltd.) was not used.

(Gel-Crushing Step)

A crosslinked hydrogel polymer crushed product (GKF22) was obtained by performing the operation similar to that of Example 16, except that 62.7 g (0.075 wt % as an effective ingredient with respect to the raw material monomer component amount of the step (i)) of a methanol solution containing 1 wt % of Adeka Pluronic L-44 (manufactured by ADEKA CORPORATION, effective ingredient: 100 wt %) was sprinkled uniformly on the surface of the block obtained by cutting the obtained crosslinked hydrogel polymer (GK22).

(Steps for Drying, Pulverizing and Classifying)

Water-absorbing resin powder (B22) was obtained by performing the operation similar to that of Example 1, except that the obtained crosslinked hydrogel polymer crushed product (GKF22) was dried at 185° C. for minutes by a hot air drier.

(Surface Crosslinking Step)

Surface-treated water-absorbing resin particles (S22) were obtained by performing the operation similar to that of Example 1, except that the heat temperature treatment time of the water-absorbing resin powder (B22) was set to 30 minutes.

(Step for Adding Liquid Permeability Enhancer)

The surface-treated water-absorbing resin particles (S22) were subjected to the operation similar to that of Example 1 to obtain a particulate water-absorbing agent (EX-22). The performance of the obtained particulate water-absorbing agent (EX-22) is presented in the following table.

Example 23

(Preparation and Polymerization Steps of (Meth)Acrylic Acid (Salt)-Based Aqueous Monomer Solution)

A crosslinked hydrogel polymer (GK23) was obtained by performing the operation similar to that of Example 1, except that the amount of polyethylene glycol diacrylate was changed to 1.73 g and polyethylene glycol (weight average molecular weight: 2,000, manufactured by Wako Pure Chemical Industries, Ltd.) was not used.

(Gel-Crushing Step)

A crosslinked hydrogel polymer crushed product (GKF23) was obtained by performing the operation similar to that of Example 16, except that 62.7 g (0.075 wt % as an effective ingredient with respect to the raw material monomer component amount of the step (i)) of a methanol solution containing 1 wt % of EMULGEN 430 (manufactured by Kao Corporation, effective ingredient: 100 wt %) was sprinkled uniformly on the surface of the block obtained by cutting the obtained crosslinked hydrogel polymer (GK23).

(Steps for Drying, Pulverizing and Classifying)

Water-absorbing resin powder (B23) was obtained by performing the operation similar to that of Example 1, except that the obtained crosslinked hydrogel polymer crushed product (GKF23) was dried at 185° C. for 30 minutes by a hot air drier.

(Surface Crosslinking Step)

Surface-treated water-absorbing resin particles (S23) were obtained by performing the operation similar to that of Example 1, except that the heat temperature treatment time of the water-absorbing resin powder (B23) was set to 30 minutes.

(Step for Adding Liquid Permeability Enhancer)

The surface-treated water-absorbing resin particles (S23) were subjected to the operation similar to that of Example 1 to obtain a particulate water-absorbing agent (EX-23). The performance of the obtained particulate water-absorbing agent (EX-23) is presented in the following table.

Example 24

(Preparation and Polymerization Steps of (Meth)Acrylic Acid (Salt)-Based Aqueous Monomer Solution)

A crosslinked hydrogel polymer (GK24) was obtained by performing the operation similar to that of Example 1, except that the amount of polyethylene glycol diacrylate was changed to 1.73 g and polyethylene glycol (weight average molecular weight: 2,000, manufactured by Wako Pure Chemical Industries, Ltd.) was not used.

(Gel-Crushing Step)

A crosslinked hydrogel polymer crushed product (GKF24) was obtained by performing the operation similar to that of Example 16, except that 62.7 g (0.075 wt % as an effective ingredient with respect to the raw material monomer component amount of the step (i)) of a methanol solution containing 1 wt % of PELEX SS-L (manufactured by Kao Corporation, effective ingredient: 50 wt %) was sprinkled uniformly on the surface of the block obtained by cutting the obtained crosslinked hydrogel polymer (GK24).

(Steps for Drying, Pulverizing and Classifying)

Water-absorbing resin powder (B24) was obtained by performing the operation similar to that of Example 1, except that the obtained crosslinked hydrogel polymer crushed product (GKF24) was dried at 185° C. for 30 minutes by a hot air drier.

(Surface Crosslinking Step)

Surface-treated water-absorbing resin particles (S24) were obtained by performing the operation similar to that of Example 1, except that the heat temperature treatment time of the water-absorbing resin powder (B24) was set to 30 minutes.

(Step for Adding Liquid Permeability Enhancer)

The surface-treated water-absorbing resin particles (S24) were subjected to the operation similar to that of Example 1 to obtain a particulate water-absorbing agent (EX-24). The performance of the obtained particulate water-absorbing agent (EX-24) is presented in the following table.

Example 25

(Preparation and Polymerization Steps of (Meth)Acrylic Acid (Salt)-Based Aqueous Monomer Solution)

A crosslinked hydrogel polymer (GK25) was obtained by performing the operation similar to that of Example 1, except that the amount of polyethylene glycol diacrylate was changed to 1.73 g and polyethylene glycol (weight average molecular weight: 2,000, manufactured by Wako Pure Chemical Industries, Ltd.) was not used.

(Gel-Crushing Step)

A crosslinked hydrogel polymer crushed product (GKF25) was obtained by performing the operation similar to that of Example 16, except that 66.9 g (0.8 wt % as an effective ingredient with respect to the raw material monomer component amount of the step (i)) of a methanol solution containing 10 wt % of Denacol EX-861 (manufactured by Nagase ChemteX Corporation, effective ingredient: 100 wt %) was sprinkled uniformly on the surface of the block obtained by cutting the obtained crosslinked hydrogel polymer (GK25).

(Steps for Drying, Pulverizing and Classifying)

Water-absorbing resin powder (B25) was obtained by performing the operation similar to that of Example 1, except that the obtained crosslinked hydrogel polymer crushed product (GKF25) was dried at 185° C. for 30 minutes by a hot air drier.

(Surface Crosslinking Step)

Surface-treated water-absorbing resin particles (S25) were obtained by performing the operation similar to that of Example 1, except that the heat temperature treatment time of the water-absorbing resin powder (B25) was set to 20 minutes.

(Step for Adding Liquid Permeability Enhancer)

The surface-treated water-absorbing resin particles (S25) were subjected to the operation similar to that of Example 1 to obtain a particulate water-absorbing agent (EX-25). The performance of the obtained particulate water-absorbing agent (EX-25) is presented in the following table.

Example 26

(Gel Polymerization Step)

A crosslinked hydrogel polymer (GK26) was obtained by performing the operation similar to that of Example 1, except that the amount of polyethylene glycol diacrylate was changed to 1.73 g and polyethylene glycol (weight average molecular weight: 2,000, manufactured by Wako Pure Chemical Industries, Ltd.) was not used.

(Gel-Crushing Step)

A crosslinked hydrogel polymer crushed product (GKF26) was obtained by performing the operation similar to that of Example 16, except that 62.7 g (0.050 wt % as an effective ingredient with respect to the raw material monomer component amount of the step (i)) of a methanol solution containing 1 wt % of RHEODOL TW-S120V (manufactured by Kao Corporation, effective ingredient: 100 wt %, catalog HLB value: 14.9) was sprinkled uniformly on the surface of the block obtained by cutting the obtained crosslinked hydrogel polymer (GK26).

(Steps for Drying, Pulverizing and Classifying)

Water-absorbing resin powder (B26) was obtained by performing the operation similar to that of Example 1, except that the obtained crosslinked hydrogel polymer crushed product (GKF26) was dried at 185° C. for 30 minutes by a hot air drier.

(Surface Crosslinking Step)

Surface-treated water-absorbing resin particles (S26) were obtained by performing the operation similar to that of Example 1, except that the heat temperature treatment time of the water-absorbing resin powder (B26) was set to 20 minutes.

(Step for Adding Liquid Permeability Enhancer)

The surface-treated water-absorbing resin particles (S26) were subjected to the operation similar to that of Example 1 to obtain a particulate water-absorbing agent (EX-26). The performance of the obtained particulate water-absorbing agent (EX-26) is presented in the following table.

Example 27

(Preparation and Polymerization Steps of (Meth)Acrylic Acid (Salt)-Based Aqueous Monomer Solution)

A crosslinked hydrogel polymer (GK27) was obtained by performing the operation similar to that of Example 1, except that the amount of polyethylene glycol diacrylate was changed to 1.73 g and polyethylene glycol (weight average molecular weight: 2,000, manufactured by Wako Pure Chemical Industries, Ltd.) was not used.

(Gel-Crushing Step)

A crosslinked hydrogel polymer crushed product (GKF27) was obtained by performing the operation similar to that of Example 16, except that 62.7 g (0.050 wt % as an effective ingredient with respect to the raw material monomer component amount of the step (i)) of a methanol solution containing 1 wt % of KF-354L (manufactured by Shin-Etsu Chemical Co., Ltd., effective ingredient: 100 wt %, catalog LB value: 16) was sprinkled uniformly on the surface of the block obtained by cutting the obtained crosslinked hydrogel polymer (GK27).

(Steps for Drying, Pulverizing and Classifying)

Water-absorbing resin powder (B27) was obtained by performing the operation similar to that of Example 1, except that the obtained crosslinked hydrogel polymer crushed product (GKF27) was dried at 185° C. for 30 minutes by a hot air drier.

(Surface Crosslinking Step)

Surface-treated water-absorbing resin particles (S27) were obtained by performing the operation similar to that of Example 1, except that the heat temperature treatment time of the water-absorbing resin powder (B27) was set to 20 minutes.

(Step for Adding Liquid Permeability Enhancer)

The surface-treated water-absorbing resin particles (S27) were subjected to the operation similar to that of Example 1 to obtain a particulate water-absorbing agent (EX-27). The performance of the obtained particulate water-absorbing agent (EX-27) is presented in the following table.

Example 28J (Preparation and Polymerization Steps of (Meth)Acrylic Acid (Salt)-Based Aqueous Monomer Solution)

A crosslinked hydrogel polymer (GK28) was obtained by performing the operation similar to that of Example 1, except that the amount of polyethylene glycol diacrylate was changed to 1.73 g.

(Gel-Crushing Step)

A crosslinked hydrogel polymer crushed product (GKF28) was obtained by performing the operation similar to that of Example 8, except that as the screw extruder, a meat chopper, which is provided with a porous plate (diameter: 100 mm, pore diameter: 8.0 mm, the number of pores: 54, opening ratio: 34.5%, thickness: 10 mm) at the tip end and in which the screw axis has an outer diameter of 86 mm and of which the internal diameter of the casing is 88 mm, was used.

At this time, the gel grinding energy GGE (1) was 108.0 J/g and the gel grinding energy GGE (2) was 14.2 J/g.

(Steps for Drying, Pulverizing and Classifying)

Water-absorbing resin powder (B28) was obtained by performing the operation similar to that of Example 1, except that the obtained crosslinked hydrogel polymer crushed product (GKF2B) was dried at 185° C. for 30 minutes by a hot air drier.

(Surface Crosslinking Step) and (Step for Adding Liquid Permeability Enhancer)

The water-absorbing resin powder (B28) was subjected to the operation similar to that of Example 1 to obtain surface crosslinked water-absorbing resin particles (S28) and a particulate water-absorbing agent (EX-28). The performance of the obtained particulate water-absorbing agent (EX-28) is presented in the following table.

Example 29

(Preparation and Polymerization Steps of (Meth)Acrylic Acid (Salt)-Based Aqueous Monomer Solution)

A crosslinked hydrogel polymer (GK29) was obtained by performing the operation similar to that of Example 1, except that the amount of polyethylene glycol diacrylate was changed to 1.73 g and 2.090 g (0.075 wt % as an effective ingredient with respect to the monomer component) of AMPHITOL 20BS (manufactured by Kao Corporation, effective ingredient: 30 wt %) was used instead of polyethylene glycol (weight average molecular weight: 2,000, manufactured by Wako Pure Chemical Industries, Ltd.).

(Gel-Crushing Step)

A crosslinked hydrogel polymer crushed product (GKF29) was obtained by performing the operation similar to that of Example 8, except that the rotation speed of the screw axis was set to 225 rpm.

At this time, the gel grinding energy GGE(1) was 182.2 J/g and the gel grinding energy GGE (2) was 58.3 J/g.

(Steps for Drying, Pulverizing and Classifying)

Water-absorbing resin powder (B29) was obtained by performing the operation similar to that of Example 1, except that the obtained crosslinked hydrogel polymer crushed product (GKF29) was dried at 185° C. for 30 minutes by a hot air drier.

(Surface Crosslinking Step)

Surface-treated water-absorbing resin particles (B29) were obtained by performing the operation similar to that of Example 1, except that the heat temperature treatment time of the water-absorbing resin powder (B29) was set to 40 minutes.

(Step for Adding Liquid Permeability Enhancer)

The surface-treated water-absorbing resin particles (S29) were subjected to the operation similar to that of Example 1 to obtain a particulate water-absorbing agent (EX-29). The performance of the obtained particulate water-absorbing agent (EX-29) is presented in the following table.

Example 30

(Preparation and Polymerization Steps of (Meth)Acrylic Acid (Salt)-Based Aqueous Monomer Solution)

A crosslinked hydrogel polymer (GK30) was obtained by performing the operation similar to that of Example 1, except that the amount of polyethylene glycol diacrylate was changed to 1.73 g and 2.090 g (0.075 wt % as an effective ingredient with respect to the monomer component) of AMPHITOL 20BS (manufactured by Kao Corporation, effective ingredient 30 wt %) was used instead of polyethylene glycol (weight average molecular weight: 2,000, manufactured by Wako Pure Chemical Industries, Ltd.).

(Gel-Crushing Step)

A crosslinked hydrogel polymer crushed product (GKF30) was obtained by performing the operation similar to that of Example 8, except that the rotation speed of the screw axis was set to 225 rpm.

At this time, the gel grinding energy GGE (1) was 182.2 J/g and the gel grinding energy GGE (2) was 58.3 J/g.

(Steps for Drying, Pulverizing and Classifying)

Water-absorbing resin powder (B30) was obtained by performing the operation similar to that of Example 1, except that the obtained crosslinked hydrogel polymer crushed product (GKF30) was dried at 185° C. for 30 minutes by a hot air drier.

(Surface Crosslinking Step)

Surface-treated water-absorbing resin particles (S30) were obtained by performing the operation similar to that of Example 1, except that the heat temperature treatment time of the water-absorbing resin powder (B30) was set to 20 minutes.

(Step for Adding Liquid Permeability Enhancer)

The surface-treated water-absorbing resin particles (S30) were subjected to the operation similar to that of Example 1 to obtain a particulate water-absorbing agent (EX-30). The performance of the obtained particulate water-absorbing agent (EX-30) is presented in the following table.

Example 31

(Preparation and Polymerization Steps of (Meth)Acrylic Acid (Salt)-Based Aqueous Monomer Solution)

A crosslinked hydrogel polymer (GK31) was obtained by performing the operation similar to that of Example 11.

(Gel-Crushing Step)

A crosslinked hydrogel polymer crushed product (GKF31) was obtained by performing the operation similar to that of Example B, except that as the screw extruder, a meat chopper, which is provided with a porous plate (diameter: 100 mm, pore diameter: 6.4 mm, the number of pores: 83, opening ratio: 34.0%, thickness: 10 mm) at the tip end and in which the screw axis has an outer diameter of 86 mm and of which the internal diameter of the casing is 88 mm, was used, the rotation speed of the screw axis was set to 130 rpm, and a crosslinked hydrogel polymer (GK32) was supplied at 4,640 g/min to the meat chopper.

At this time, the gel grinding energy GGE (1) was 56.4 J/g and the gel grinding energy GGE (2) was 13.1 J/g.

(Steps for Drying, Pulverizing and Classifying)

Water-absorbing resin powder (B31) was obtained by performing the operation similar to that of Example 1, except that the obtained crosslinked hydrogel polymer crushed product (GKF31) was dried at 190° C. for 30 minutes by a hot air drier.

(Surface Crosslinking Step)

Surface-treated water-absorbing resin particles (S31) were obtained by performing the operation similar to that of Example 1, except that the heat temperature treatment time of the water-absorbing resin powder (B31) was set to 20 minutes.

(Step for Adding Liquid Permeability Enhancer)

The surface-treated water-absorbing resin particles (S31) were subjected to the operation similar to that of Example 1 to obtain a particulate water-absorbing agent (EX-31). The performance of the obtained particulate water-absorbing agent (EX-31) is presented in the following table.

Example 32

(Preparation and Polymerization Steps of (Meth)Acrylic Acid (Salt)-Based Aqueous Monomer Solution)

A crosslinked hydrogel polymer (GK32) was obtained by performing the operation similar to that of Example 13.

(Gel-Crushing Step)

A crosslinked hydrogel polymer crushed product (GKF32) was obtained by performing the operation similar to that of Example 8, except that as the screw extruder, a meat chopper, which is provided with a porous plate (diameter: 100 mm, pore diameter: 6.4 mm, the number of pores: 83, opening ratio: 34.0%, thickness: 10 mm) at the tip end and in which the screw axis has an outer diameter of 86 mm and of which the internal diameter of the casing is 88 mm, was used, the rotation speed of the screw axis was set to 130 rpm, and a crosslinked hydrogel polymer (GK33) was supplied at 4,640 g/min to the meat chopper.

At this time, the gel grinding energy GGE (1) was 56.7 J/g and the gel grinding energy GGE (2) was 12.6 J/g.

(Steps for Drying, Pulverizing and Classifying)

Water-absorbing resin powder (B32) was obtained by performing the operation similar to that of Example 1, except that the obtained crosslinked hydrogel polymer crushed product (GKF32) was dried at 190° C. for 30 minutes by a hot air drier.

(Surface Crosslinking Step)

Surface-treated water-absorbing resin particles (S32) were obtained by performing the operation similar to that of Example 1, except that the heat temperature treatment time of the water-absorbing resin powder (B32) was set to 20 minutes.

(Step for Adding Liquid Permeability Enhancer)

The surface-treated water-absorbing resin particles (S32) were subjected to the operation similar to that of Example 1 to obtain a particulate water-absorbing agent (EX-32). The performance of the obtained particulate water-absorbing agent (EX-32) is presented in the following table.

Comparative Example 1

Hydrogel particles (CGKF-1), water-absorbing resin powder (CB-1), surface-treated water-absorbing resin particles (CS1), and a particulate water-absorbing agent (CEX-1) were obtained by performing the treatment similar to that of Example 1, except that the die aperture diameter of the meat chopper used in the gel-crushing step was changed from 3.5 mm to 9.0 mm in Example 1.

The performances of the obtained hydrogel particles (CGKF-1), water-absorbing resin powder (CB-1), particulate water-absorbing agent (CEX-1) are presented in the following table.

Comparative Example 2

The S1 obtained in Example 1 was used as a comparative water-absorbing agent (CEX-2). The performance of the obtained particulate water-absorbing agent (CEX-2) is presented in the following table.

Comparative Example 3

Water-absorbing resin powder (CB-3) having a granulated form and a comparative water-absorbing agent (CEX-3)

were obtained by performing the operation similar to that of Example 1 of Application No. PCT/JP2015/56110. The performances of the obtained water-absorbing resin powder (CB-3) and particulate water-absorbing agent (CEX-3) are presented in the following table.

Comparative Example 4

Water-absorbing resin powder (CB-4) having a granulated form and a comparative water-absorbing agent (CEX-4) were obtained by performing the operation similar to that of Example 2 of Application No. PCT/JP2015/56110. The performances of the obtained water-absorbing resin powder (CB-4) and particulate water-absorbing agent (CEX-4) are presented in the following table.

Comparative Example 5

Hydrogel particles (CGKF-5), water-absorbing resin powder (CB-5), and a comparative particulate water-absorbing agent (CEX-5) were prepared by the method described in Example 6 of WO 2011/126079 A. The performances of the obtained hydrogel particles (CGKF-5), water-absorbing resin powder (CB-5), water-absorbing resin powder (CEX-5), and particulate water-absorbing agent (CEX-6) are presented in the following table.

Comparative Example 6

Hydrogel particles (CGKF-6), water-absorbing resin powder (CB-6), and a comparative water-absorbing agent (CEX-6) were obtained by performing the operation similar to that of Example 13 of WO 2015/030130 A. The performances of the obtained hydrogel particles (CGKF-6), water-absorbing resin powder (CB-6), and particulate water-absorbing agent (CEX-6) are presented in the following table.

Comparative Example 7

Hydrogel particles (CGKF-6) and a comparative water-absorbing agent (CEX-7) were obtained by performing the operation similar to that of Example 6 of WO 2008/096713 A. The performances of the obtained hydrogel particles (CGKF-6) and particulate water-absorbing agent (CEX-7) are presented in the following table.

Comparative Example 8

(Preparation and Polymerization Steps of (Meth)Acrylic Acid (Salt)-Based Aqueous Monomer Solution)

A crosslinked hydrogel polymer (CGK8) was obtained by performing the operation similar to that of Example 1, except that 0.418 g (0.05 with respect to the monomer component) of sodium di(2-ethylhexyl)sulfosuccinate was used instead of polyethylene glycol.

(Gel-Crushing Step)

A crosslinked hydrogel polymer crushed product (CGKF8) was obtained by performing the operation similar to that of Example 1.

(Steps for Drying, Pulverizing and Classifying)

Water-absorbing resin powder (CB8) was obtained by performing the operation similar to that of Example 1, except that the obtained crosslinked hydrogel polymer crushed product (GKF8) was dried at 185° C. for 30 minutes by a hot air drier.

(Surface Crosslinking Step)

Surface-treated water-absorbing resin particles (CS8) were obtained by performing the operation similar to that of Example 1, except that the heat temperature treatment time of the water-absorbing resin powder (CB8) was set to 60 minutes.

(Step for Adding Liquid Permeability Enhancer)

The surface-treated water-absorbing resin particles (CS5) were subjected to the operation similar to that of Example 1 to obtain a particulate water-absorbing agent (CEX-8). The performance of the obtained particulate water-absorbing agent (CEX-8) is presented in the following table.

TABLE 1

| | Additive | |
|---|---|---|
| | Type | Amount (wt %/ monomer weight) |
| Example 1 | Polyethylene glycol (Mw2000) | 0.8 |
| Example 2 | Polyethylene glycol (Mw2000) | 0.4 |
| Example 3 | Polyethylene glycol (Mw2000) | 1.2 |
| Example 4 | Polyethylene glycol (Mw400) | 0.8 |
| Example 5 | Polyethylene glycol (Mw20000) | 0.8 |
| Example 6 | Polyethylene glycol (Mw2000) | 0.8 |
| Example 7 | Polyethylene glycol (Mw2000) | 0.8 |
| Example 8 | Polyethylene glycol (Mw2000) | 0.8 |
| Example 9 | Polyethylene glycol (Mw2000) | 0.8 |
| Example 10 | Polyethylene glycol (Mw2000) | 0.8 |
| Example 11 | Polyethylene glycol (Mw2000) | 0.8 |
| Example 12 | AMPHITOL 20BS | 0.075 |
| Example 13 | AMPHITOL 20BS | 0.075 |
| Example 14 | AMPHITOL 20BS | 0.075 |
| Example 15 | AMPHITOL 20BS | 0.075 |
| Example 16 | AMPHITOL 20BS | 0.075 |
| Example 17 | AMPHITOL 20HD | 0.075 |
| Example 18 | AMPHITOL 20N | 0.075 |
| Example 19 | AMIET 105A | 0.05 |
| Example 20 | EMAL 20C | 0.075 |
| Example 21 | ACETAMIN 24 | 0.075 |
| Example 22 | Pluronic L-44 | 0.075 |
| Example 23 | EMULGEN 430 | 0.075 |
| Example 24 | PELEX SS-L | 0.075 |
| Example 25 | Denacol Ex861 | 0.8 |
| Example 26 | RHEODOL TW-S120V | 0.05 |
| Example 27 | KF-354L | 0.05 |
| Example 28 | Polyethylene glycol (Mw2000) | 0.8 |
| Example 29 | AMPHITOL 20BS | 0.075 |
| Example 30 | AMPHITOL 20BS | 0.075 |
| Example 31 | Polyethylene glycol (Mw2000) | 0.8 |
| Example 32 | AMPHITOL 20BS | 0.075 |
| Comparative Example 1 | Polyethylene glycol (Mw2000) | 0.8 |
| Comparative Example 2 | Polyethylene glycol (Mw2000) | 0.8 |
| Comparative Example 3 | None | 0 |
| Comparative Example 4 | None | 0 |
| Comparative Example 5 | None | 0 |
| Comparative Example 6 | Polyoxyethylene sorbitan monostearate | 0.007 |
| Comparative Example 7 | Polyethylene glycol (Mw2000) | 1.0 |
| Comparative Example 8 | Sodium di(2-ethylhexyl)sulfosuccinate | 0.05 |

TABLE 2

| Poly(meth)acrylic acid (salt)-based particulate water-absorbing agent | | CRC g/g | Moisture content % | D50 μm | Logarithmic standard deviation δξ | AAP g/g | Vortex Second | GCA g/g | FGBP ×10$^{-9}$ cm$^2$ | Surface tension mN/m |
|---|---|---|---|---|---|---|---|---|---|---|
| EX-1 | Example 1 | 35.1 | 3.3 | 360 | 0.358 | 28.5 | 21 | 32.6 | 210 | 65 |
| EX-2 | Example 2 | 35.0 | 3.3 | 358 | 0.357 | 27.8 | 24 | 31.5 | 203 | 65 |
| EX-3 | Example 3 | 35.3 | 3.0 | 352 | 0.356 | 28.1 | 22 | 32.0 | 202 | 64 |
| EX-4 | Example 4 | 34.8 | 2.7 | 361 | 0.357 | 27.1 | 24 | 31.0 | 191 | 65 |
| EX-5 | Example 5 | 35.5 | 3.1 | 360 | 0.358 | 28.2 | 23 | 32.1 | 220 | 65 |
| EX-6 | Example 6 | 35.1 | 3.2 | 363 | 0.361 | 28.4 | 21 | 32.2 | 217 | 65 |
| EX-7 | Example 7 | 32.0 | 3.1 | 360 | 0.358 | 30.1 | 23 | 31.5 | 132 | 65 |
| EX-8 | Example 8 | 34.7 | 3.3 | 359 | 0.356 | 30.3 | 21 | 32.0 | 213 | 65 |
| EX-9 | Example 9 | 35.0 | 2.9 | 362 | 0.362 | 30.5 | 21 | 32.4 | 195 | 65 |
| EX-10 | Example 10 | 32.0 | 3.3 | 365 | 0.363 | 28.9 | 23 | 30.1 | 381 | 65 |
| EX-11 | Example 11 | 35.1 | 3.1 | 366 | 0.365 | 30.3 | 19 | 34.0 | 235 | 65 |
| EX-12 | Example 12 | 34.8 | 3.2 | 354 | 0.356 | 30.3 | 19 | 33.9 | 208 | 64 |
| EX-13 | Example 13 | 35.7 | 3.5 | 361 | 0.357 | 30.7 | 15 | 35.4 | 201 | 64 |
| EX-14 | Example 14 | 35.0 | 3.4 | 445 | 0.390 | 30.0 | 17 | 33.2 | 195 | 64 |
| EX-15 | Example 15 | 36.2 | 3.1 | 364 | 0.362 | 29.7 | 14 | 35.1 | 92 | 64 |
| EX-16 | Example 16 | 34.9 | 3.2 | 364 | 0.362 | 27.0 | 18 | 34.3 | 160 | 65 |
| EX-17 | Example 17 | 35.2 | 3.2 | 359 | 0.358 | 27.2 | 21 | 34.3 | 156 | 66 |
| EX-18 | Example 18 | 35.1 | 3.2 | 366 | 0.365 | 27.8 | 17 | 34.5 | 177 | 66 |
| EX-19 | Example 19 | 35.0 | 3.0 | 358 | 0.357 | 27.1 | 20 | 33.4 | 135 | 67 |
| EX-20 | Example 20 | 34.9 | 3.1 | 358 | 0.357 | 26.6 | 20 | 33.6 | 175 | 63 |
| EX-21 | Example 21 | 34.7 | 3.3 | 369 | 0.370 | 28.9 | 21 | 33.2 | 171 | 62 |
| EX-22 | Example 22 | 35.2 | 3.1 | 360 | 0.358 | 27.1 | 23 | 31.9 | 143 | 64 |
| EX-23 | Example 23 | 35.0 | 3.2 | 362 | 0.360 | 26.9 | 24 | 32.1 | 178 | 65 |
| EX-24 | Example 24 | 35.1 | 3.2 | 362 | 0.360 | 27.0 | 23 | 31.7 | 149 | 67 |
| EX-25 | Example 25 | 35.1 | 3.4 | 367 | 0.364 | 26.7 | 22 | 31.5 | 137 | 68 |
| EX-26 | Example 26 | 35.1 | 3.3 | 361 | 0.359 | 26.8 | 24 | 31.5 | 145 | 63 |
| EX-27 | Example 27 | 35.2 | 3.4 | 358 | 0.358 | 27.1 | 23 | 31.2 | 135 | 62 |
| EX-28 | Example 28 | 35.1 | 3.1 | 367 | 0.365 | 30.5 | 27 | 28.5 | 405 | 66 |
| EX-29 | Example 29 | 34.3 | 3.1 | 362 | 0.361 | 30.4 | 15 | 33.7 | 229 | 64 |
| EX-30 | Example 30 | 40.1 | 3.2 | 362 | 0.360 | 26.2 | 14 | 36.5 | 38 | 64 |
| EX-31 | Example 31 | 38.2 | 3.1 | 365 | 0.363 | 27.0 | 20 | 33.8 | 69 | 66 |
| EX-32 | Example 32 | 37.8 | 3.1 | 364 | 0.363 | 28.1 | 17 | 34.5 | 61 | 65 |
| CEX-1 | Comparative Example 1 | 35.0 | 3.6 | 358 | 0.358 | 28.4 | 44 | 25.5 | 255 | 65 |
| CEX-2 | Comparative Example 2 | 35.1 | 3.0 | 361 | 0.362 | 31.5 | 25 | 34.0 | 15 | 65 |
| CEX-3 | Comparative Example 3 | 33.5 | 4.2 | 345 | 0.352 | 30.2 | 26 | 32.3 | 40 | 72 |
| CEX-4 | Comparative Example. 4 | 33.8 | 4.1 | 343 | 0.356 | 25.7 | 24 | 28.3 | 87 | 72 |
| CEX-5 | Comparative Example 5 | 27.0 | 3.5 | 390 | 0.360 | 27.2 | 32 | 27.0 | 395 | 72 |
| CEX-6 | Comparative Example 6 | 27.8 | 3.6 | 456 | 0.410 | 26.2 | 35 | 25.1 | 352 | 70 |
| CEX-7 | Comparative Example 7 | 34.6 | 3.3 | 450 | 0.312 | 7.2 | 48 | 23.5 | 86 | 64 |
| CEX-8 | Comparative Example 8 | 27.5 | 3.5 | 360 | 0.358 | 27.2 | 18 | 25.2 | 207 | 44 |

TABLE 3

| Hydrogel particles | CRC [g/g] | Solids content [wt %] | Polymerization rate [wt %] | Weight average particle diameter [μm] | Weight average particle diameter in terms of dried product [μm] |
|---|---|---|---|---|---|
| GKF1 | 32.9 | 40.2 | 98.3 | 212 | 156 |
| GKF2 | 34.1 | 40.3 | 98.2 | 237 | 175 |
| GKF3 | 32.5 | 39.6 | 98.4 | 195 | 143 |
| GKF4 | 33.3 | 40.5 | 98.3 | 270 | 200 |
| GKF5 | 35.1 | 39.9 | 98.3 | 205 | 151 |
| GKF6 | 36.5 | 40.0 | 98.2 | 203 | 150 |
| GKF7 | 32.9 | 40.2 | 98.5 | 212 | 156 |
| GKF8 | 32.2 | 39.5 | 98.5 | 302 | 222 |
| GKF9 | 32.5 | 39.2 | 97.9 | 311 | 228 |
| GKF10 | 32.2 | 39.5 | 98.3 | 302 | 222 |
| GKF11 | 39.6 | 42.7 | 98.2 | 280 | 211 |
| GKF12 | 39.2 | 43.8 | 98.2 | 597 | 453 |
| GKF13 | 38.3 | 41.9 | 98.6 | 290 | 217 |
| GKF14 | 34.1 | 39.8 | 98.2 | 201 | 148 |
| GKF15 | 34.1 | 39.8 | 98.6 | 201 | 148 |
| GKF16 | 31.3 | 40.1 | 98.7 | 234 | 173 |
| GKF17 | 32.0 | 39.9 | 98.4 | 211 | 155 |
| GKF18 | 30.8 | 39.8 | 98.4 | 243 | 179 |
| GKF19 | 31.4 | 40.0 | 98.7 | 238 | 175 |
| GKF20 | 32.1 | 39.6 | 98.5 | 240 | 176 |
| GKF21 | 30.9 | 40.5 | 98.5 | 222 | 164 |
| GKF22 | 30.2 | 40.2 | 98.5 | 225 | 166 |
| GKF23 | 31.1 | 39.7 | 97.9 | 236 | 173 |
| GKF24 | 31.5 | 40.1 | 98.1 | 218 | 161 |
| GKF25 | 31.2 | 39.8 | 98.4 | 217 | 160 |
| GKF26 | 31.8 | 40.2 | 98.2 | 223 | 165 |
| GKF27 | 30.9 | 40.1 | 98.5 | 222 | 164 |
| GKF28 | 33.2 | 40.1 | 98.3 | 852 | 628 |
| GKF29 | 34.1 | 39.8 | 98.2 | 201 | 148 |
| GKF30 | 34.1 | 39.8 | 98.4 | 201 | 148 |

TABLE 3-continued

| Hydrogel particles | CRC [g/g] | Solids content [wt %] | Polymerization rate [wt %] | Weight average particle diameter [μm] | Weight average particle diameter in terms of dried product [μm] |
|---|---|---|---|---|---|
| GKF31 | 37.3 | 42.7 | 98.2 | 486 | 366 |
| GKF32 | 37.7 | 43.6 | 98.2 | 494 | 374 |
| CGKF1 | 32.9 | 40.2 | 98.3 | 945 | 699 |
| CGKF5 | 29.1 | 79.8 | 97.8 | 367 | 291 |
| CGKF6 | 27.2 | 53.5 | 97.9 | 915 | 740 |
| CGKF7 | — | — | — | 5284 | 3916 |
| CGKF8 | 31.8 | 39.8 | 97.6 | 247 | 182 |

TABLE 4

| Water-absorbing resin powder | CRC [g/g] | weight average particle diameter [μm] | Logarithmic standard deviation δξ |
|---|---|---|---|
| B1 | 46.6 | 346 | 0.36 |
| B2 | 47.2 | 346 | 0.36 |
| B3 | 45.1 | 346 | 0.36 |
| B4 | 46.9 | 346 | 0.36 |
| B5 | 47.5 | 346 | 0.36 |
| B6 | 46.5 | 346 | 0.36 |
| B7 | 46.6 | 346 | 0.36 |
| B8 | 44.7 | 346 | 0.36 |
| B9 | 45.6 | 346 | 0.36 |
| B10 | 44.7 | 346 | 0.36 |
| B11 | 41.8 | 346 | 0.36 |
| B12 | 46.9 | 346 | 0.36 |
| B13 | 42.8 | 346 | 0.36 |
| B14 | 42.3 | 429 | 0.38 |
| B15 | 42.3 | 346 | 0.36 |
| B16 | 44.4 | 346 | 0.36 |
| B17 | 44.7 | 346 | 0.36 |
| B18 | 45.8 | 346 | 0.36 |
| B19 | 45.5 | 346 | 0.36 |
| B20 | 46.2 | 346 | 0.36 |
| B21 | 39.3 | 346 | 0.36 |
| B22 | 46.1 | 346 | 0.36 |
| B23 | 47.0 | 346 | 0.36 |
| B24 | 46.3 | 346 | 0.36 |
| B25 | 42.9 | 346 | 0.36 |
| B26 | 44.9 | 346 | 0.36 |
| B27 | 44.9 | 346 | 0.36 |
| B28 | 45.3 | 346 | 0.36 |
| B29 | 42.3 | 346 | 0.36 |
| B30 | 42.3 | 346 | 0.36 |
| B31 | 43.9 | 346 | 0.36 |
| B32 | 44.4 | 346 | 0.36 |
| CB1 | 46.6 | 346 | 0.36 |
| CB3 | 43.5 | 344 | 0.33 |
| CB4 | 43.5 | 344 | 0.33 |
| CB5 | 27.0 | 390 | 0.36 |
| CB6 | 32.0 | 450 | 0.40 |
| CB8 | 42.3 | 346 | 0.36 |

TABLE 5

| Water-absorbing resin powder (425/300) | BET specific surface area [m²/kg] |
|---|---|
| B1 | 33.2 |
| B9 | 34.0 |
| CB1 | 25.9 |
| CB5 | 28.8 |

<SEM Photograph>

FIG. 2 shows an SEM photograph of the water-absorbing resin powder of Example 9 (particle size cut: 500/425) and the measurement conditions are magnification of 30 and an applied voltage of 1.3 kV.

FIG. 3 shows an SEM photograph of the water-absorbing resin powder of Example 9 (particle size cut: 500/425) and the measurement conditions are magnification of 130 and an applied voltage of 1.3 kV.

FIG. 4 shows an SEM photograph of the water-absorbing resin powder of Comparative Example 1 (particle size cut: 500/425) and the measurement conditions are magnification of 30 and an applied voltage of 1.3 kV.

FIG. 5 shows an SEM photograph of the water-absorbing resin powder of Comparative Example 6 (particle size cut: 500/425) and the measurement conditions are magnification of 130 and an applied voltage of 1.3 kV.

[Absorbent Material Performance Evaluation]

(Evaluation Method of Physiological Saline Solution Absorbing Speed (Core Acquisition) and Re-Wet Amount of Absorbent Material)

An absorbent material to be measured was produced by the following method. That is, first, a water-absorbing sheet 12 (80 mm×80 mm, thickness: about 0.1 mm) was spread out in an acrylic resin container 11 (inside dimension: 80 mm×80 mm, height: 4 cm), 2.4 g of a water-absorbing agent 13 was then uniformly scattered thereon, a water-absorbing sheet. 14 (80 mm×80 mm, thickness: about 0.1 mm) was spread out thereon, and a surface sheet 15 (80 mm×80 mm, thickness: about 0.1 mm) having liquid permeability and collected from a commercially available diaper was further placed thereon, thereby producing an absorbent material 18 as a model diaper (the concentration of the water-absorbing agent including the water-absorbing sheet: about 82%).

Then, a liquid feeding apparatus 16 (weight: 80 g, a load applied to the absorbent material: 1.25 g/cm² (0.1 kPa)), having a cylinder with a diameter of 30 mm, a height of 120 mm to which liquid can be supplied through a central portion) was placed onto the absorbent material 18 as a model diaper such that a load was uniformly applied. Next, 48 g of a physiological saline solution (0.90% aqueous sodium chloride solution) set at 37° C. was poured in the cylinder quickly (at once). A period of time from the time point when the physiological saline solution was started to be poured until the physiological saline solution was completely absorbed by the absorbent material was measured and set as a first speed (second) of Absorbing the physiological saline solution. After 30 minutes, four weights 17 (weight: 180 g) were placed around the cylinder of the liquid feeding apparatus 16 such that a load of 12.5 g/cm² (1.2 kPa) was uniformly applied to the whole absorbent material, and 24 g of the physiological saline solution set at 37° C. was poured in the cylinder quickly (at once). A period of time from the time point when the physiological saline solution was started to be poured until the physiological saline solution was completely absorbed by the absorbent material 18 was measured and set as a second speed (second) of absorbing the physiological saline solution. After 3 minutes, the liquid feeding apparatus 16 and the weights 17 placed on the absorbent material 18 were removed, a paper towel (manufacturer: Oji Nepia Co., Ltd., kitchen towel, a product obtained by cutting into 80 mm×80 mm and overlapping 30 sheets thereof) was placed on the absorbent material 18, and a load of 30 g/cm² (3.0 kPa) was placed thereon to be left to stand for 1 minute. The amount of liquid absorbed by the paper towel was obtained by measuring a change in weight of the paper towel, and this amount was regarded as the re-wet amount (g).

is shown at the first time and particularly at the second time, but the re-wet amount is largely increased so that it is not possible to achieve a performance balance between the re-wet amount and the absorbing speed.

Further, as described in Comparative Example 8, in the water-absorbing material using the particulate water-absorbing agent (CEX-8) out of the range of the invention in which FGBP is high, but CRC and GCA are low and the surface tension is low, an excellent absorbing speed is shown at the first time and particularly at the second time, but the re-wet amount is largely increased so that it is not possible to achieve a performance balance between the re-wet amount and the absorbing speed.

TABLE 6

| | Water-absorbing agent | | | | Absorbent material | | |
|---|---|---|---|---|---|---|---|
| | | | | | Absorption speed [s] | | Re-wet |
| | CRC [g/g] | GCA [g/g] | FGBP [×10⁻⁹ cm²] | Surface tension mN/m | First time | Second time | amount [g] |
| Particulate absorbing agent (EX-1) | 35.1 | 32.6 | 210 | 65 | 15 | 65 | 2.3 |
| Comparative absorbing agent (CEX-2) | 35.1 | 34.0 | 15 | 65 | 16 | 86 | 2.7 |
| Comparative absorbing agent (CEX-6) | 27.8 | 25.1 | 352 | 70 | 13 | 58 | 9.9 |
| Comparative absorbing agent (CEX-8) | 27.5 | 25.2 | 207 | 44 | 14 | 62 | 15.8 |

(Evaluation Result of Absorbent Material)

Evaluations of the absorbing speed (core acquisition) of the physiological saline solution into the absorbent material and the re-wet amount from the absorbent material of each of the particulate water-absorbing agents (EX-1), (CEX-2), (CEX-6), and (CEX-8) obtained in Example 1, Comparative Example 2, Comparative Example 6, and Comparative Example 8 were measured. As for these measurement or evaluation methods, measurement was carried out according to the above-described absorbent material performance evaluation. The results thereof are presented in the following table.

As described in Example 1, in the water-absorbing material using the particulate water-absorbing agent (EX-1) in which a balance between GCA and FGBP is highly achieved, an excellent absorbing speed is shown at the first time and particularly at the second time, and it is also possible to reduce the re-Wet amount.

On the other hand, as described in Comparative Example 2, in the water-absorbing material using the particulate water-absorbing agent (CEX-2) out of the range of the invention in which GCA is high but FGBP is low, it is possible to reduce the re-wet amount, but the absorbing speeds at the first time and particularly at the second time are decreased so that it is not possible to achieve a performance balance between the re-wet amount and the absorbing speed. Further, as described in Comparative Example 6, in the water-absorbing material using the particulate water-absorbing agent (CEX-6) out of the range of the invention in which GCA is low and FGBP is high, an excellent absorbing speed

REFERENCE SIGNS LIST

1 Filtration apparatus
2 Glass filter
3 Silicone tube
4 Stop cock
5 Glass tube
6 Tank
7 Support cylinder
8 High humidity strength cellulose tissue
9 Piston
10 Metal ring
11 Acrylic resin container
12 Water-absorbing sheet
13 Water-absorbing agent
14 Water-absorbing sheet
15 Surface sheet
16 Liquid feeding apparatus
17 Weight
18 Absorbent material Incidentally, the entire contents of the prior Japanese Patent Application No. 2015-123529 filed on Jun. 19, 2015 are incorporated in this application by reference.

The invention claimed is:
1. A method for producing a poly(meth)acrylic acid (salt)-based particulate water-absorbing agent containing poly(meth)acrylic acid (salt)-based water-absorbing resin particles as a main component, the method comprising:
(i) a step for preparing a (meth)acrylic acid (salt)-based aqueous monomer solution;
(ii) a step for polymerizing the (meth)acrylic acid (salt)-based aqueous monomer solution;

(iii) a step for gel-crushing a crosslinked hydrogel polymer during polymerization or after polymerization to obtain hydrogel particles;
(iv) a step for drying the hydrogel particles to obtain a dried product;
(v) a step for pulverizing and/or classifying the dried product to obtain water-absorbing resin powder;
(vi) a step for surface crosslinking the water-absorbing resin powder to obtain water-absorbing resin particles; and
(vii) a step for adding a liquid permeability enhancer to the water-absorbing resin powder or the water-absorbing resin particles, wherein
the method further includes adding an adhesion controlling agent, which controls adhesion of the crosslinked hydrogel polymer and/or the hydrogel particles, in the step (iii) or before the step (iii), and where the adhesion controlling agent is added in an amount of 0.03 wt % to 2 wt % with respect to the raw material monomer of the crosslinked hydrogel polymer,
a solid content of the hydrogel particles is adjusted to 10 wt % to 80 wt % and a weight average particle diameter (RB) of the hydrogel particles is adjusted to 50 μm to 460 μm, and
a surface tension of the poly(meth)acrylic acid (salt)-based particulate water-absorbing agent is adjusted to 60 mN/m or more, and an absorption capacity without pressure (CRC) is adjusted to 28 g/g or more;
the adhesion controlling agent is one or more compounds selected from a nonionic substance, an amphoteric substance, an anionic substance, and a cationic substance,
the nonionic substance is (a) a polyol, (b) a hydroxy group-modified product of a polyol, (c) side-chain and/or terminal polyether-modified polysiloxane, or (d) an alkylene oxide adduct of higher aliphatic amine,
the amphoteric substance is (e) alkylaminobetaine or (f) alkylamine oxide,
the anionic substance is (g) a sulfuric acid ester salt of a higher alcohol alkylene oxide adduct or (h) alkyl diphenyl ether disulfonate, and
the cationic substance is (i) an ammonium salt.

2. The method according to claim 1, wherein weight average molecular weights of the nonionic substance or (g) the sulfuric acid ester salt of the higher alcohol alkylene oxide adduct are each independently 200 to 200,000.

3. The method according to claim 1, wherein (a) the polyol is (poly)alkylene glycol.

4. The method according to claim 1, wherein
(b) the hydroxy group-modified product of the polyol is (b-1) a glycidyl-modified polyol, (b-2) an alkylene oxide adduct of higher alcohol, or (b-3) an alkylene oxide adduct of a polyhydric alcohol fatty acid ester,
(b-1) is (poly)alkylene glycol of which at least one of ends is modified with a glycidyl group,
(b-2) is (poly)alkylene glycol of which one end is modified with a substituent having a C1 to C30 hydrocarbon, and
(b-3) is polyhydric alcohol of which at least one hydroxy group is combined with alkylene oxide and at least one hydroxy group of which is modified with a substituent having a C1 to C30 hydrocarbon via an ester bond, and the polyhydric alcohol is glycerin, pentaerythritol, sorbitol, sorbitan, or sugar.

5. The method according to claim 1, wherein (d) the alkylene oxide adduct of higher aliphatic amine is primary amine having a C1 to C30 hydrocarbon and alkylene oxide is added to two hydrogens of the primary amine.

6. The method according to claim 1, wherein (g) the sulfuric acid ester salt of the higher alcohol alkylene oxide adduct is (poly)alkylene glycol of which one end is modified with a substituent having a C1 to C30 hydrocarbon and the other end is a sulfuric acid ester salt.

7. The method according to claim 1, wherein a rate of neutralization of the (meth) acrylic acid (salt)-based aqueous monomer solution in the step (i) is 40 mol % to 90 mol %.

8. The method according to claim 1, wherein the gel-crushing step is performed by using a plurality of gel-crushers.

9. The method according to claim 1, wherein a weight average particle diameter (D50) of the poly(meth)acrylic acid (salt)-based particulate water-absorbing agent is 300 μm to 500 μm.

10. The method according to claim 1, wherein the liquid permeability enhancer is water-insoluble inorganic fine particles.

11. The method according to claim 1, wherein a weight average particle diameter of the hydrogel particles converted to the dried product is 130 μm to 460 μm.

12. The method according to claim 1, wherein the adhesion controlling agent is an alkylene oxide adduct of a polyhydric alcohol fatty acid ester, and the amount of the adhesion controlling agent added is 0.03 wt % to 0.5 wt % with respect to a raw material monomer of the crosslinked hydrogel polymer.

* * * * *

UNITED STATES PATENT AND TRADEMARK OFFICE
CERTIFICATE OF CORRECTION

| | |
|---|---|
| PATENT NO. | : 11,535,689 B2 |
| APPLICATION NO. | : 15/737884 |
| DATED | : December 27, 2022 |
| INVENTOR(S) | : Tsuyoshi Yorino et al. |

It is certified that error appears in the above-identified patent and that said Letters Patent is hereby corrected as shown below:

In the Specification

In Column 74, Line 64, "333 g" should be changed to -- 443g --.

Signed and Sealed this
Twentieth Day of February, 2024

Katherine Kelly Vidal
*Director of the United States Patent and Trademark Office*